United States Patent [19]
Maddon et al.

[11] Patent Number: 6,093,539
[45] Date of Patent: *Jul. 25, 2000

[54] DNA ENCODING THE T CELL SURFACE PROTEIN T4 AND USE OF FRAGMENTS OF T4 IN THE TREATMENT OF AIDS

[75] Inventors: Paul J. Maddon, New York, N.Y.; Dan R. Littman, San Francisco, Calif.; Leonard Chess, Scarsdale; Richard Axel, New York, both of N.Y.; Robin Weiss, London, United Kingdom; J. Steven McDougal, Atlanta, Ga.

[73] Assignee: The Trustees of Columbia University in the City of New York, New York, N.Y.

[ * ] Notice: This patent is subject to a terminal disclaimer.

[21] Appl. No.: 08/466,368

[22] Filed: Jun. 6, 1995

Related U.S. Application Data

[63] Continuation of application No. 08/354,452, Dec. 12, 1994, Pat. No. 5,958,678, which is a continuation of application No. 07/909,021, Jul. 6, 1992, abandoned, which is a continuation-in-part of application No. 07/713,564, Jun. 11, 1991, abandoned, which is a continuation of application No. 06/898,587, Aug. 21, 1986, abandoned.

[51] Int. Cl.[7] .............................. C12Q 1/68; C12N 5/10; C12N 15/12; C12N 15/63
[52] U.S. Cl. .......................... 435/6; 435/69.1; 435/252.3; 435/254.2; 435/320.1; 435/325; 435/348; 536/23.5; 536/24.31
[58] Field of Search .................................. 536/23.1, 23.5, 536/24.3, 24.31; 435/6, 69.1, 252.3, 254.2, 320.1, 325, 348

[56] References Cited

U.S. PATENT DOCUMENTS

| | | | |
|---|---|---|---|
| 5,110,906 | 5/1992 | Maddon et al. | 530/350 |
| 5,126,433 | 6/1992 | Maddon et al. | 530/395 |

OTHER PUBLICATIONS

Barr, P.J. et al., (1989) Yeast Genetic Engineering, Chapter 17 (Exhibit 4).
Carr, S.A., et al., (1989) J. Biol. Chem. 264:21286–21295 (Exhibit 5).
Dalgleish, A.G., et al., (1984) Nature, 312:763–767 (Exhibit 6).
Klatzman, D., et al., (1984) Nature, 312:767–768 (Exhibit 7).
Littman, D.R., et al., (1985) Cell, 40:237–246 (Exhibit 8).
Littman, D.R., et al., (1985) ICSU Short Reports, 2:233–234 (Exhibit 9).
Maddon, P.J., et al., (1985) Cell, 42:93–104 (Exhibit 10).
Murre, C., et al., (1986) Molecular and Cellular Biology, 6:1315–1319 (Exhibit 11).
Possee, R.D., (1986) Virus Research, 5:43–49 (Exhibit 12).
Terhorst, C., et al., (1980) Science, 209:520–521 (Exhibit 13).

*Primary Examiner*—Robert A. Schwartzman
*Attorney, Agent, or Firm*—John P. White; Cooper & Dunham LLP

[57] ABSTRACT

This invention provides an isolated single-stranded nucleic acid which encodes an aqueous-soluble polypeptide comprising at least a portion of a human T4 glycoprotein, which portion specifically forms a complex with a human immunodeficiency virus envelope glycoprotein.

28 Claims, 30 Drawing Sheets

FIGURE 6A

```
                                                                                                  met asn arg gly val pro phe arg his leu leu
CAGCCCAGACCTCCATTCTCTGCAGGTGCCCAGCCCTCTGCCTGCCTCCTGGCCAGGCCACA ATG AAC CGG GGA GTC CCT TTT AGG CAC TTG CTT  108
                                                -20
     -10                                        -1   +1                                          •
leu val leu gln leu ala leu leu pro ala ala thr gln gly asn lys val leu val gly lys gly asp thr val glu leu thr cys
CTG GTG CTG CAA CTG GCG CTC CTG CCA GCA GCC ACT CAG GGA AAC AAA GTG CTG GTG AAA GGG GAT ACA GTG GAA CTG ACC TGT  198
                                                     V1                                                    L
    +20                                  +30
thr ala ser gln lys ser ile gln phe his trp lys asn ser leu gln ile leu gly asn gly ser phe leu thr lys
ACA GCT TCC CAG AAG AGC ATA CAA TTC CAC TGG AAA AAC AGC CTC CAG ATT CTG GGA AAT GGG AGC TTC CTA ACT AAA  288
                                              +40
    +50                          +60
gly pro ser lys leu asn asp arg ala asp ser arg arg ser leu trp asp gln gly asn phe pro leu ile ile lys asn leu lys ile
GGT CCA TCC AAG CTG AAT GAT CGC GCT GAC TCA AGA AGA AGC CTT TGG GAC CAA GGA AAC TTC CCC CTG ATC ATC AAG AAT CTT AAG ATA  378
                                                                       +70
    +80                                                                                                     J1
glu asp ser asp thr tyr ile cys glu val glu asp gln lys glu glu val gln leu leu val phe gly leu thr phe glu asp ser gly thr
GAA GAC TCA GAT ACT TAC ATC TGT GAA GTG GAG GAC CAG AAG GAG GAG GTA CAA TTG CTA GTG TTC GGA TTA ACT TTC GAC GAC TCT GGA ACC  468
                                                                                     +130                 •
              +90                                     +100
his leu leu gly gln leu ser leu thr leu glu ser pro pro gly ser ser pro gly thr trp thr cys val leu gln asn gln lys
CAC CTG CTT CAG CTG AGC CTG ACC CTG GAG AGC CCT CCT GGT AGT AGC CCA GGC ACC TGG ACA TGC GTC TTG CAG AAC CAG AAG  558
                                                                               +160    o
             +110                                 +120
asn ile gln gly gly lys thr leu glu leu his gln leu leu leu gln ser leu lys ser val
AAC ATA CAG GGG AAG ACC CTG GAG CTG CAC CAG CTC CTA CTG
                                                                                       +190
              +140                               +150
lys val glu phe lys ile asp ile val val leu ala phe gln met leu lys ala ser ile val tyr lys lys glu gly glu gln val glu phe
AAG GTG GAG TTC AAA ATA GAC ATC GTG GTC CTA GCT TTC CAG ATG CTG AAG GCC TCC ATC GTC TAT AAG AAA CAG GAA CAG GTG GAG TTC  738
                         J2                                                    V3
                                                  +180
             +170                                                                   +220
ser phe pro leu ala phe thr val glu lys leu thr gly ser gly glu leu arg ala ser ser lys ser trp
TCC TTC CCA CTC GCC TTT ACA GTT GAA AAG CTG ACG GGC AGT GGC GAG GAG AGG GCT TCC TCC AAG TCT TGG  828
                                   +210
```

```
                      100
T4 J          L V F G  L - T  A N S  D T H
Consensus Jβ  L Y F G  E G T  R L T  V L -
Consensus Jλ  W V F G  G G T  K V T  V L G
Consensus Jκ  - T F G  G G T  K L E  I K R
HPB-MLT α J   I I F G  S G T  R L S  I R -
```

FIGURE 9C

```
                    370              380                390
T4           S T P V Q P M A L I V L G G V A G L L F I G L G I F F C V R
MHC cl.IIβ   S T S A Q N K M L S G V G G F V L G L L F L G L G L E I Y F R
                                        ─────────TM─────────
```

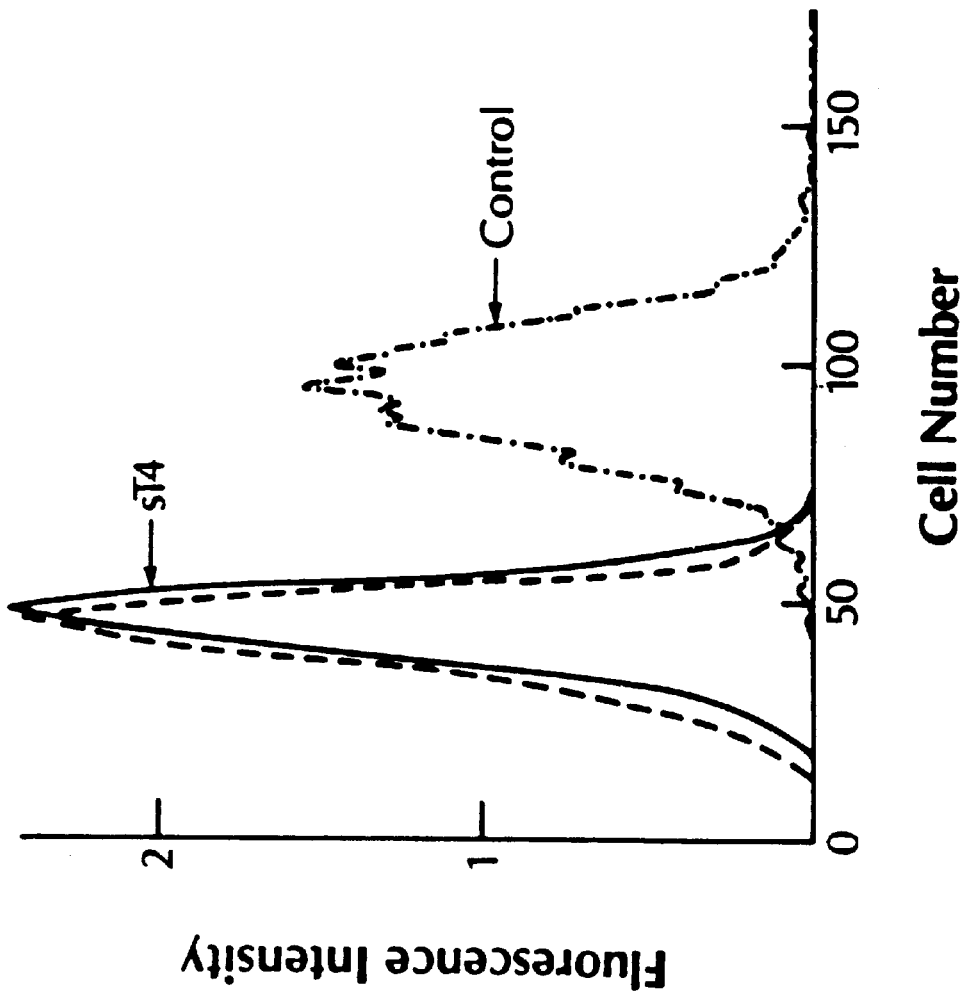

DNA ENCODING THE T CELL SURFACE PROTEIN T4 AND USE OF FRAGMENTS OF T4 IN THE TREATMENT OF AIDS

This application is a continuation of U.S. Ser. No. 08/354,452, filed Dec. 12, 1994, U.S. Pat. No. 5,958,678, which is a continuation of U.S. Ser. No. 07/909,021, filed Jul. 6, 1992, now abandoned, which is a continuation-in-part of U.S. Ser. No. 07/713,564, filed Jun. 11, 1991, now abandoned, which is a continuation of U.S. Ser. No. 06/898,587, filed Aug. 21, 1986, now abandoned.

BACKGROUND OF THE INVENTION

Within this application several publications are referenced by Arabic numerals within parentheses. Full citations for these references may be found at the end of the specification immediately preceding the claims. The disclosures of these publications in their entirety are hereby incorporated by reference into this application in order to more fully describe the state of the art to which this invention pertains.

The different functional classes of T lymphocytes recognize antigen on the surface of distinct populations of target cells. Helper T cells interact largely with macrophages and B cells; cytotoxic T cells interact with a broader range of antigen-bearing target cells. These cellular recognition events are likely to be mediated by the specific association of surface molecules on both effector and target cells. The surface of T cells is characterized by a number of polymorphic, as well as nonpolymorphic, proteins which are restricted for the most part to T lymphocytes. Although most of these molecules are common to all T cells, two classes of surface proteins consistently differ on the different functional classes of T cells, and these proteins have been implicated in T cell-target cell interactions.

One class of surface molecules distinguishes the major functional subsets of T lymphocytes: the surface glycoproteins T4 and T8. Early in thymic development, the glycoproteins T4 and T8 are coexpressed on the surface of thymocytes (1). In the peripheral immune system, the T4 and T8 molecules are expressed on mutually exclusive subsets of T cells and are only rarely expressed on the same cell (2, 3). The T4 molecule is expressed on T cells that interact with targets bearing class II major histocompatibility complex (MHC) molecules, whereas T8-bearing T cells interact with targets expressing class I MHC proteins (4, 5, 6, 7, 8, 9). The T4 population of T lymphocytes contains helper cells, whereas the T8 population contains the majority of cytotoxic and suppressor cells (6, 10). However, rare T4+ T cells can function as cytotoxic or supressor cells (6, 10), suggesting that the expression of T4 or T8 is more stringently associated with MHC class recognition than with effector function. The significance of these molecules in T cell-target cell interactions can be demonstrated by studies with monoclonal antibodies. Antibodies directed against specific epitopes of the T4 molecule (or the murine equivalent L3T4) inhibit antigen-induced T cell proliferation, lymphokine release and helper cell function (7, 8, 11, 12, 13). Similarly, monoclonal antibodies directed against T8 (or the murine equivalent Lyt2) inhibit cytotoxic T cell-mediated killing (14, 15). These observations, along with the fact that T4 and T8 do not reveal significant polymorphism, has led to the hypothesis that T4 and T8 recognize nonpolymorphic regions of class II and class I molecules, respectively.

A second class of proteins thought to differ on different effector T cells are the receptors that recognize antigen in association with polymorphic regions of MHC molecules (16, 17, 18). The interactions of helper T lymphocytes are largely restricted to antigen-bearing target cells expressing class II MHC proteins, whereas cytotoxic and suppressor T cells are restricted to targets bearing class I MHC molecules (4, 5, 6, 7, 8, 9). These specific interactions may be mediated by the T cell receptor (or receptors) that recognize antigen in the context of specific MHC molecules (17, 18). Thus, the T lymphocyte may have two independent receptors capable of recognizing both constant and polymorphic determinants of MHC proteins, and these receptors may be responsible for specific targeting of functionally distinct populations of T cells.

The human acquired immune deficiency syndrome (AIDS) is characterized by a depletion of T4+ lymphocytes. As a consequence, T cell-mediated immunity is impaired in AIDS patients, resulting in the occurrence of severe opportunistic infections and unusual neoplasms. AIDS results from the infection of T lymphocytes with a collection of closely related retroviruses (LAV, HTLV-III, or ARV), now termed human immunodeficiency virus (HIV). The range of infectivity of these agents is restricted to cells expressing the T4 glycoprotein on their surface.

Therefore, the T4 glycoprotein may serve not only as a receptor for molecules on the surface of target cells, but also as a receptor for the AIDS virus. Monoclonal antibodies directed against T4 block AIDS virus infection of T4+ cells in vitro. Furthermore, recent studies have demonstrated that when T4+ T lymphocytes are exposed to AIDS virus, the 110 kd envelope glycoprotein of the virus is associated with the T4 molecule on the host cell. The lymphotropic character of the virus could therefore be explained by the restricted expression of its receptor, T4, in subpopulations of T lymphocytes.

The depletion of T4+ T lymphocytes in AIDS results in the impairment of the cellular immune response. In addition, AIDS is frequently accompanied by central nervous system (CNS) dysfunction, most often the consequence of a subacute encephalitis. AIDS virus RNA and DNA has been identified in affected brains, and virus has been isolated from both brain and cerebrospinal fluid from patients with neurological disorders. These observations suggest that the AIDS; virus infects brain cells and is directly responsible for the CNS lesions observed in AIDS patients. Thus, the AIDS virus may be neurotropic as well as lymphotropic. It is therefore important to determine whether T4 is also expressed in the CNS or whether additional brain-specific surface molecules may serve as a receptor Eor the AIDS virus.

The elucidation of the specific interactions of T4 and T8 would be facilitated by the isolation of the T4 and T8 genes, the determination of their structure, and the ability to introduce them into different cellular environments. The isolation and sequence of a cDNA encoding the T8 molecule has recently been reported (19, 20, 21). The deduced protein sequence indicates that T8 is a membrane-bound glycoprotein with an N-terminal domain that bears homology to the variable region of immunoglobulin light chains.

SUMMARY OF THE INVENTION

The present invention provides a single-stranded nucleic acid molecule which encodes an amino acid sequence comprising at least a portion of a T4 glycoprotein. Also provided is an amino acid sequence comprising at least a portion of a T4 glycoprotein. This amino acid sequence may be capable of specifically forming a complex with a human immunodeficiency virus envelope glycoprotein. In addition to its capability to specifically form a complex with a human immunodeficiency virus envelope glycoprotein, the amino acid sequence may be soluble in an aqueous solution.

The soluble amino acid sequence of the present invention may be used as a therapeutic agent, i.e. a prophylaxis, for the treatment of a subject infected with a human immunodeficiency virus. Moreover, a monoclonal antibody directed to the soluble amino acid sequence of the present invention may be useful as a vaccine for immunizing a human subject against a human immunodeficiency virus. Additionally, a monoclonal antibody directed against the soluble amino acid sequence of the present invention may be useful for preparing T4 glycoprotein anti-idiotypic antibodies. These T4 glycoprotein anti-idiotypic antibodies may be useful as a prophylaxis for treating a subject infected with a human immunodeficiency virus.

Cells ($5 \times 10^5$) where incubated with the mouse monoclonal antibodies OKT̄4B or OKT̄8, washed, and then incubated with FITC conjugated goat anti-mouse immunoglobulin. The cells were analyzed on a FACS IV Cell Sorter and plotted by a VAX 11/780 computer as cell number vs. log fluorescence. Unitransformed NIH 3T3 cells and L cells gave identical cytofluorographic tracings. Fro 2.2 is a leukemic T cell line with phenotype $T3^-$; $T4^+$; $T8^+$; $T11^+$. LTD-4, is a $T4^+$ primary L cell transformant obtained following transfer of total genomic DNA. 3A+ is an NIH 3T3 cell line that was transformed with the T4-pMV6tk/neo retroviral expression construct.

Figure 2:
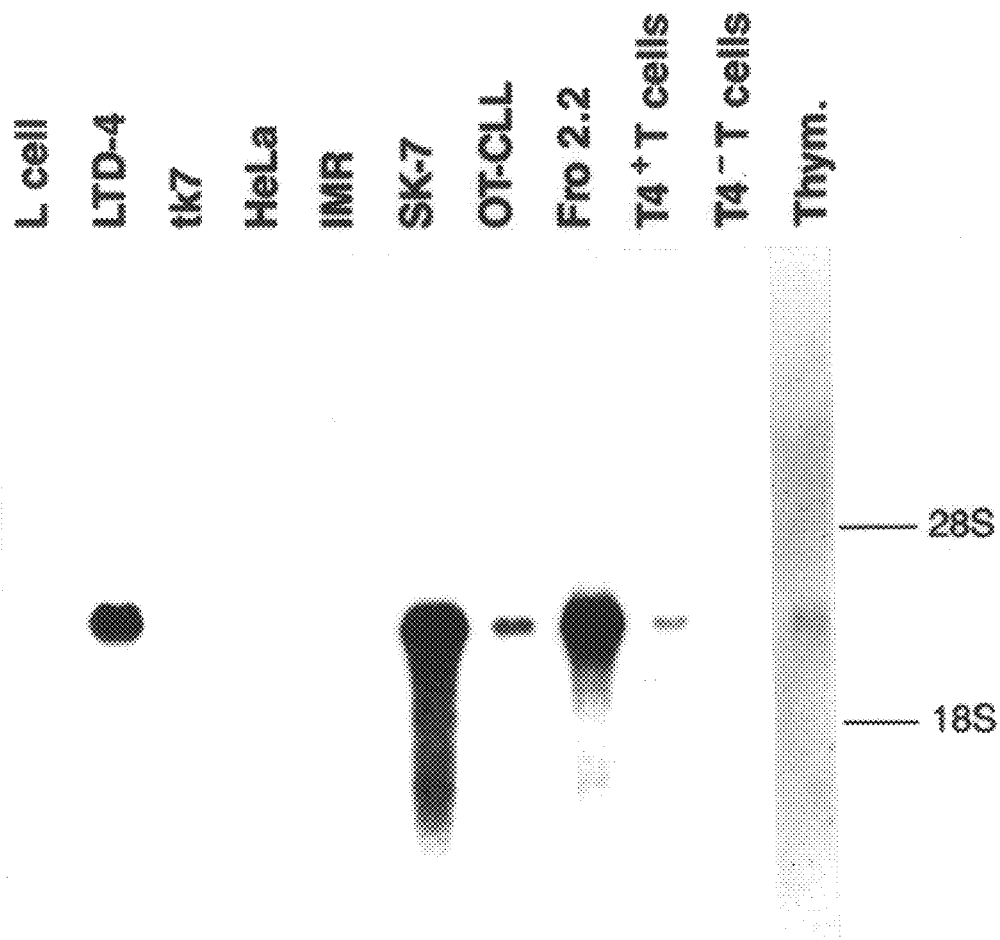

FIG. 2. Northern Blot Analysis of RNA Derived from $T4^+$ and $T4^-$L Cells and Human Cells Three micrograms of poly(A)$^+$ RNA or 12 µg of total RNA (peripheral T cells and thymocytes) were electrophoresed through a 0.8% agarose-formaldehyde gel, blotted onto GeneScreen (New England Nuclear), and probed with a $^{32}$P-labeled 0.6 kb T4 cDNA insert. $T4^+$ cells include LTD-4 ($T4^+$, $T8^-$ L cell transformant), SK-7 T cell hybridoma ($T4^+$, $T8^-$), OT-CLL leukemia ($T4^+$, $T8^-$), Fro 2.2 leukemia ($T4^+$, $T8^-$), T4-enriched peripheral T lymphocytes, and human thymocytes. $T4^-$ cells include untransformed cells, tk7 ($T8^+$ L cell transformant), HeLa cells, human neuroblastoma cells (IMR), and T8-enriched peripheral T lymphocytes. The human thymocyte lane was exposed four times longer and photographed on high contrast film.

Figure 3A:
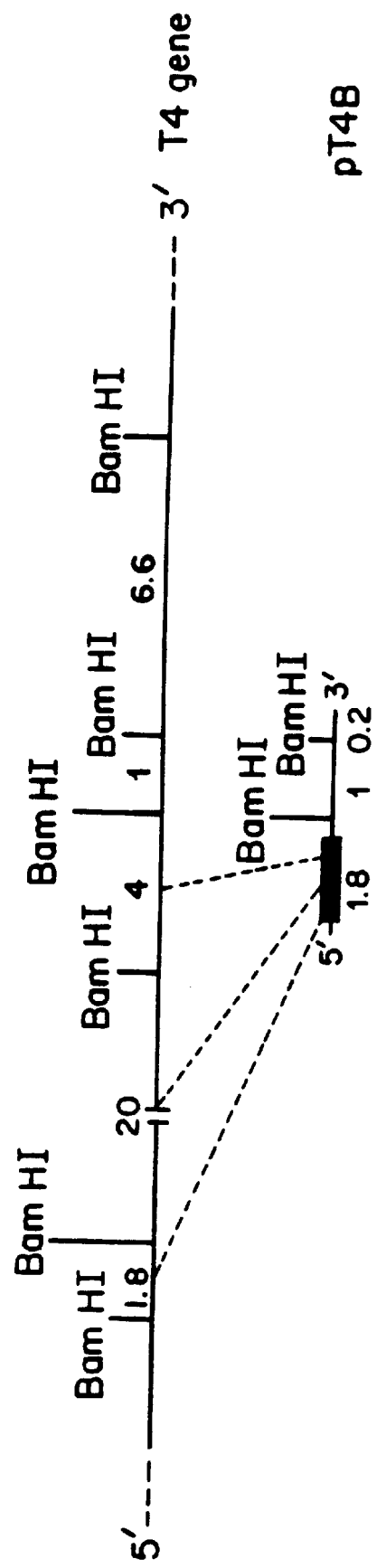
Figure 3B:
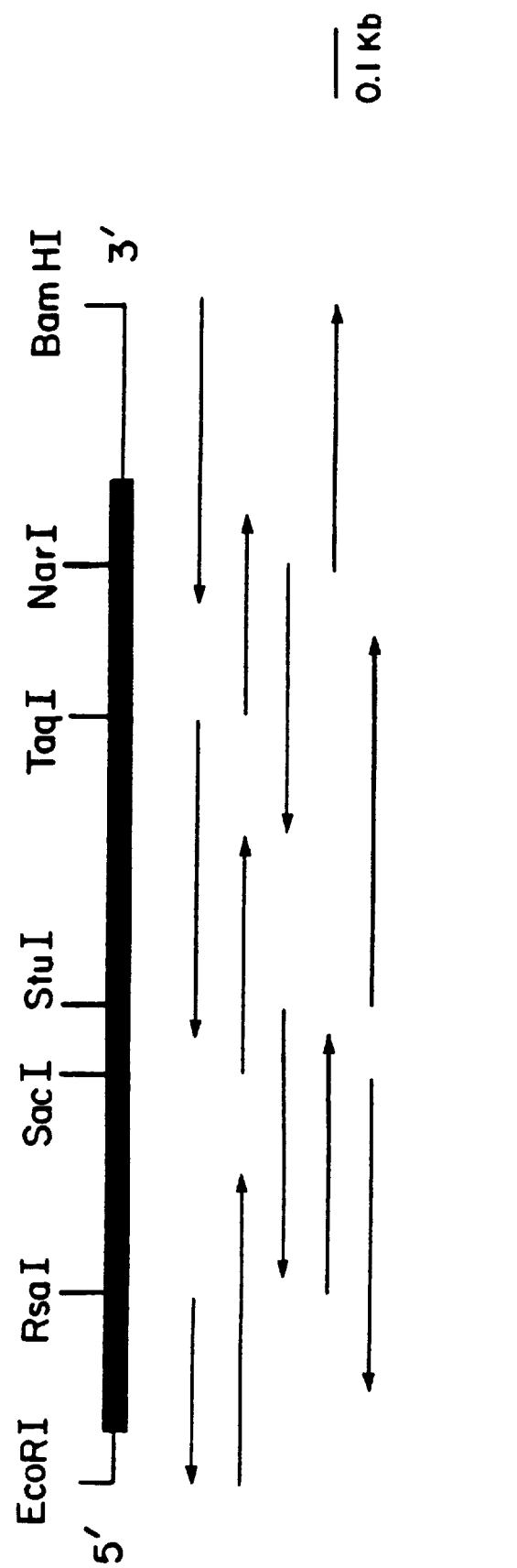
Figures 2, 3C:
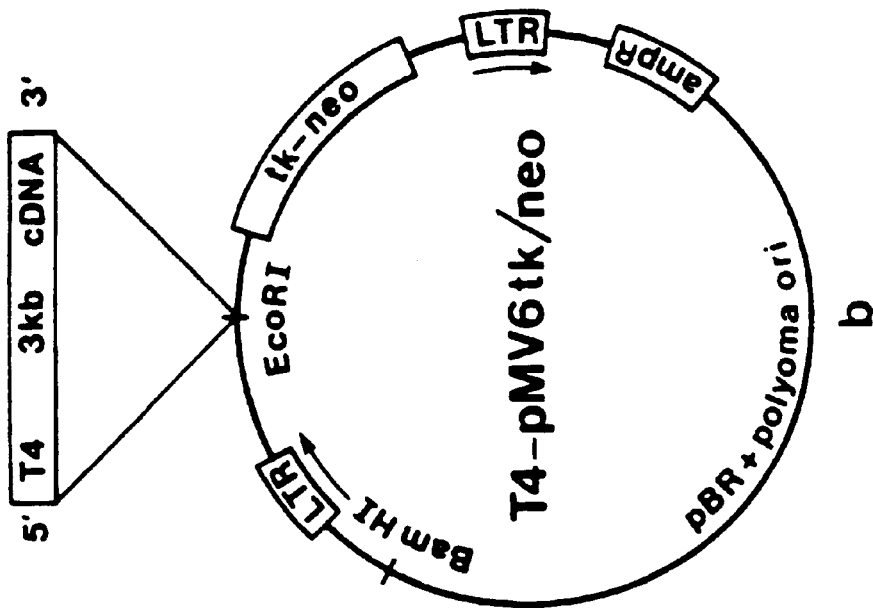
Figures 1, 3C:
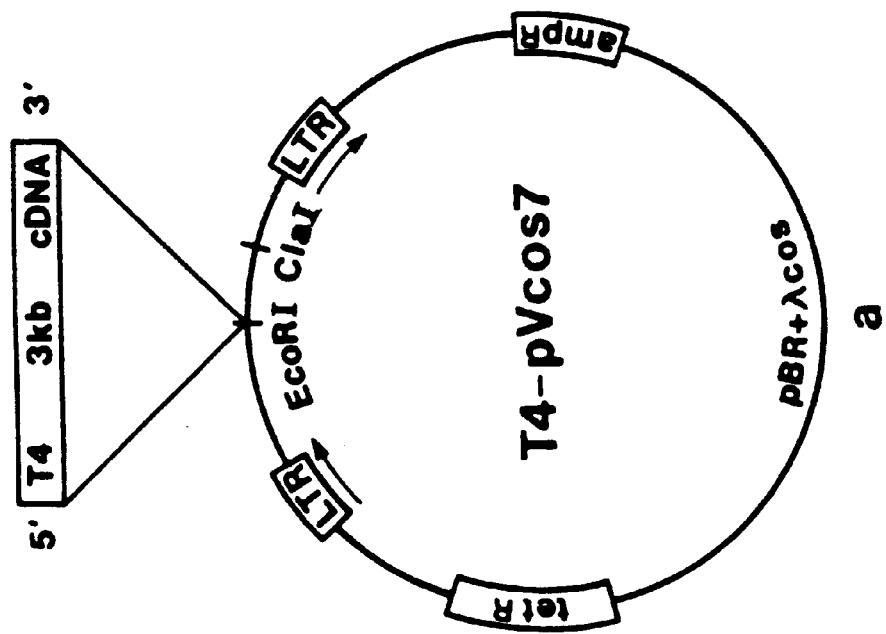

FIGS. 3A–3C. Restriction Nuclease Maps; of pT4B and the T4 Gene, Sequencing Strategy, and Recombinant Vectors A. Alignment of the Bam HI restriction fragments of pT4B cDNA and the T4 gene. The order of Bam HI fragments in the T4 gene was determined by Southern blot analysis and genomic clone mapping. The alignment of the 5' end of pT4B and the T4 gene is shown by dotted lines, and the shaded region in pT4B corresponds to the coding sequence. The indicated sizes are in kilobases.

B. Sequencing strategy. Arrows indicate length of sequence determined by subcloning fragments into M13 and sequencing by the dideoxy termination procedure (36).

C-1 and C-2. Eukaryotic expression vectors. These constructs contain two Moloney murine leukemia virus long terminal repeats (LTRs) whose orientations are indicated by arrows. The pT4B cDNA was subcloned into the Eco RI site of each vector in the orientation indicated. (C-1) The T4-pVcos7 construct. (C-2) The T4-pMV6tk/neo construct contains the neomycin phosphotransferase gene fused to the HSV thymidine kinase promoter.

Figure 4:
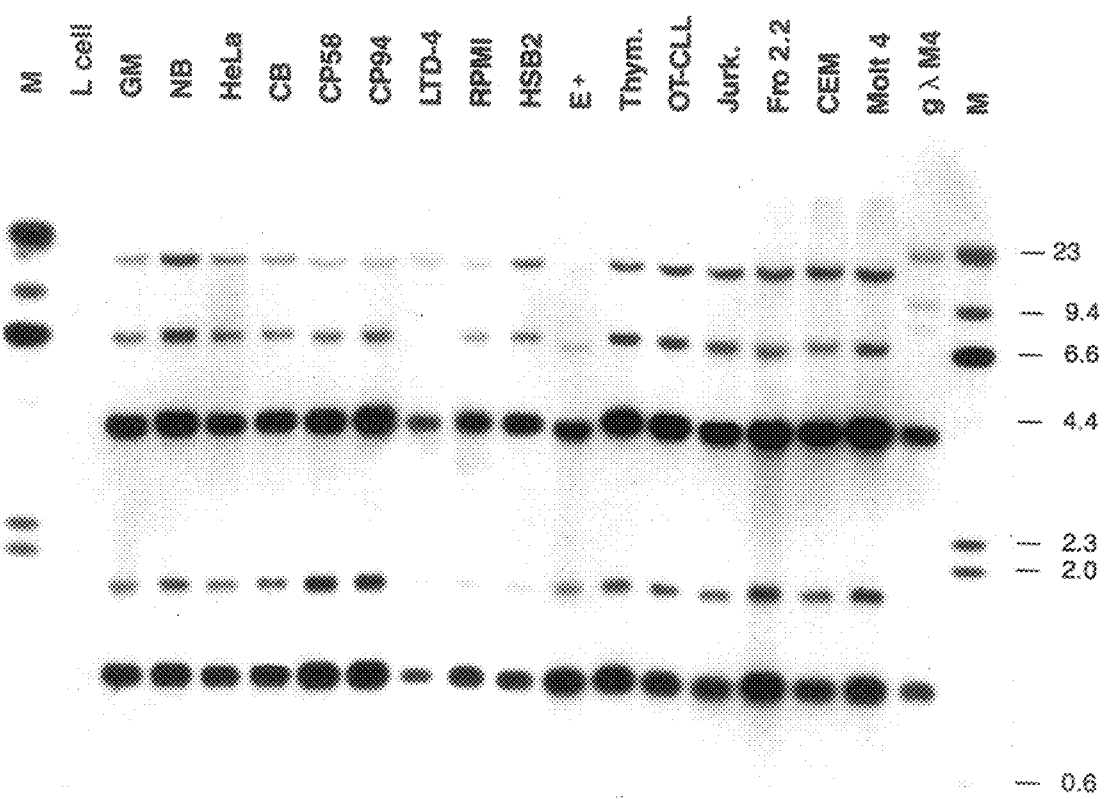

FIG. 4. Southern Blot Analysis of DNA from Untransformed and $T4^+$ L Cells and T, B, and Nonlymphoid Human Cells Ten micrograms of cellular DNAs were digested with Bam HI, electrophoresed through a 0.8% agarose gel, blotted onto GeneScreen, and probed with a nick-translated pT4B cDNA insert. The indicated size markers are in kilobases. Hybridizing bands of sizes 20 kb, 6.6 kb, 4 kb, 1.8 kb, and 1 kb appear in all human DNAS. DNAs from $T4^-$, nonlymphoid origin include untransformed L cells, human fibroblasts (GM), human neuroblastoma cells (NB), and HeLa cells. CB, CP58, and CP94 are DNAs derived from EBV-transformed human B cell Lines. LTD-4 is the $T4^+$ primary L cell transformant. RPMI and HSB2 are $T4^-$ human T cell leukemic lines; $E^+$ cells and thymocytes (Thym.) contain $T4^+$ T cells. OT-CLL, Jurkat (Jurk.), Fro 2.2, CEM, and Molt 4 are $T4^+$ T cells. gλM4 is a genomic clone which contains sequences spanning the 3' end of the T4 gene.

Figure 5:
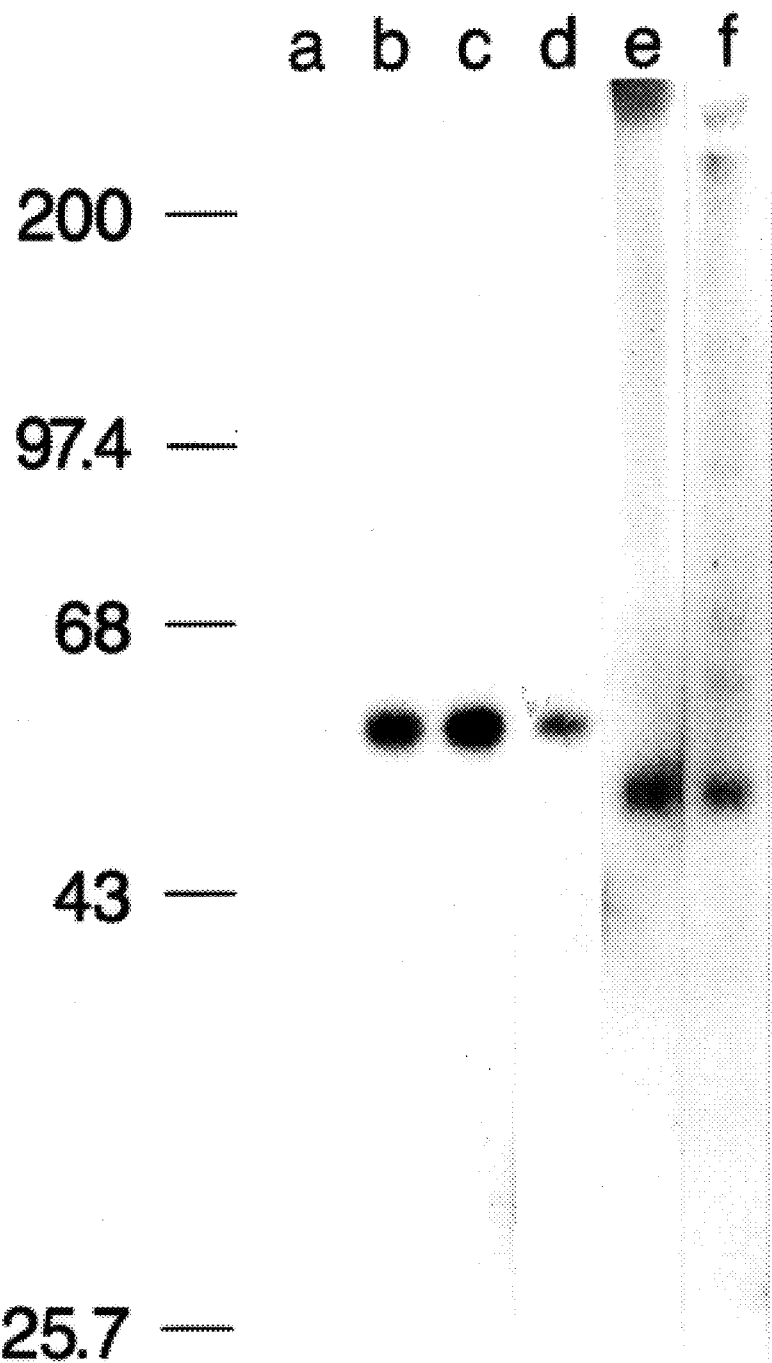

FIG. 5. Immunoprecipitation of the T4 Glycoprotein from NIH 3T3 Cells Transformed with the Retroviral Expression Constructs L-[$^{35}$S]-methionine labeled proteins from two independent NIH 3T3 transformants, peripheral T lymphocytes, and untransformed 3T3 cells were subjected to lentil lectin chromatography to enrich for glycoproteins. $2.5 \times 10^6$ cpm of each sample was precleared and then immunoprecipitated with OKT̄4 monoclonal antibodies and Protein A-Sepharose. The beads were washed, dissolved in sample buffer, and electrophoresed through a 10% SDS-polyacrylamide gel under reducing (lanes a–d) and nonreducing (lanes e and f) conditions. Lane a, untransformed NIH 3T3 cells. Lane b, T4C2, an NIH 3T3 cell transformed with the T4-pVcos7 construct. Lanes c and e, 3A+, an NIH 3T3 cell transformed with the T4-pMV6tk/neo construct. Lanes d and f, peripheral human T lymphocytes. Relative molecular masses ($M_r$) are given in kilodaltons.

Figure 6B:
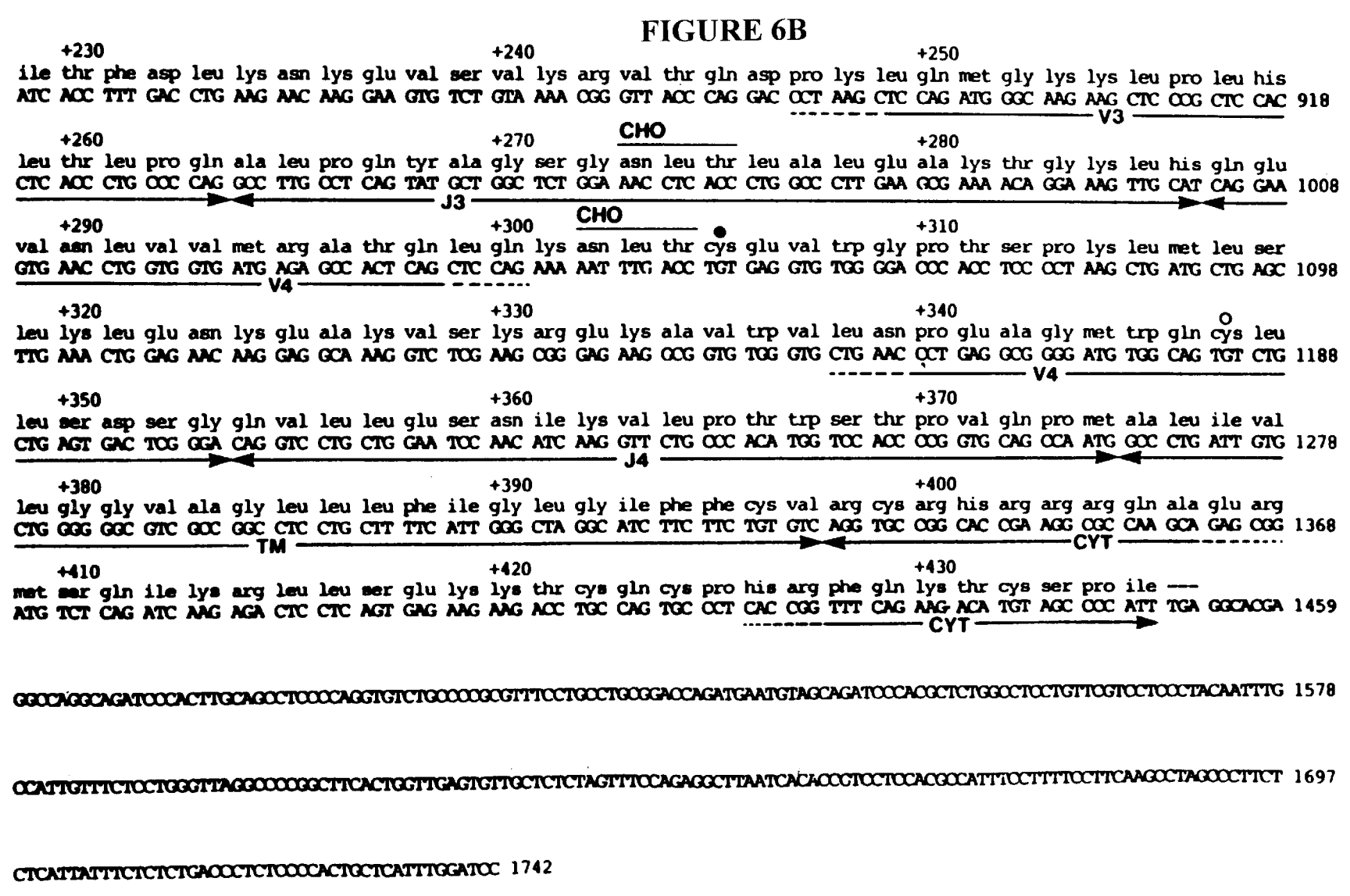

FIGS. 6A–6B. Nucleotide Sequence of the T4 cDNA and Translated Sequence of the T4 Protein The nucleotide and predicted amino acid sequences (SEQ ID NO:34) of the cDNA clone pT4B obtained according to the sequencing strategy outlined in FIG. 3B. Numbers shown above the amino acid sequence designate amino acid residue positions. The numbers on the right show nucleotide positions. All extracellular cysteines are marked by (●) or (○). The leader sequence (L), variable-like (V), joining-like (J), transmembrane (TM), and cytoplasmic (CYT) regions are indicated by horizontal arrows below the sequence, although the exact boundaries are ambiguous. Two potential N-linked glycosylation sites (Asn-Leu-Thr) are also indicated (CHO).

Figure 7:
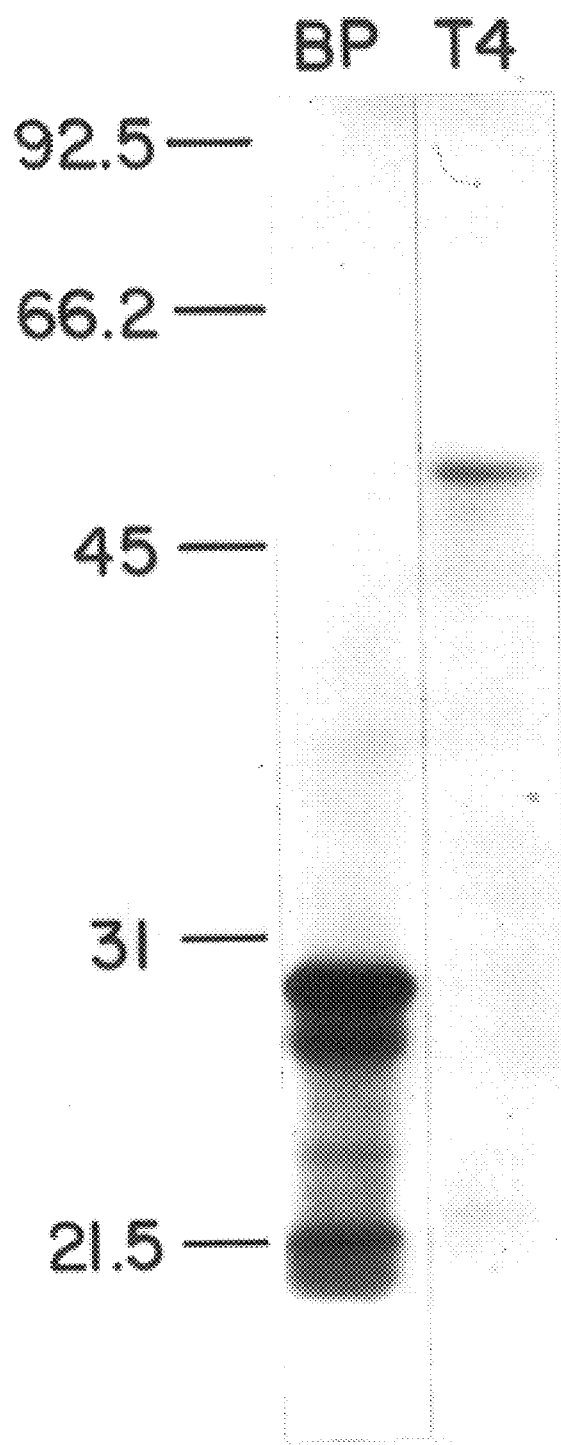

FIG. 7. In Vitro Translation RNA derived from SP6 Transcription

The full length T4 cDNA insert was subcloned into the RNA expression vector pSP65 (Promega Biotec). Linearized plasmid DNA was transcribed with SP6 polymerase (40), and RNA was translated in a wheat germ system (Bethesda Research Laboratories) containing L-[$^{35}$S]-methionine. The in vitro translation products were subjected to electrophoresis through a 10% SDS-polyacrylamide gel (lane T4). Bovine pituitary RNA (BP) was used as a control. Relative molecular masses ($M_r$) are given in kilodaltons.

Figure 8:
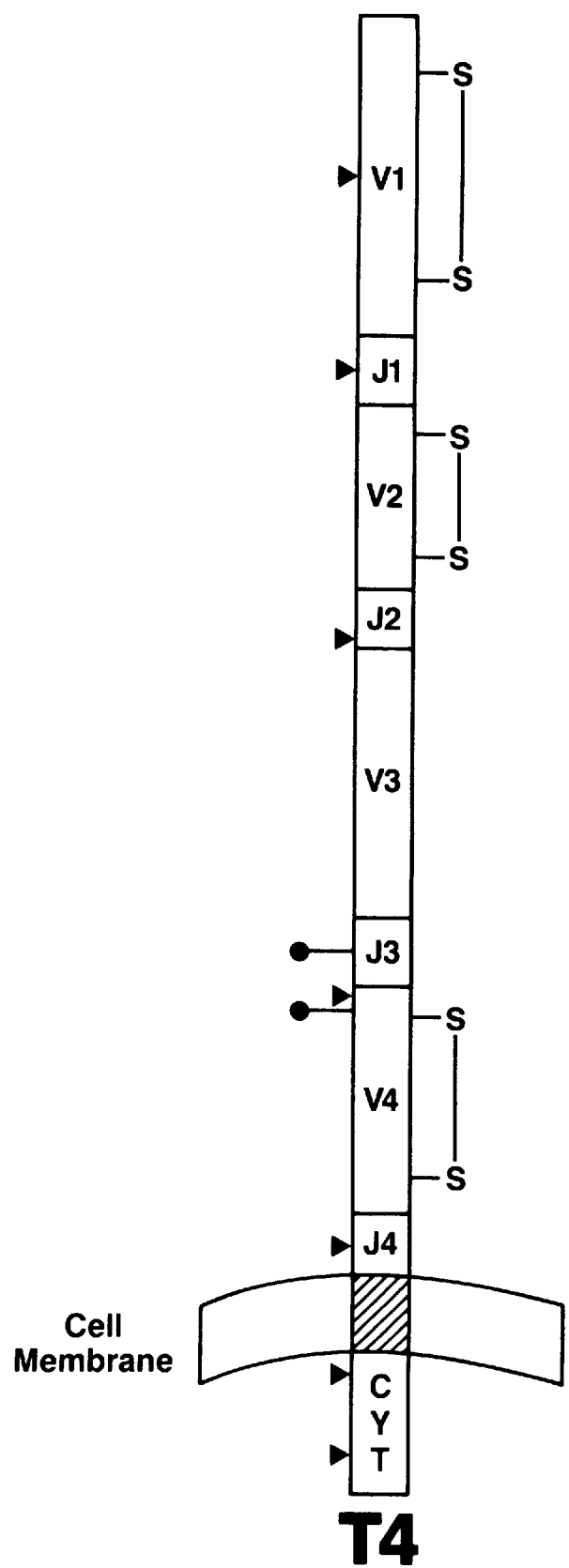

FIG. 8: Schematic Diagram of the T4 Glycoprotein Spanning the Cell Membrane

T4 consists of four tandem VJ-like domains ($V_1J_1-V_4J_4$), a hydrophobic membrane-spanning segment (shaded area), and a charged cytoplasmic region (CYT). Two potential N-linked glycosylation sites in the extracellular portion are indicated ●—. The positions of introns 2–8 in the T4 gene are also marked (▲).

Figure 9A:
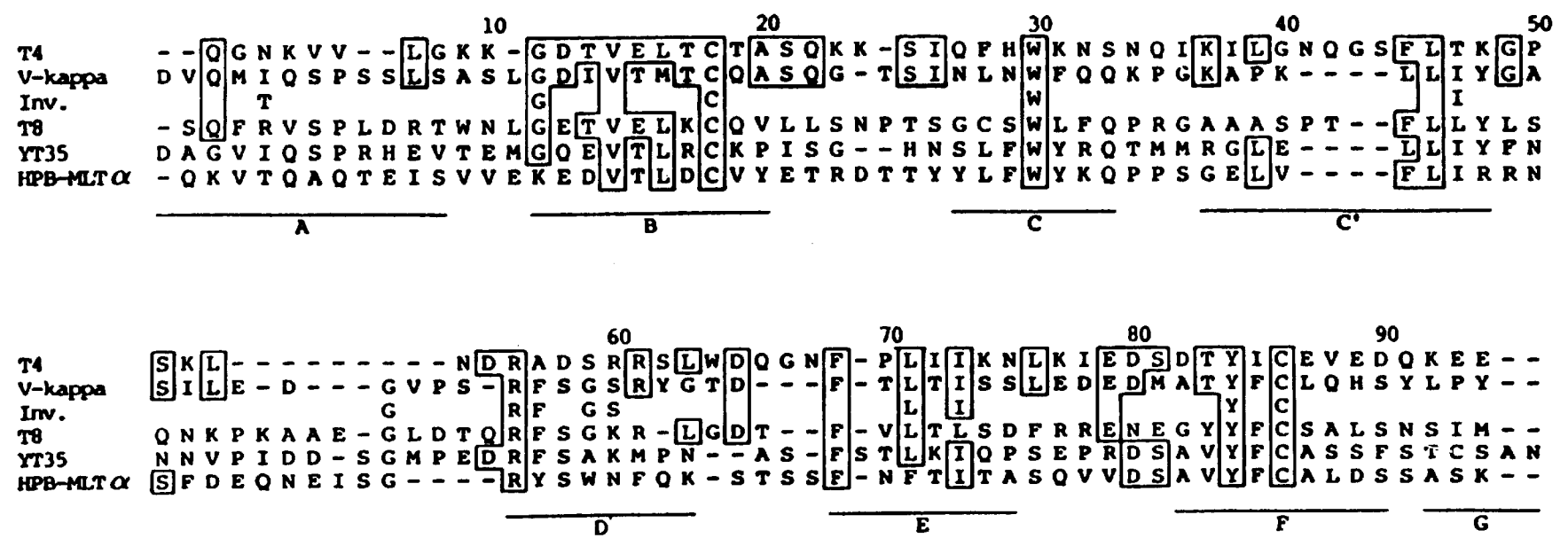

FIGS. 9A–9C. Alignment of the Variable, Joining, and Transmembrane Regions of T4 with Members of the Immunoglobulin Gene Family A. Alignment of the variable region amino acid sequence of T4 SEQ ID NO:5 with a mouse kappa SEQ ID NO:6 light chain immunoglobulin J606 (66), T8 (SEQ ID NO:8) (20), a human T cell antigen receptor β-chain YT35 SEQ ID NO:9 (97), and a human T cell antigen receptor α-chain HPB-MLT SEQ ID NO:10 α(98). The invariant residues in the light chain variable region are included (Inv.) (SEQ ID NO:7) in the alignment. The alignment was performed in order to maximize identities and structural homologies with T4, which appear as boxed residues. The lines below the sequence with letters A, B, C, C', D, E, F, and G indicate the residues which form β-strands (67). β-strand G continues into the J sequence.

B. Alignment of the joining region amino acid sequence of T4 with the consensus J sequences of the T cell antigen receptor β-chain, immunoglobulin lambda and kappa light chains, and the J sequence of the human T cell receptor α-chain (SEQ ID NOS:11–15) (99).

C. Alignment of the transmembrane regions of T4 and an MHC class II β-chain (100). The putative transmembrane domain (TM) is indicated below the sequence (SEQ ID NO.16–17).

Figure 10:
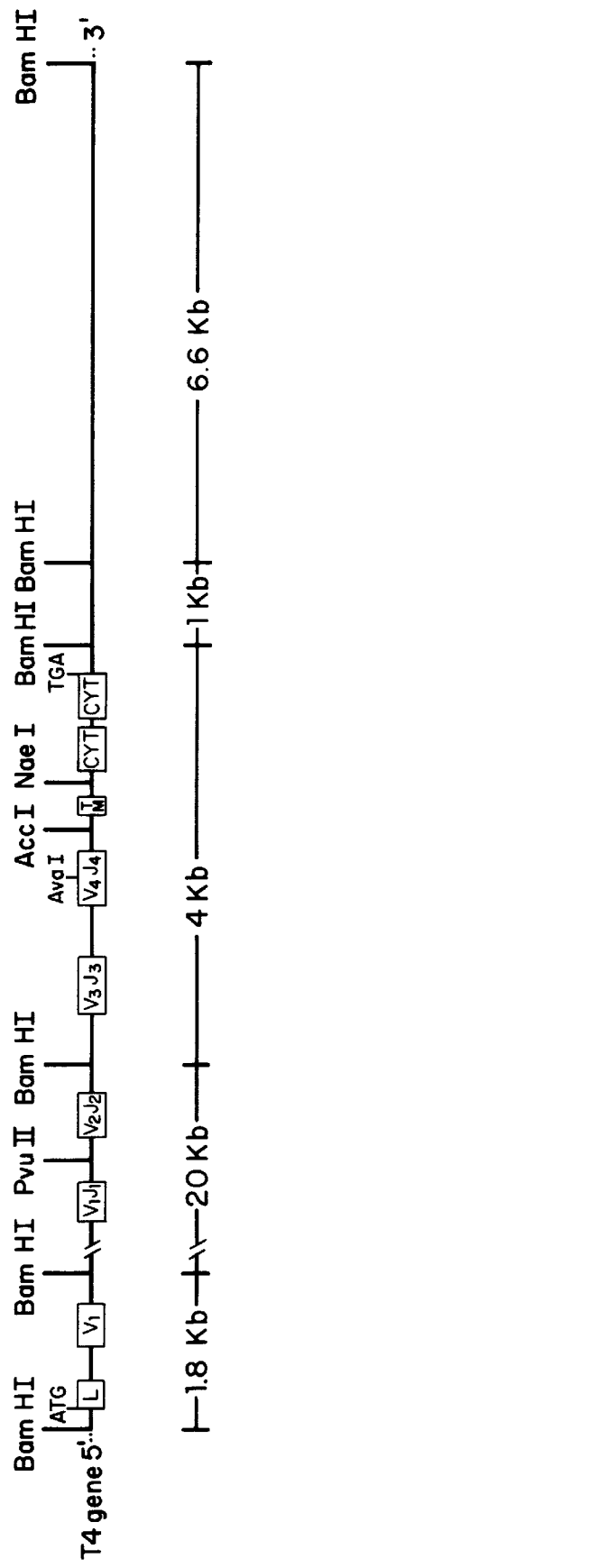

FIG. 10. Restriction Nuclease Map of the T4 Gene in Human Chromosomal DNA

The positions of the 9 exons were determined by genomic clone mapping, Southern blot analysis, and nucleotide sequencing. The leader sequence (L), variable-like (V), joining-like (J), transmembrane (TM), and cytoplasmic (CYT) regions are boxed. The position of the methionine codon surrounded by the intitiation consensus sequence is indicated (ATG) at the beginning of the leader exon (L); the termination codon TGA is shown at the end of the second cytoplasmic exon (CYT). The indicated sizes are in kilobases.

Figures 2, 11A:
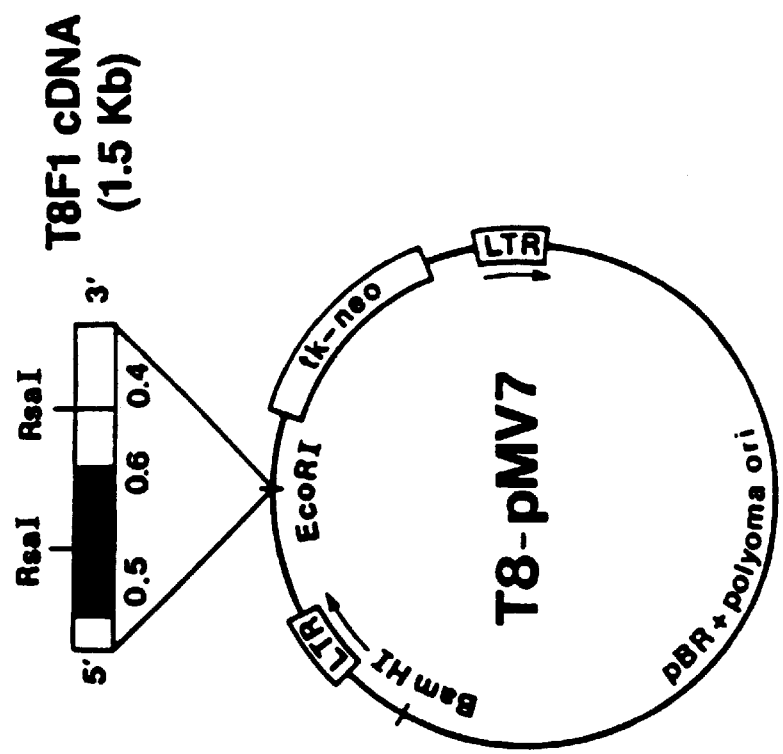
Figures 1, 11A:
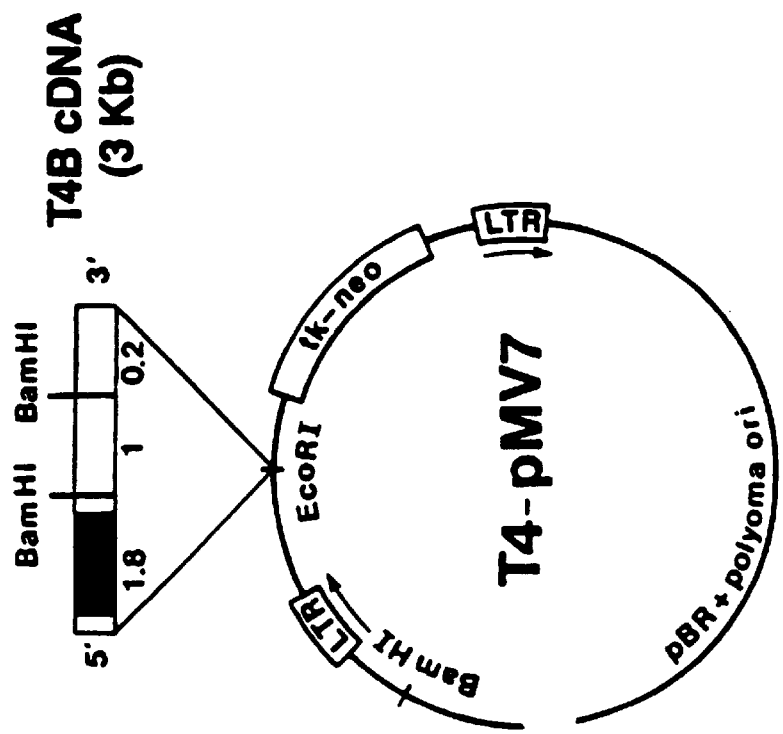
Figure 11B:
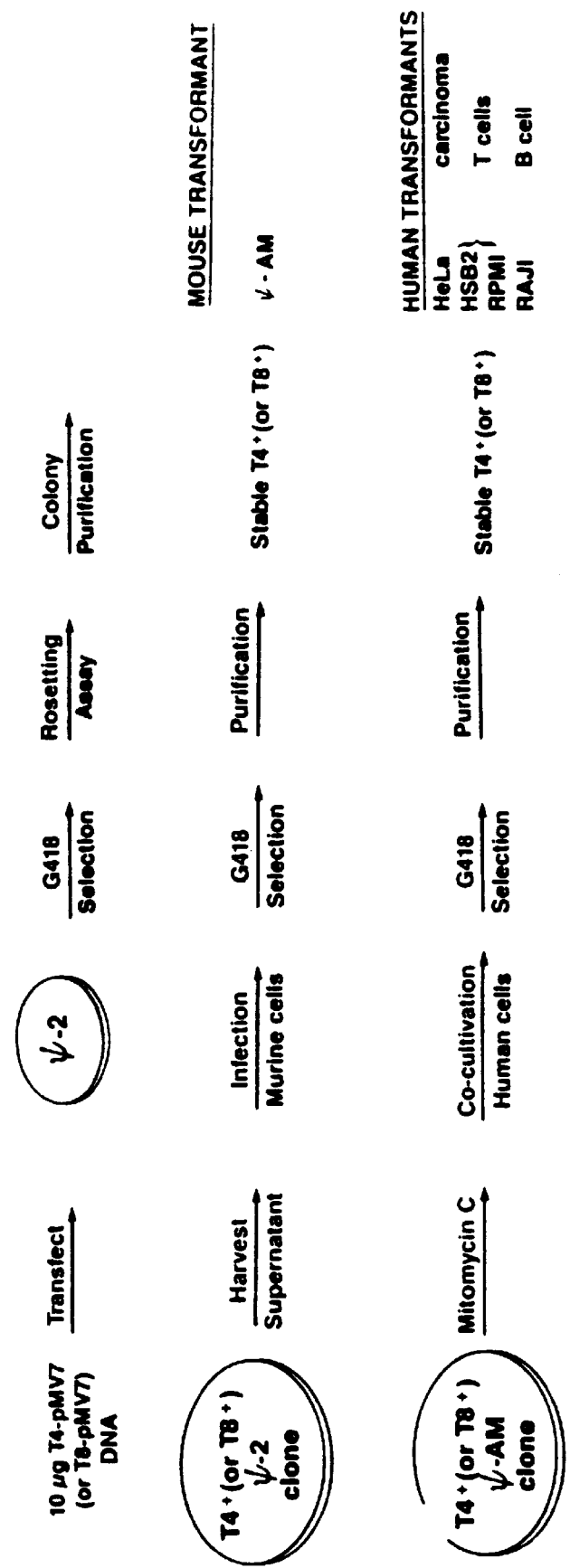

FIGS. 11A–11B. Recombinant Retroviral Expression Vectors and Construction of Transformed Cells A-1 and A-2. Recombinant retroviral expression vectors. pMV7 contains two directly repeated Moloney murine sarcoma virus long terminal repeats (LTRS) in the orientation indicated by arrows. pMV7 also contains the bacterial neomycin phosphotransferase gene (neo) fused to the HSV thymidine kinase promoter (tk). Full length cDNA inserts encoding T4 (T4B) (70) or T8 (T8F1) (20) were subcloned into the Eco RI site in the orientation indicated by arrows, generating T4-pMV7 and T8-pMV7, respectively. The coding sequences are shown as shaded regions. The indicated sizes are in kilobases.

B. Retrovirus-Mediated Gene Transfer Strategy.

Figure 12:
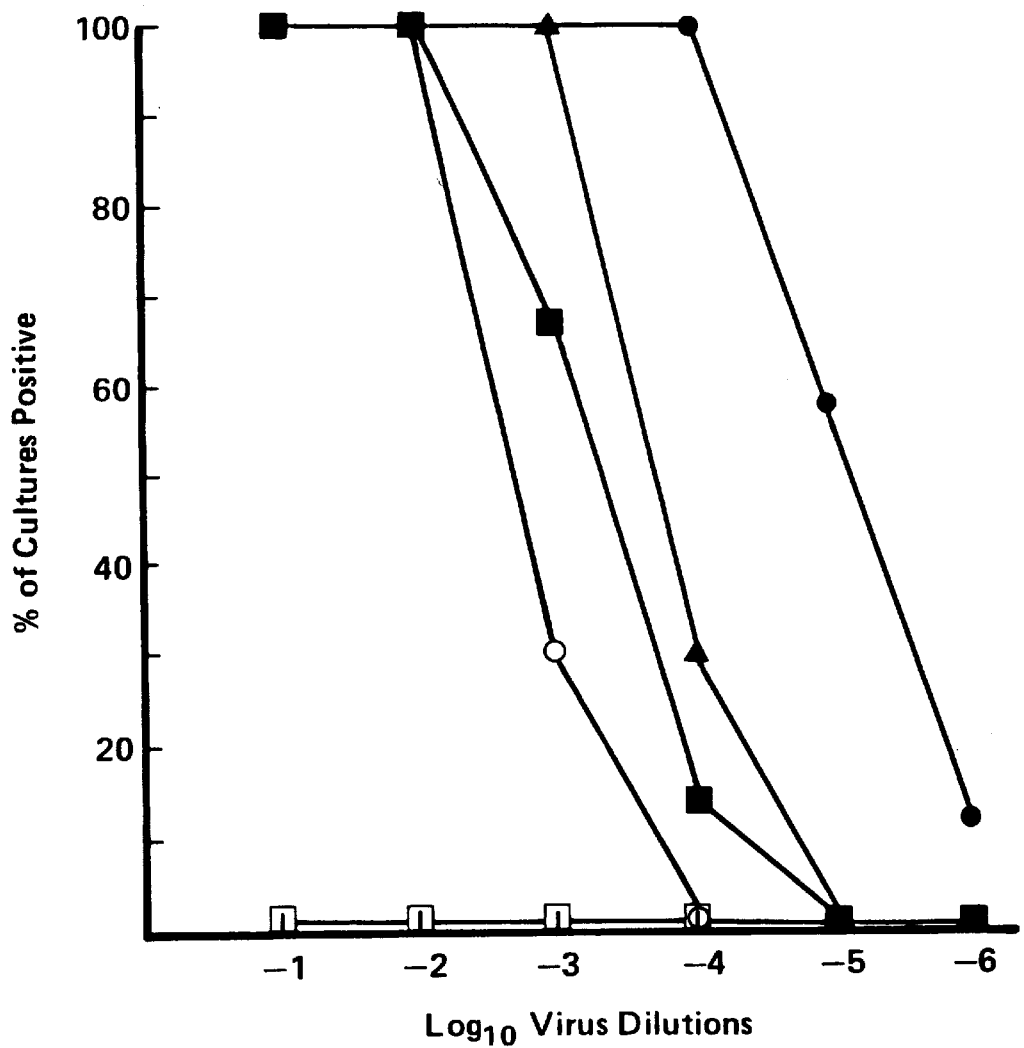

FIG. 12. The Efficiency of Infection of Naturally-Isolated and Transformed T4$^+$ Cells Cells were inoculated with serial 10-fold dilutions of AIDS virus, incubated for 18 hours at 37° C., washed, and plated in microculture. The frequency of infected cultures was determined by an enzyme-linked immunoabsorbent assay (ELISA) 12 days post-infection (46). The results were plotted as % positive cultures vs. log virus dilution. Infectious virus titer (ID-50) is defined as the reciprocal of the dilution at which 50% of the cultures are positive for virus (47). Naturally isolated T4$^+$ cells include phytohemagglutinin (PHA)-stimulated normal peripheral lymphocytes ●—● and the T cell line CEM ○—○. T4$^+$ transfected cell lines include HSB2-T4$^+$ T cells ▲—▲ and Raji-T4$^+$ B cells ■—■. The T8$^+$ transfected cell lines HSB2-T8$^+$ and Raji-T8$^+$ □—□ served as controls in these studies.

Figure 13A:
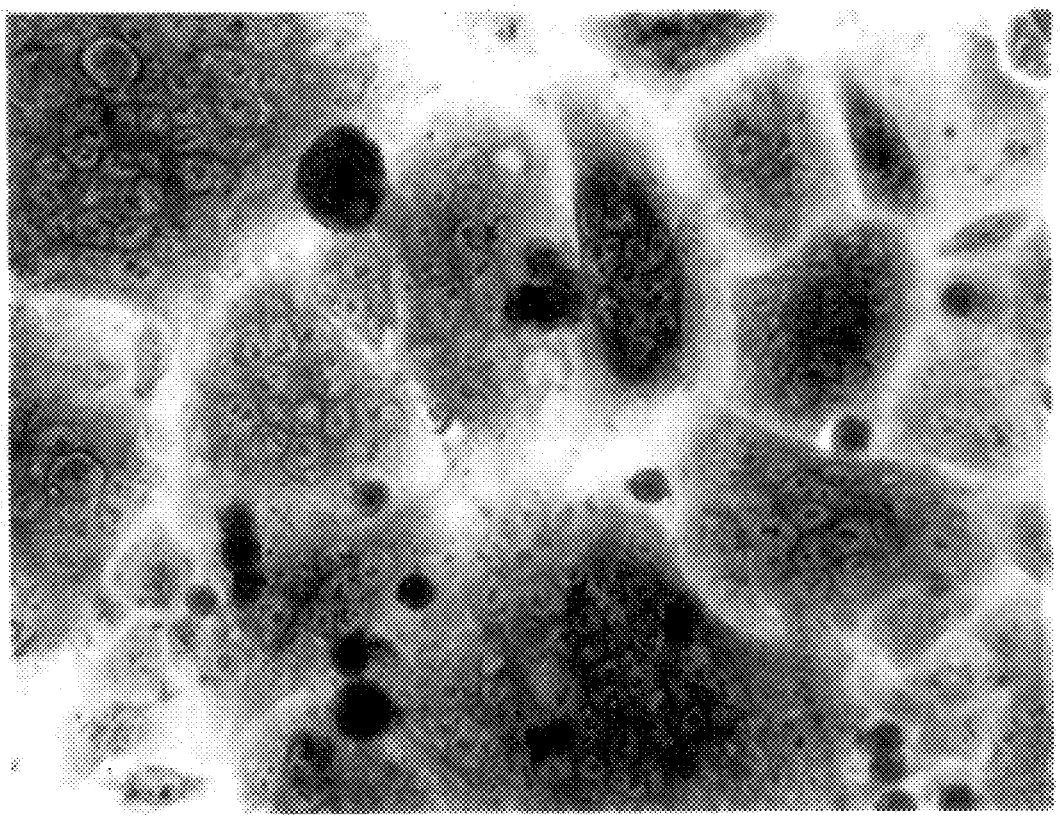
Figure 13B:
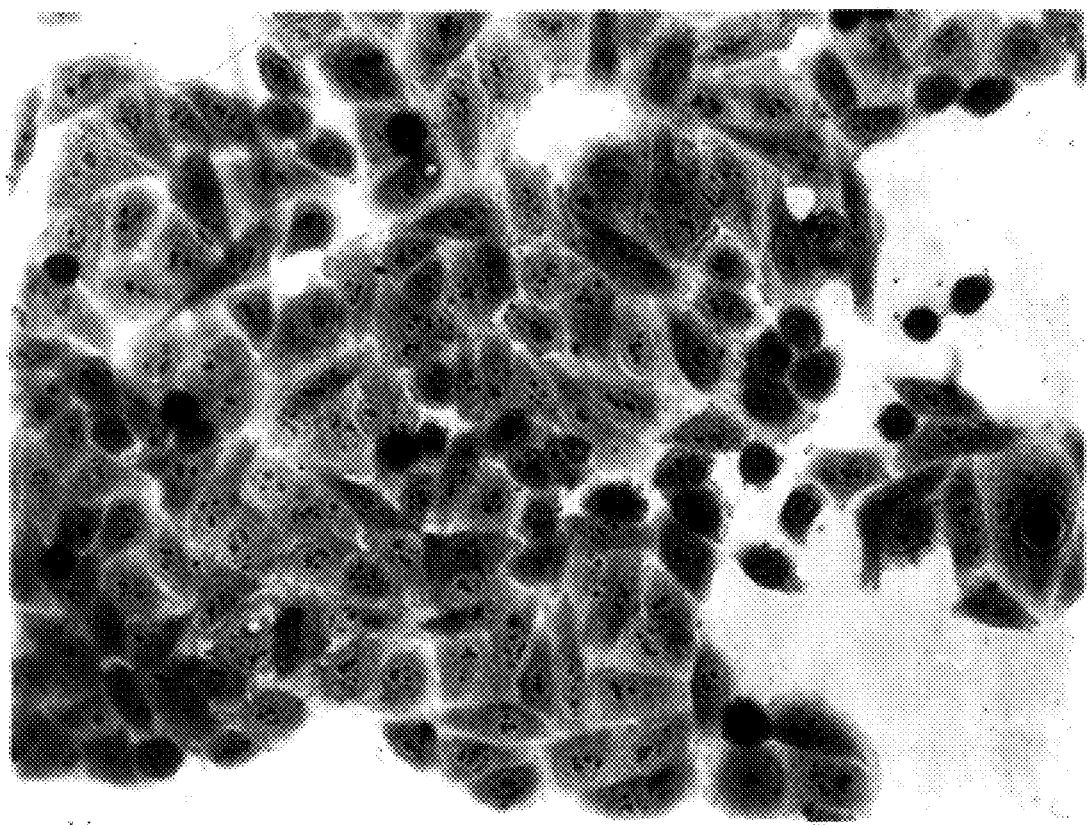

FIGS. 13A–13B. Formation of Syncythia in T4$^+$ HeLa Tranformants

A. $2 \times 10^5$ monolayer HeLa-T4$^+$ tranformants were mixed with $2 \times 10^4$ AIDS virus-producing H9 cells and incubated at 37° C. Inspection of the cultures after 18 hours revealed that over 90% of nuclei in the monolayer sheet were contained within syncytia.

B. Anti-T4A monoclonal antibody (1:20) was added to the mixed cultures at the time of seeding. Inspection of the cultures after 18 hours revealed a complete absence of cell fusion.

Cultures were photographed at 160×magnification.

Figures 1, 14A:
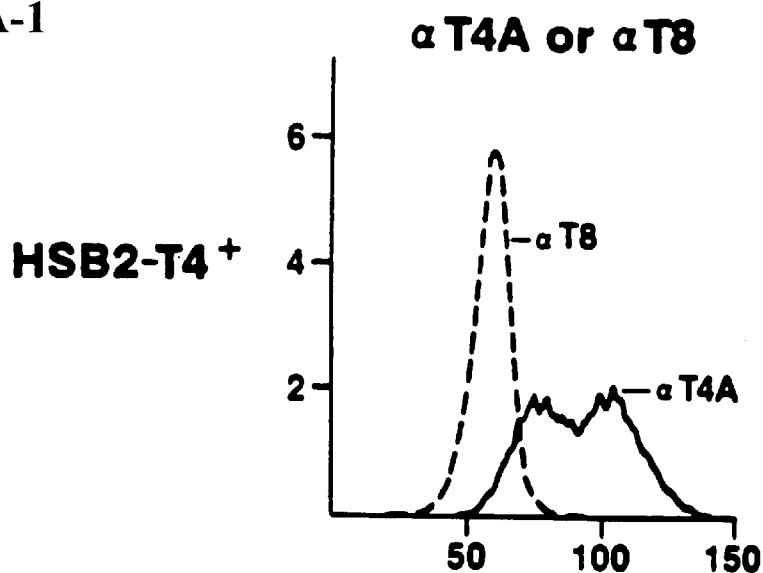
Figures 2, 14A:
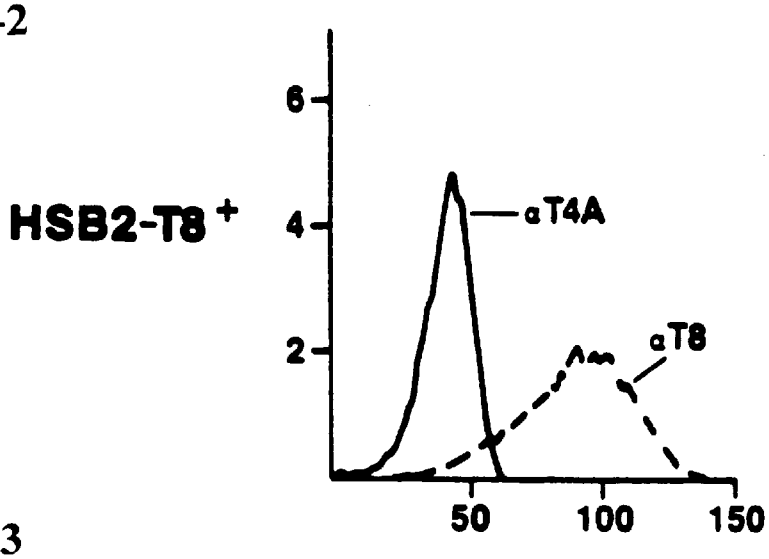
Figures 3, 14A:
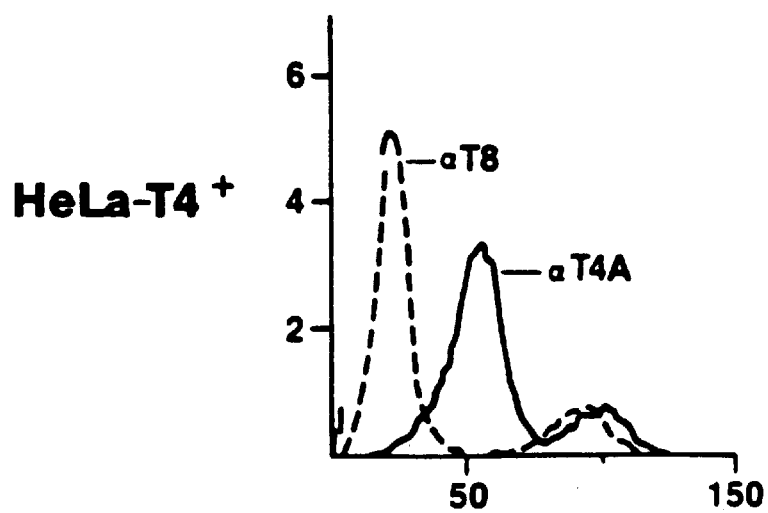
Figures 1, 14B:
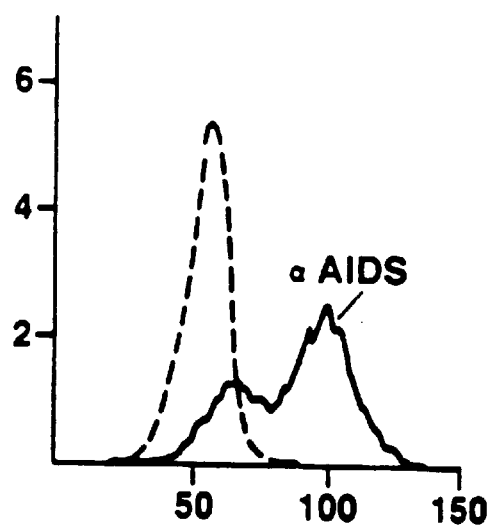
Figures 2, 14B:
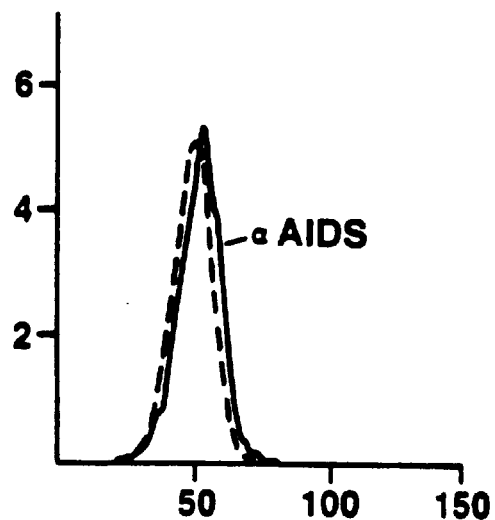
Figures 3, 14B:
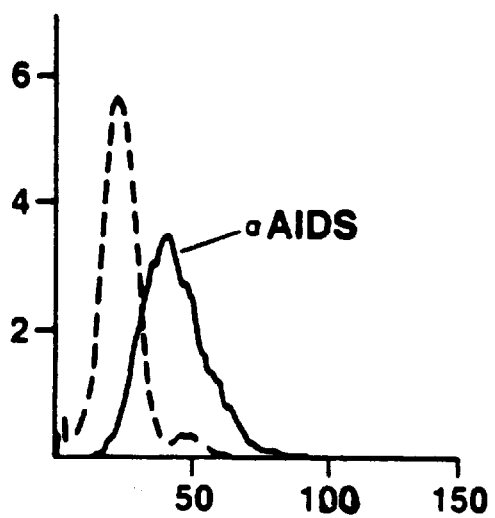
Figures 1, 14C:
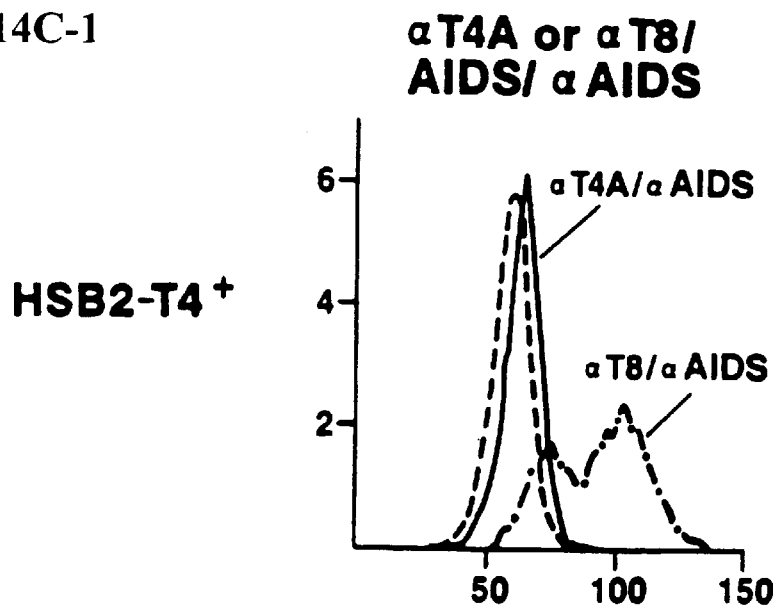
Figures 2, 14C:
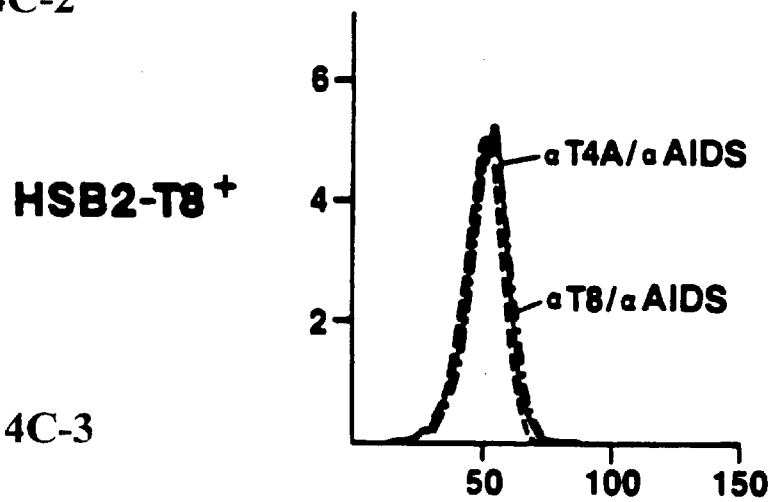
Figures 3, 14C:
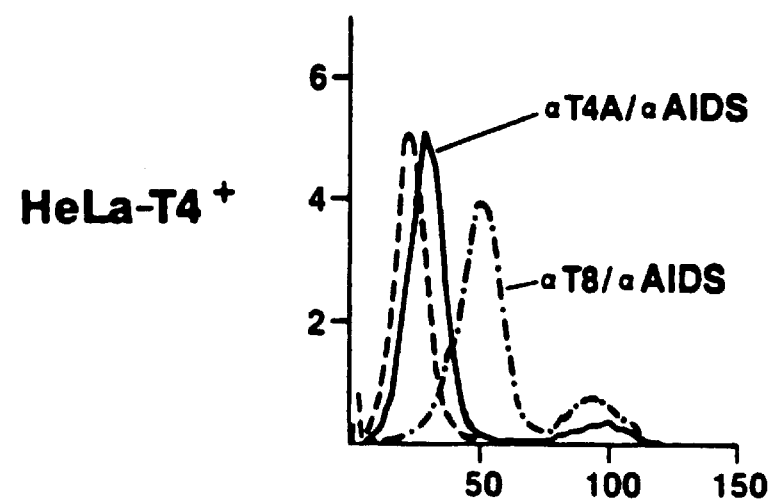

FIGS. 14A–14C. Flow Cytometry Analysis of AIDS Virus Binding to T4$^+$ Transformed Cells 14A-1–14A-3. Cells ($5 \times 10^5$) were incubated with fluorescein-conjugated anti-T4A (—) or anti-T8 (---) monoclonal antibodies, washed, and analyzed by cytofluorometry.

14B-1–14B-3. Cells ($5 \times 10^5$) were incubated with buffer (---), or AIDS virus (—), washed, incubated with fluorescein-conjugated anti-AIDS virus antibody, and analyzed by cytofluorometry.

14C-1–14C-3. Cells ($5 \times 10^5$) were incubated with buffer (---), or with anti-T4A monoclonal antibody followed by AIDS virus (—), or with anti-T8 monoclonal antibody followed by AIDS virus (-●-●-). After a wash, fluorescein-conjugated anti-AIDS virus antibody was added and the cells were analyzed by cytofluorometry.

Flouorescence histograms (cell number vs. fluorescence intensity) of each cell line are arranged horizontally.

Figure 15A:
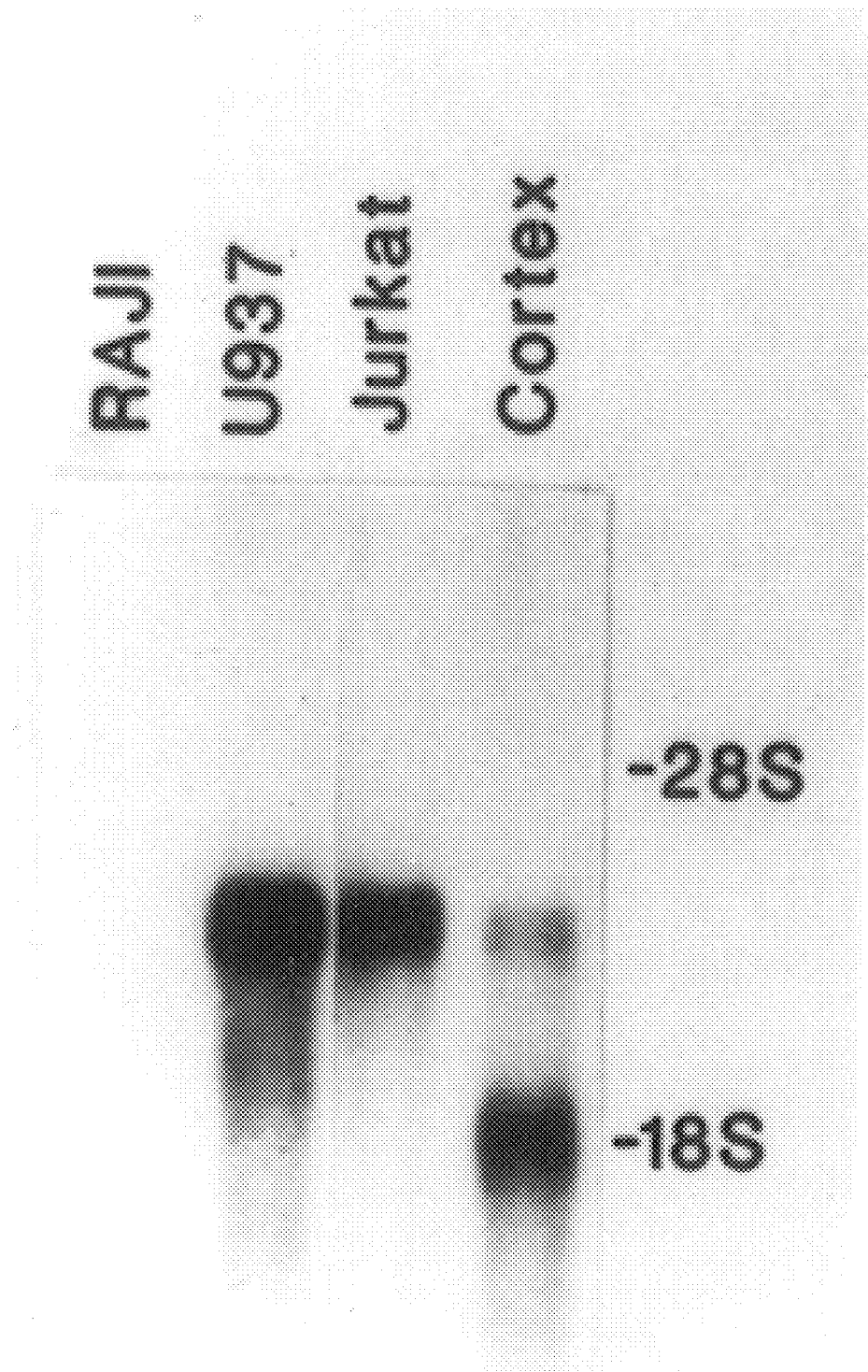
Figure 15B:
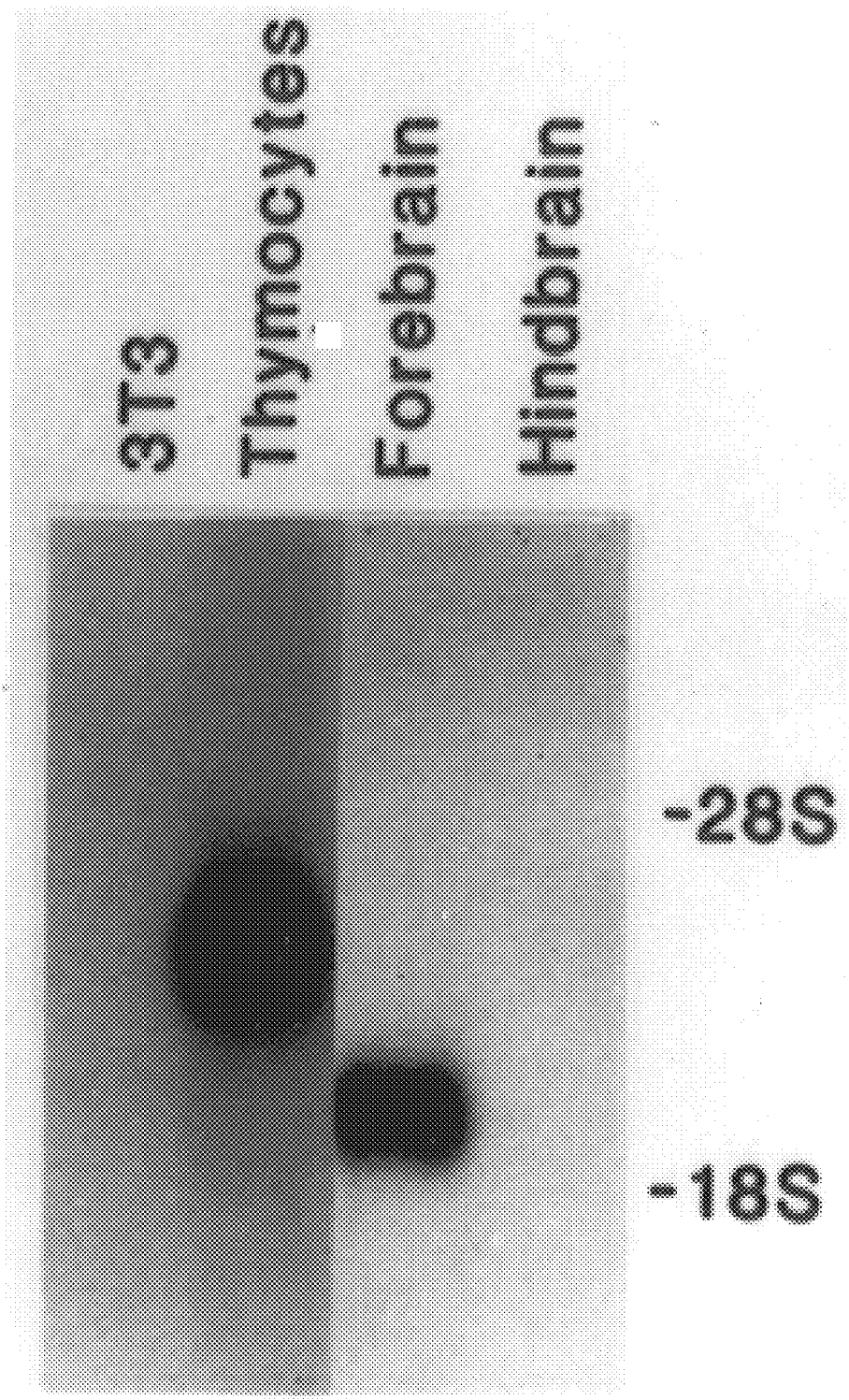

FIGS. 15A–15B. Northern Blot Analysis of RNA Derived from Human and Mouse Brain, Lymphoid, and Myeloid Cells A. Northern blot analysis of human RNA samples. One microgram of poly(A)$^+$ RNA from Raji (T4$^-$ B cell line), U937 (T4$^+$ monocytic cell line), and Jurkat (T4$^+$ T cell line), and five micrograms of poly(A)$^+$ RNA from cerebral cortex, were electrophoresed through a 1% agarose-formaldehyde gel, blotted onto Hybond (Amersham), and probed with a $^{32}$P-labelled T4 cDNA insert, pT4B (70).

B. Northern blot analysis of mouse RNA samples. Five micrograms of poly(A)$^+$ RNA from 3T3 cells (fibroblast cell line), forebrain, and hindbrain, and 20 micrograms of total RNA from thymocytes, were eletrophoresed through a 1% agarose-formaldehyde gel, transferred onto Hybond, and probed with a $^{32}$P-labelled L3T4 cDNA insert, pL3T4B.

Figure 16:
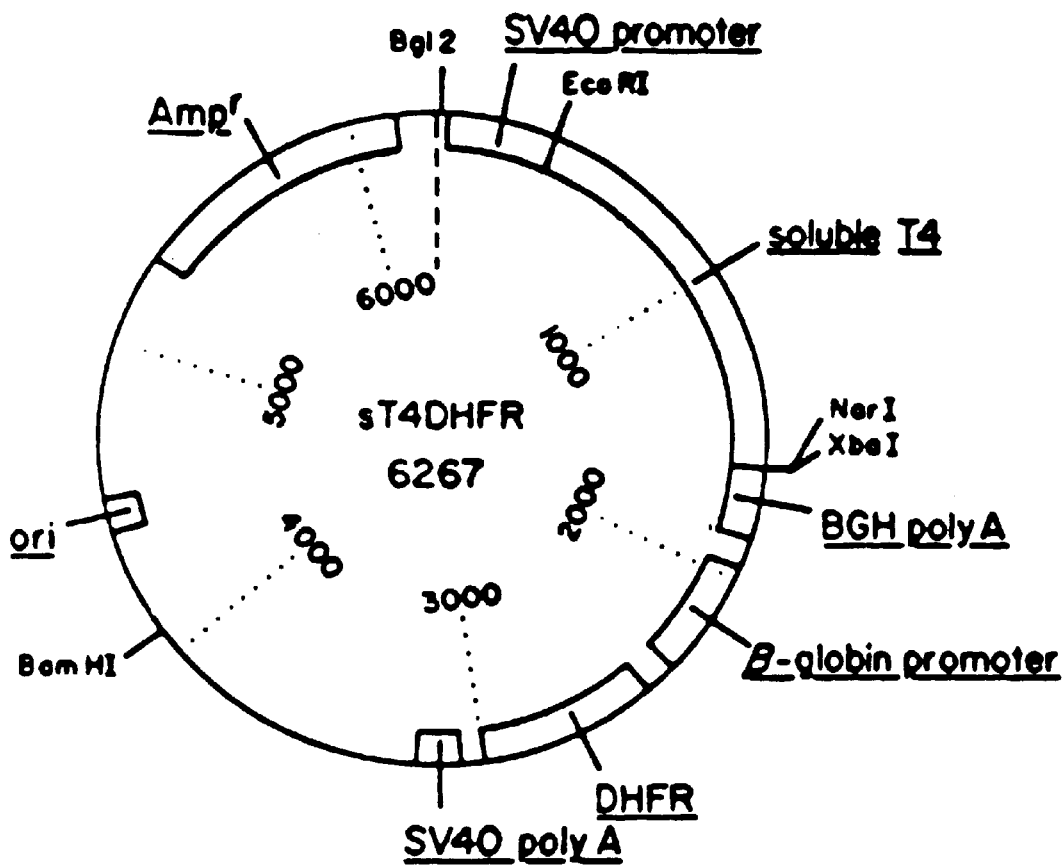

FIG. 16. Plasmid Map of psT4DHFR

Plasmid psT4DHFR is a pUC18 derivative containing bp 1-1257 of the T4 cDNA clone pT4B which encodes the leader and extracellular segment of T4 (SEQ ID NO:18–19). This sT4 cDNA is inserted between an SV40 early promoter and a synthetic linker containing a TAA termination codon (inset) followed by the polyadenylation region of the bovine growth hormone gene. The sT4 (SEQ ID NO:20–21) expression cassette is linked to a mouse hdfr expression cassette consisting of the β-globin promoter, mouse dhfr coding sequence, and the SV40 polyadenylation region.

FIG. 17. Fluorescent Histogram (cell number vs. fluorescence intensity)

sT4 inhibits HIV binding to T4+ CEM cells. Cells were incubated with buffer (•-•-•-), HIV preincubated with sT4 (—), or with HIV preincubated with concentrated control supernatant: from untransformed DXB-11 cells (---), washed, exposed to fluorescentconjugated anti-HIV antibody, and analyzed by cytofluorometry.

Figure 18A:
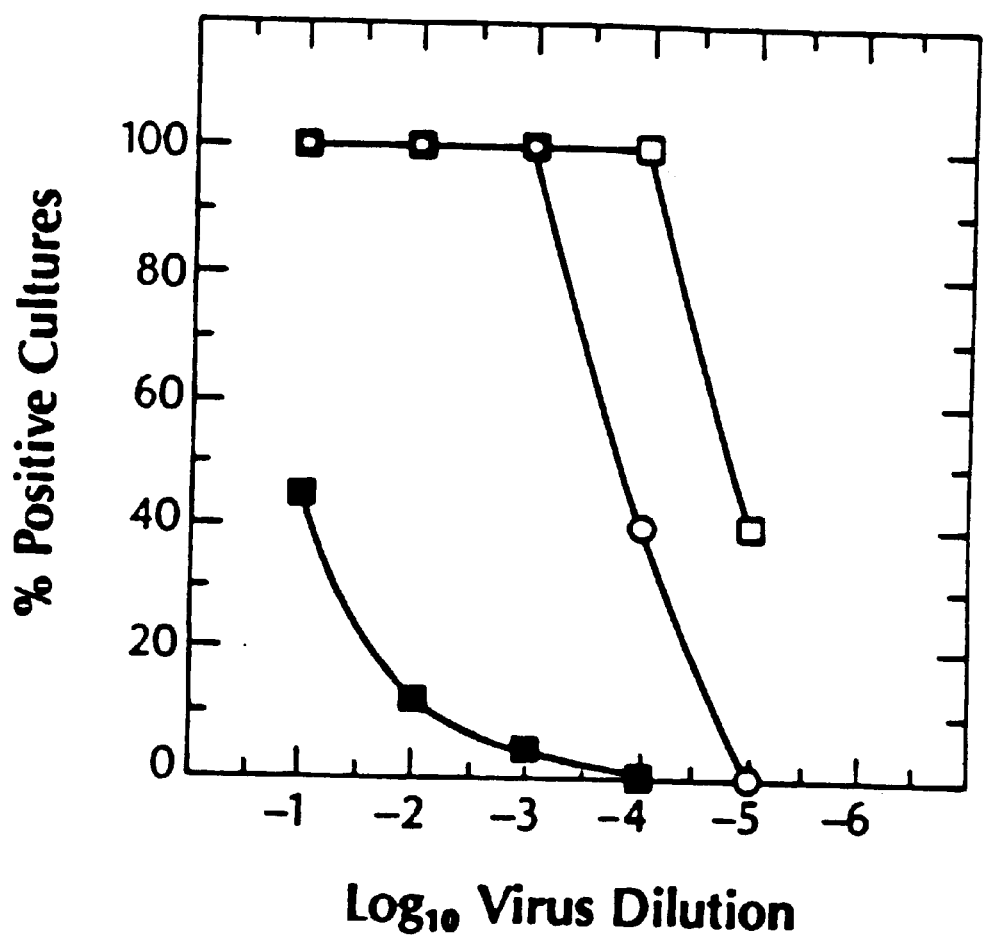
Figure 18B:
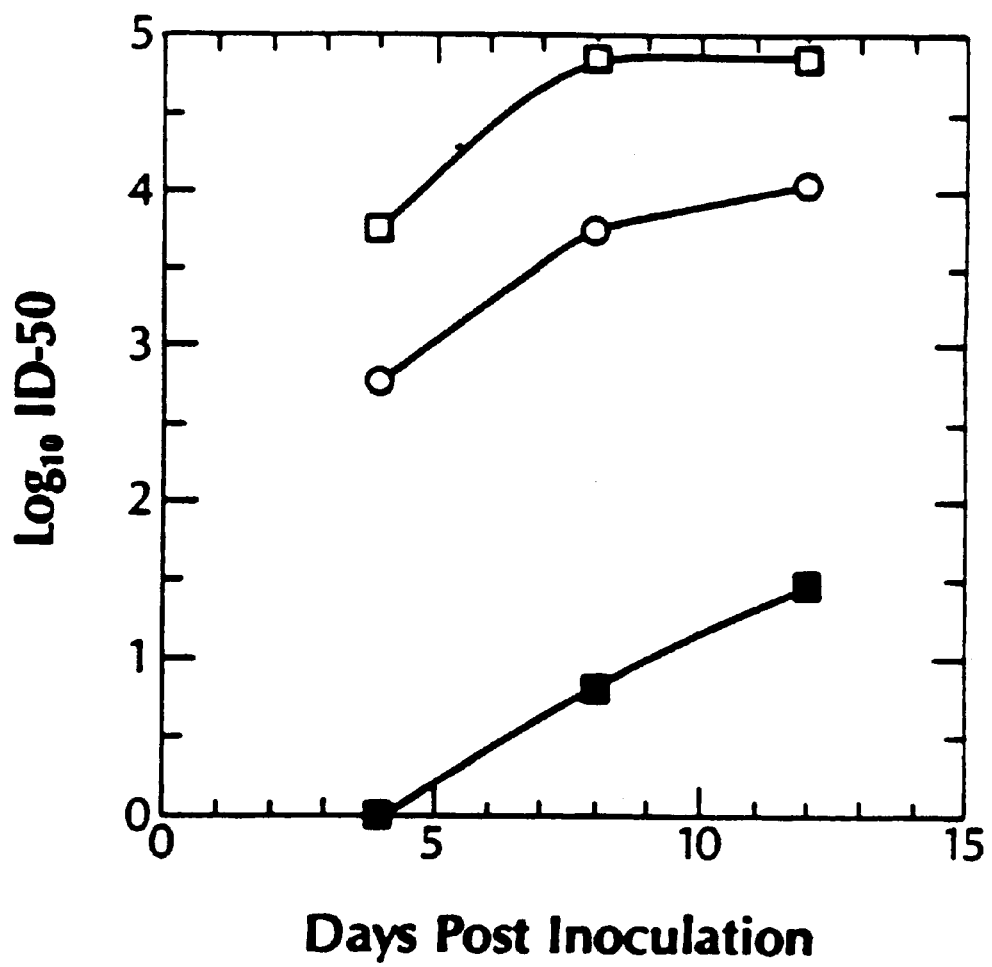
Figure 18C:
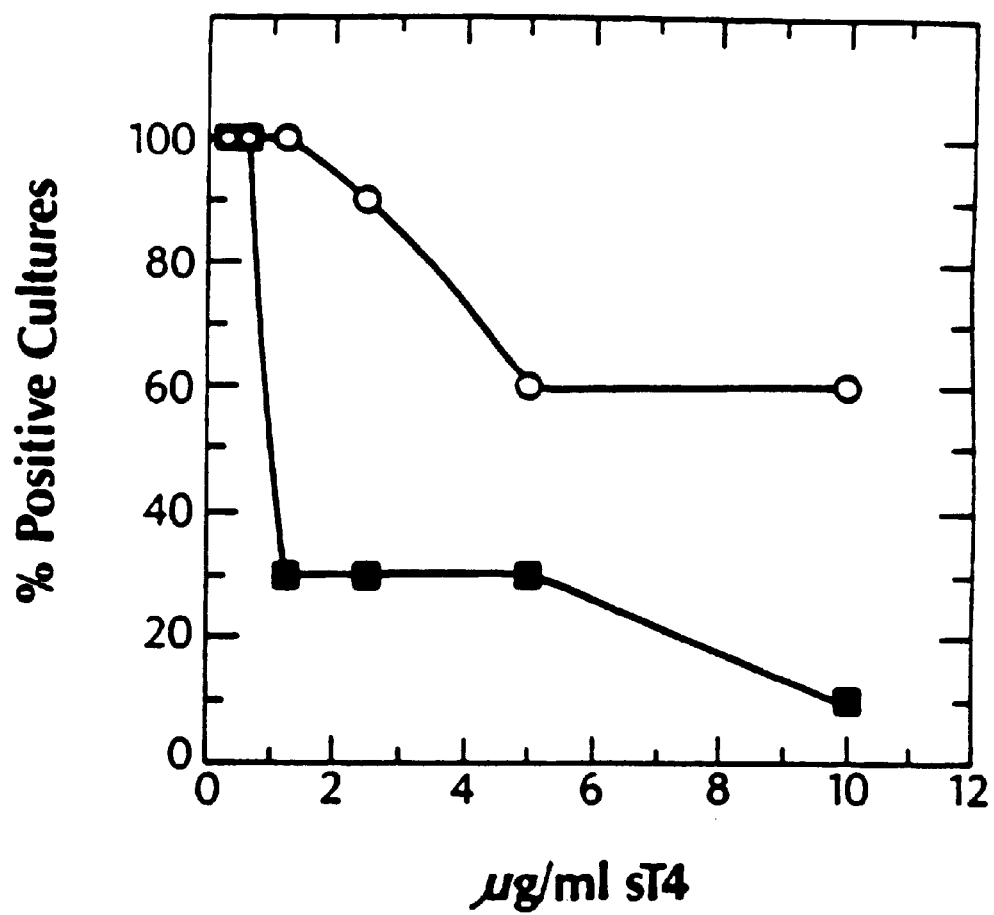

FIGS. 18A–18C. Inhibition of HIV Infectivity by sT4

Infectivity titration of an HIV inoculum (ID-50 assay) was performed. Serial 10-fold dilutions of virus inoculum are incubated with indicator cells (PHA-stimulated human lymphocytes) for 18 hrs. The cells are then washed and plated in microculture ($1 \times 10^5$ cells per culture, 10 cultures per dilution). At day 4, 8, and 12, supernatants are tested for HIV by the antigen capture assay. ID-50 titrations were performed in media containing 8.6 $\mu$g/ml sT4 which was added to the HIV dilution 30 minutes prior to inoculation of cells and maintained in the culture media throughout the experiment (■), or in media containing sT4 introduced after the initial 18 hr inoculum (○) (delayed addition control), or in media without sT4 (□) (control).

A. Plot of percent of cultures positive for HIV at day 8 versus dilution of virus inoculum.

B. Plot of ID-50 (reciprocal of virus dilution at which 50% of cultures are positive) at days 4, 8, and 12.

C. Plot of percent of cultures positive for HIV at day 8 versus varying concentrations of sT4 using a $10^{-3}$ dilution of HIV.

DETAILED DESCRIPTION OF THE INVENTION

A single-stranded nucleic acid molecule is provided which encodes an amino acid sequence comprising at least a portion of a T4 glycoprotein. In one embodiment of the invention, the nucleic acid molecule encodes an amino acid sequence capable of specifically forming a complex with a human immunodeficiency virus (HIV) envelope glycoprotein. Within this application, glycoprotein 110 (gp110) and glycoprotein 120 (gp120) refer to the same HIV envelope glycoprotein. In another embodiment of the invention, the nucleic acid molecule is at least 90% homologous to a nucleic acid molecule which encodes an amino acid sequence which is at least a portion of a T4 glycoprotein. In still another embodiment of the invention, the nucleic acid molecule encodes an amino acid sequence which, in addition to its capablility of specifically forming a complex with a human immunodeficiency virus envelope glycoprotein, is soluble in an aqueous solution. Within this application "aqueous solution" includes, but is not limited to, detergent-free aqueous buffers and body fluids such as blood, plasma and serum. Additionally, "soluble T4" and "sT4" mean a fragment of a T4 glycoprotein which is soluble in an aqueous solution. In a further embodiment of the invention, the nucleic acid molecule encodes an amino acid sequence which is at least a portion of a human T4 glycoprotein.

Also provided is a nucleic acid molecule which is complementary to a single-stranded nucleic molecule encoding an amino acid sequence comprising at least a portion of a T4 glycoprotein. This complementary nucleic acid molecule may be labeled with a detectable marker.

Such detectable markers are known in the art to which this invention pertains and include detectable enzymes, radiolabeled moieties, fluorescent moieties, and chemiluminescent moieties.

The single-stranded nucleic acid molecule may be a DNA molecule. In one embodiment of the invention, the DNA molecule comprises at least a portion of the genomic DNA molecule represented by the restriction enzyme map shown in FIG. 10. In another embodiment of the invention, the single-stranded nucleic acid molecule may be a cDNA molecule which comprises at least a portion of the nucleic acid sequence shown in FIG. 6. In a specific embodiment of the invention, the cDNA molecule encodes an amino acid sequence capable of specifically forming a complex with a human immunodeficiency virus envelope glycoprotein and soluble in an aqueous solution. This cDNA molecule comprises at least a portion of the nucleic acid sequence shown in FIG. 6. In a specific embodiment of the invention, the nucleic acid molecule comprises the nucleotide sequence shown in FIG. 6 from base pair 1 to base pair 1257 and the termination codon TAA.

The present invention further provides an RNA molecule which encodes an amino acid sequence comprising at least portion of a T4 glycoprotein.

A method for detecting a single-stranded nucleic acid molecule encoding an amino acid sequence which is at least a portion of a T4 glycoprotein is provided by the present invention. This method comprises contacting single-stranded nucleic acid molecules with a labeled, single-stranded nucleic acid molecule which is complementary to a single-stranded nucleic acid molecule encoding an amino acid sequence which is at least a portion of a T4 glycoprotein, under conditions permitting hybridization of complementary single-stranded nucleic acid molecules. Hybridized nucleic acid molecules are separated from single-stranded nucleic acid molecules to detect a single-stranded nucleic acid molecule which encodes an amino acid sequence which is at least a portion of a T4 glycoprotein. In one embodiment of the invention, the detected single-stranded molecule is a DNA molecule derived from chromosomal DNA. The chromosomal DNA may be derived from lymphoid, myeloid or brain cells. The lymphoid cell may be a T cell or a B cell. Furthermore, the myeloid cell may be a granulocyte site or a macrophage.

The present invention also provides an amino acid sequence which comprises at least a portion of a T4 glycoprotein. In one embodiment of the invention, the amino acid sequence is capable of specifically forming a complex with a human immunodeficiency virus envelope glycoprotein. In another embodiment of the invention, the amino acid sequence is at least 90% homologous to a portion of a T4 glycoprotein and is capable of specifically forming a complex with a human immunodeficiency virus envelope glycoprotein. In yet a further embodiment of the invention, the amino acid sequence which is at least 90% homologous to a portion of a T4 glycoprotein, in addition to its capability of specifically forming a complex with a human immunodeficiency virus envelope glycoprotein, is soluble in an aqueous solution.

Also provided is a peptide which comprises at least one amino acid sequence of the present invention which is a portion of a T4 glycoprotein. A polypeptide which comprises at least two of these peptides is also provided.

In one embodiment of the invention, the amino acid sequence which is capable of specifically forming a complex with a human immunodeficiency virus envelope glycoprotein and which is soluble in an aqueous solution is useful as a therapeutic agent for the treatment of a subject infected with a human immunodeficiency virus, i.e. as a prophylaxis for AIDS. In a preferred embodiment of the invention, the amino acid sequence comprises the amino acid sequence shown in FIG. 6 from at least amino acid −23 to at most amino acid +374. Other preferred embodiments of the invention include amino acid sequences which comprise the amino acid sequence shown in FIG. 6 from at least amino acid +287 to at most amino acid +374, from at least amino acid +182 to at most amino acid +286, from at least amino acid +112 to at most amino acid +181, and from at least amino acid +1 to at most amino acid +111. In a specific embodiment of the invention, the amino acid sequence comprises the amino acid sequence shown in FIG. 6 from amino acid +1 to amino acid +371. In another specific embodiment of the invention, the amino acid sequence has a carboxy terminus which comprises the amino acid sequence Thr-Pro-Val.

A pharmaceutical composition useful as a therapeutic agent for the treatment of a subject infected with a human immunodeficiency virus is also provided. This pharmaceutical composition comprises an amino acid sequence of the present invention which is capable of specifically forming a complex with a human immunodeficiency virus envelope glycoprotein and is soluble in an aqueous solution and a pharmaceutically acceptable carrier. Such pharmaceutically acceptable carriers are known in the art to which the present invention pertains and include, but are not limited to, 0.01–0.1M, preferably 0.05 M, phosphate buffer or 0.8% saline.

A method for treating a subject infected with a human immunodeficiency virus is also provided. This method comprises administering to the subject an effective amount of a pharmaceutical composition containing a pharmaceutically acceptable carrier and an amino acid sequence of the present invention, capable of specifically forming a complex with a human immunodeficiency virus envelope glycoprotein and soluble in an aqueous solution, so as to render human immunodeficiency viruses (also referred to herein as AIDS viruses) with which the subject is infected incapable of infecting T4$^+$ cells.

Characterization of the in vitro biological and immunological properties of the sT4 protein indicate the protein is of value in the prevention and treatment of AIDS. Studies indicate the sT4 protein acts as an inhibitor of extracellular and cell to cell spread of the virus. Because sT4 has been shown to block virus binding to T4$^+$ target cells in culture, it is believed administration of sT4 to infected persons would act to inhibit the extracellular spread of the virus. Therefore, sT4 is of value both as a prophylactic and therapeutic agent for treatment of AIDS.

As a prophylactic, sT4 is administered to individuals at high-risk for the disease or individuals who show exposure to HIV by the presence of antibodies to virus. Administration of an effective amount of sT4 at an early stage of the disease or prior to its onset acts to inhibit infection of $T4^+$ lymphocytes by HIV. As a therapeutic, administration of sT4 to persons infected with HIV acts to inhibit extracellular spread of the virus.

Fusion between HIV infected cells and other $T4^+$ lymphocytes also appears to be a route of virus spread. Further, fusion may be responsible, in part, for the impairment of $T4^+$ lymphocyte function and ultimately the depletion of $T4^+$ lymphocytes in infected individuals. Cell fusion is dependent on both viral envelope gene products and the T4 receptor and can be inhibited by the OKT4A, or similar monoclonal antibodies (Mabs) (120). sT4 interferes with cell fusion and therefore is expected to diminish the cell to cell spread of virus and the loss of $T4^+$ lymphocyte function.

The T4 receptor is monomorphic and thus sT4 is believed to be a universal inhibitor of virus which recognize the surface domain of the T4 receptor, including all HIV.

sT4 may be used in combination with other agents, for example, in association with agents directed against other HIV proteins, such as reverse transcriptase, protease or tat. An effective therapeutic agent against HIV should prevent virus mediated as well as cell to cell transmission of infection. sT4 may also be used in combination with other anti-viral agents, for example, azidothymidine (AZT).

The sT4 protein of this invention also has utility as an inhibitor of $T4^+$ cell function. Numerous studies suggest a critical role for the CD4 receptor (CD4 is general terminology for the human T4 receptor and its counterparts in other mammalian cells) in immune tolerance, particularly in the pathogenesis and progression of autoimmune diseases and in host specific graft rejection. Of particular relevance to sT4 are the observations with anti-CD4 Mabs. Through their association with the CD4 receptor, certain of these Mabs ameliorate autoimmune responses and graft rejection. Examples of such action include inhibition of T-cell function in vitro, for example, antigen induced proliferation, lymphokine secretion and helper cell function by certain anti-CD4 Mabs; treatment of systemic lupus erythematosus by administration of anti-CD4 Mabs to retard the onset of murine lupus; and grafting studies in mice wherein a single dose of murine Mab directed against the murine CD4 receptor results in acceptance of the allograft.

The molecular consequence of the binding of Mab to CD4 is unclear. The Mabs may block the association of CD4 with its ligand, which ligand, evidence suggests, is a conserved epitope on MHC class II antigens (121,122). However, at least some of these same Mabs inhibit CD4 cell activation by an apparent class II independent path.

sT4 is also believed to inhibit T-cell interactions as a competitor of cellular T4, perhaps by binding to extracellular target molecules which normally interact with the surface domain of the T4 receptor. This distinction between Mabs and sT4 could have important functional consequences. For example, whereas some Mabs directed against T4 elicit a response on the T4 cell, sT4 may elicit a response on cells expressing MHC class II antigens. Also, the affinity of T4 for its presumed class II ligand appears to be quite low compared to the high affinities of Mabs directed against T4. Thus, although Mabs and sT4 may interfere with the same processes, they would affect different target molecules and different target cells.

As a prophylactic or therapeutic, sT4 is administered parenterally, preferably intravenously. The agent can be administered by infusion or by injection, e.g., daily, weekly or monthly. The amount and rate of sT4 administration is selected so as to maintain an effective amount of sT4 in circulation. An alternative mode of administration would be extracorporal, employing sT4 as a dialysis agent.

The sT4 protein of this invention can also be used as a reagent to identify natural, synthetic or recombinant molecules which act as therapeutic agents or inhibitors of $T4^+$ cell interactions.

For example, sT4 protein can be used in screening assays, such as assays for protein interaction measured by ELISA based methodologies, to provide a biochemically pure, aqueous soluble reagent which may be used in combination with other reagents to assay for competitors of the T4 receptor surface domain interactions. For example, since sT4 binds to HIV env protein or mixtures containing HIV env proteins, it can be used to screen for inhibitors of virus binding. Based on in vitro data showing that sT4 binds to cells expressing HIV env proteins, sT4 can also serve as a selective targeting molecule for HIV infected cells in vivo. As a target specific carrier protein, sT4 can serve, for example, as the carrier protein for delivery of cytotoxic agents to the infected cells.

In addition, based on data showing that the T4 receptor specifically associates with MHC class II antigens on antigen-presenting cells as suggested by the class restriction of T4+ cells, sT4 can be used in combination with class II antigens to test for inhibitors of T4 lymphocyte—target cell interactions. In addition to these examples, which are based on direct binding assays between sT4 and its target molecules, more complex assays can be designed which rely on the biochemical responses to sT4 recognition.

The present invention also provides a purified polypeptide encoded by a cDNA molecule which comprises at least a portion of the nucleic acid sequence shown in FIG. 6.

Further provided is a vector which comprises a cDNA molecule which is at least a portion of the nucleic acid sequence shown in FIG. 6. In one embodiment of the invention, the vector comprises a plasmid. In another embodiment of the invention, the vector comprises a virus.

A host vector system for the production of an amino acid sequence which is at least a portion of a T4 glycoprotein is also provided by the present invention. This host vector system comprises a plasmid of the present invention in a suitable host. In one embodiment of the invention, the suitable host is a bacterial cell. In another embodiment of the invention, the bacterial cell is an *Escherichia coli* cell. In yet another embodiment of the invention, the suitable host a eucaryotic cell. In a further embodiment of the invention, the eucaryotic cell is a mammalian cell. In yet a further embodiment of the invention, the eucaryotic cell is a yeast cell. In still another embodiment of the invention, the suitable host is an insect cell.

A method for producing a amino acid sequence which is at least a portion of a T4 glycoprotein is further provided. This method comprises growing a host vector system of the present invention under suitable conditions permitting production of at least a portion of a T4 glycoprotein, and recovering the resulting portion of a T4 glycoprotein. The present invention further provides host vector systems and methods for producing an amino acid sequence which is at least a portion of a T4 glycoprotein wherein the vector comprises a cDNA molecule of the present invention and a virus. Suitable hosts include, but are not limited to, bacterial cells, e.g. *Escherichia coli* cells, eucaryotic cells, e.g. mammalian and yeast cells, and insects. An amino acid sequence which is at least a portion of a T4 glycoprotein may be produced by growing a host vector system which comprises a virus and a cDNA molecule of the present invention under suitable conditions permitting production of at least a portion of T4 glycoprotein. The resulting portion of a T4 glycoprotein may be recovered from the host vector system by methods known in the art. The present invention also provides a means for producing sT4 consisting of the predicted extracellular domain of the T4 receptor. Using that portion of the T4 cDNA which encodes the leader and extracellular domains of the T4 receptor, i.e., pre sT4, vectors are constructed capable of overexpression of sT4 in mammalian cells. The sequence of one sT4 is as follows:

```
              10          20          30          40          80          60
              *           *           *           *           *           *
        CAA GCC CAG AGC CCT GCC ATT TCT GTG GGC TCA GGT CCC TAC TGC TCA GCC CCT TCC TCC 70          80          90         100         110         120
              *           *           *           *           *           *
        CTC GGC AAG GCC ACA ATG AAC CGG GGA GTC CCT TTT AGG CAC TTG CTT CTG GTG CTG CAA
                        Met Asn Arg Gly Val Pro Phe Arg His Leu Leu Leu Val Leu Gln 130         140         150         160         170         180
              *           *           *           *           *           *
        CTG GCG CTC CTC CCA GCA GCC ACT CAG GGA AAG AAA GTG GTG CTG GGC AAA AAA GGG GAT
        Leu Ala Leu Leu Pro Ala Ala Thr Gln Gly Lys Lys Val Val Leu Gly Lys Lys Gly Asp 190         200         210         220         230         240
              *           *           *           *           *           *
        ACA GTG GAA CTG ACC TGT ACA GCT TCC CAG AAG AAG AGC ATA CAA TTC CAC TGG AAA AAC
        Thr Val Glu Leu Thr Cys Thr Ala Ser Gln Lys Lys Ser Ile Gln Phe His Trp Lys Asn 250         260         270         280         290         300
              *           *           *           *           *           *
        TCC AAC CAG ATA AAG ATT CTG GGA AAT CAG GGC TCC TCC TTA ACT AAA GGT CCA TCC AAG
        Ser Asn Gln Ile Lys Ile Leu Gly Asn Gln Gly Ser Ser Phe Leu Thr Lys Gly Pro Ser Lys 310         320         330         340         350         360
              *           *           *           *           *           *
        CTG AAT GAT CGC GCT GAC TCA AGA AGA AGC CTT TGG GAC CAA GGA AAC TTC CCC CTG ATC
        Leu Asn Asp Arg Ala Asp Ser Arg Arg Ser Leu Trp Asp Gln Gly Asn Phe Pro Leu Ile 370         380         390         400         410         420
              *           *           *           *           *           *
        ATC AGG AAT CTT AAG ATA GAA GAC TCA GAT ACT TAC ATC TGT GAA GTG GAG GAC CAG AAG
        Ile Lys Asn Leu Lys Ile Glu Asp Ser Asp Thr Tyr Ile Cys Glu Val Glu Asp Gln Lys 430         440         450         460         470         480
              *           *           *           *           *           *
        GAG GAG GTG CAA TTG CTA GTG TTC GGA TTG ACT GCC AAC TCT GAC ACC CAC CTG CTT CAG
        Glu Glu Val Gln Leu Leu Val Phe Gly Leu Thr Ala Asn Ser Asp Thr His Leu Leu Gln
```

```
              490         500         510         520         530         540
               *           *           *           *           *           *
GGG CAG AGC CTG ACC CTG ACC TTG GAG AGC CCC CCT GGT AGT AGC CCC TCA GTG CAA TGT
Gly Gln Ser Leu Thr Leu Thr Leu Glu Ser Pro Pro Gly Ser Ser Pro Ser Val Gln Cys 550         560         570         580         590         600
               *           *           *           *           *           *
AGG AGT CCA AGG GGT AAA AAC ATA CAG GGG GGG AAG ACC CTC TCC GTG TCT CAG CTG GAG
Arg Ser Pro Arg Gly Lys Asn Ile Gln Gly Gly Lys Thr Leu Ser Val Ser Gln Leu Glu 610         620         630         640         650         660
               *           *           *           *           *           *
CTC CAG GAT AGT GGC ACC TGG ACA TGC ACT GTC TTG CAG AAC CAG AAG AAG GTG GAG TTC
Leu Gln Asp Ser Gly Thr Trp Thr Cys Thr Val Leu Gln Asn Gln Lys Lys Val Glu Phe 670         680         690         710         720         730
               *           *           *           *           *           *
AAA ATA GAC ATC GTG GTG CTA GCT TTC CAG AAG GCC TCC AGC ATA GTC TAT AAG AAA GAG
Lys Ile Asp Ile Val Val Leu Ala Phe Gln Lys Ala Ser Ser Ile Val Tyr Lys Lys Glu 730         740         750         760         770         780
               *           *           *           *           *           *
GCG GAA CAG GTG GAC TTC TCC TTC CCA CTC GCC TTT ACA GTT GAA AAG CTG ACG GGC AGT
Gly Glu Gln Val Asp Phe Ser Phe Pro Leu Ala Phe Thr Val Glu Lys Leu Thr Gly Ser 790         800         810         820         830         840
               *           *           *           *           *           *
GGC GAG CTG TGG TGG CAG GCG GAG AGG GCT TCC TCC TCC AAG TCT TGG ATC ACC TTT GAC
Gly Glu Leu Trp Trp Gln Ala Glu Arg Ala Ser Ser Ser Lys Ser Trp Ile Thr Phe Asp 850         860         870         880         890         900
               *           *           *           *           *           *
CTG AAG AAC AAG GAA GTG TCT GTA AAA CGG GTT ACC CAG GAC CCT AAG CTC CAG ATG GGC
Leu Lys Asn Lys Glu Val Ser Val Lys Arg Val Thr Gln Asp Pro Lys Leu Gln Met Gly 910         920         930         940         950         960
               *           *           *           *           *           *
AAG AAG CTC CCG CTC CAC CTC ACC CTG CCC CAG GCC TTG CCT CAG TAT GCT GGC TCT GGA
Lys Lys Leu Pro Leu His Leu Thr Leu Pro Gln Ala Leu Pro Gln Tyr Ala Gly Ser Gly 970         980         990        1000        1010        1020
               *           *           *           *           *           *
AAC CTC ACC CTG GCC CTT GAA GCG AAA ACA GGA AAG TTG CAT CAG GAA GTG AAC CTG GTG
Asn Leu Thr Leu Ala Leu Glu Ala Lys Thr Gly Lys Leu His Gln Glu Val Asn Leu Val 1030        1040        1050        1060        1070        1080
               *           *           *           *           *           *
GTG ATG AGA GCC ACT CAG CTC CAG AAA AAT TTG ACC TGT GAG GTG TGG GGA CCC ACC TCC
Val Met Arg Ala Thr Gln Leu Gln Lys Asn Leu Thr Cys Glu Val Trp Gly Pro Thr Ser 1090        1100        1110        1120        1130        1140
               *           *           *           *           *           *
CCT AAG CTG ATG CTG AGC TTG AAA CTG GAG AAC AAG GAG GCA AAG GTC TCG AAG CGG GAG
Pro Lys Leu Met Leu Ser Leu Lys Leu Glu Asn Lys Glu Ala Lys Val Ser Lys Arg Glu 1150        1160        1170        1180        1190        1200
               *           *           *           *           *           *
AAG GCG GTG TGG GTG CTG AAC CCT GAG GCG GGG ATG TGG CAG TGT CTG CTG AGT GAC TCG
Lys Ala Val Trp Val Leu Asn Pro Glu Ala Gly Met Trp Gln Cys Leu Leu Ser Asp Ser 1210        1220        1230        1240        1250        1260
               *           *           *           *           *           *
GGA CAG GTC CTG CTG GAA TCC AAC ATC AAG GTT CTG CCC ACA TGG TCC ACC CCG GTG TAA
Gly Gln Val Leu Leu Glu Ser Asn Ile Lys Val Leu Pro Thr Trp Ser Thr Pro Val ---

1270
               *
TGG CGC CTC TAG (A SEQ ID NO. 1—2)
```

The coding sequence for sT4 is obtained, for example, by synthesizing the gene using the known DNA sequence, by standard cloning techniques based on the sequence and by reisolation by detection of protein, i.e., transfection of cDNA clones from T4 expressing cell lines and identification by antibodies directed against the protein. cDNA clones carrying the sT4 coding sequence are identified by use of oligonucleotide hybridization probes. The probes are designed based on the known sequence of the T4 protein. Having identified a clone carrying the sT4 coding sequence, the coding sequence is excised by the use of restriction endonucleases and inserted into cloning and/or expression vectors. In an expression vector, the sT4 coding sequence is operatively linked to regulatory functions required or desirable for transcription, translation and processing of the coding sequence.

Regulatory functions include, for example, functions required for RNA polymerase binding and transcription, as well as other functions such as polyadenylation and enhancement of transcriptional sequences. The promoter can be regulatable so that, for example, expression is not induced until after transfection and selection of transformed clones. Promoters useful in the practice of the invention include, for example, the SV40 early promoter, and the long terminal repeats (LTR's) of rous sarcoma virus, moloney sarcoma virus or cytomegalovirus (CMV).

Prior to transfection, the sT4 minigene, i.e., the gene encoding the leader and extracellular domains of the T4 receptor, preferably is incorporated into a larger DNA molecule which comprises a genetic selection marker system. The selection marker system consists of any gene or genes which cause a readily detectable phenotypic change in a transfected host cell. Such phenotypic change may be, for example, foci formation, drug resistance, such as genes for G418 or hygromycin B resistance; or other selectable markers such as xanthine guanine phosphoribosyl transferase (xgprt), thymidine kinase (TK) and galactokinase (galK). A selection marker which permits gene amplification can be employed to increase copy number, whether by increased transfection efficiency or by enhanced intracellular replication of the gene of interest and the selection marker. Such markers which also serve to amplify gene copy number include genes for dihydrofolate reductase (methotrexate resistance), CAD (N-phosphonacetyl-L-aspartate resistance) and adenosine deaminase (2-deoxycoformycin resistance).

Following transcription and translation in mammalian cells, the leader sequence appears to be cleaved and mature sT4 is secreted into the conditioned medium.

In the preferred practice of the invention, the sT4 minigene is linked with a human H-ras or a mouse dihydrofolate reductase (DHFR) minigene to create the expression vectors.

The sT4 minigene is linked, for example, with the human H-ras or mouse DHFR in order to provide a selection marker and means to selectively amplify gene expression through co-transfection with these genes. Common selection markers include, for example, DHFR, G418 or hygromycin which select for integration of as few as a single copy of the gene of interest. Amplification with, for example, methotrexate (mtx) in the DHFR system results in overexpression of the gene.

An alternate means of increased expression of the gene includes use of the ras proto-oncogene. The ras gene family includes the H-ras, K-ras and N-ras genes. In a preferred application of the invention, the H-ras gene is used.

Other DNA functions can be linked directly or indirectly to the sT4 minigene or such functions may be unlinked. See, for example, Axel, U.S. Pat. No. 4,399,216.

Overexpression of gene products in mammalian cells can be achieved by transient or stable means. Transient overexpression can be achieved by viral methods such as the use of vaccinia virus vectors or by gene amplification methods such as with SV-40 based vectors in cells which support SV-40 replication. These methods ultimately lead to cell death. Stable overexpression can be achieved by generation of multiple gene copies such as through selection for gene amplification or through the use of the ras proto-oncogenes.

Overexpression of sT4 protein by co-transfection using the H-ras gene system can be achieved using a number of different cell lines, with the preferred cell line being the NIH-3T3 cell line which is a contact inhibited mouse fibroblast cell line. Other cell lines include the normal rat kidney (NRK) (ATCC 1571) cell line and the rat embryo fibroblast 52 (REF-52) cell line (115).

When using the selection marker system, for example, DHFR with methotrexate (DHFR/MTX technique), wherein amplification of gene copy number is achieved by selective amplification, the Chinese hamster ovary cell line (CHO) is preferred. In particular, CHO cells deficient in DHFR are used (116). Other cell types which may be used include, for example, any mammalian cell which has been modified so as to be $DHFR^-$.

Some $DHFR^+$ cell types may be used in combination with mutant DHFR genes which are less sensitive to methotrexate than normal DHFR (Axel, U.S. Pat. No. 4,399,216). In principle, $DHFR^+$ cells may be used in combination with normal DHFR genes and an additional dominant selectable gene such as the gene for G418 resistance (117). Transfection is carried out using standard techniques (118, 119). These techniques include, for example, calcium phosphate precipitation, DEAE-dextran induced pinocytosis, electroporation and viral transfection.

Following transfection, a cell which carries the sT4 minigene is cultured in a nutrient medium under conditions which permit amplification of the selectable gene. Standard mammalian cell culture medium can be employed, for example, F12 medium (GIBCO, Grand Island, N.Y.) without hypoxanthine and thymidine and containing 10% fetal bovine serum. Cell cultures are maintained at ambient pressure at 30 to 45° C. Cells which survive selection and express high levels of sT4 protein are selected for further culturing. Such cells are cultured under selective conditions and the product, the sT4 protein, is collected and purified.

Cell culture methods which may be employed in the practice of the invention include, for example, use of adherent cells or growth of cells in a suspension.

Conditioned medium (CM) can be collected from cells grown in suspension or adhered to solid supports, i.e., CM is prpeared from adherent cells grown in roller bottles or grown on solid supports and cultured in suspension or in fluidized or packed beds. CM is prepared from suspension cells in stirred-tank vessels.

The sT4 of the invention includes derivatives of the extracellular domain of T4. Such derivatives comprise addition, deletions or subsitutions which alterations do not significantly adversely affect secretion of the protein into the conditioned medium and the affinity of the protein for HIV env protein, i.e., gp120. For example, one or a few amino acids can be added to or deleted from the N- or C-terminus. Or, one or a few amino acids, preferably no more than four amino acids can be inserted into, deleted or substituted for internal amino acids. Alternatively, a hybrid protein, i.e., a translational fusion, can be constructed between sT4 and a protein carrier, another antigen or other sT4 molecules to prepare a poly-sT4 molecule. In yet another alternative, sT4 can be synthetically conjugated to a carrier molecule.

One embodiment of a sT4 derivative is illustrated in the Examples below (see Example 3). Affinity of the sT4 for HIV env can be demonstrated by a competitive binding assay using a sT4 molecule having a known affinity or using antibodies which recognize the T4 receptor, such as OKT4 and OKT4A. Useful derivative sT4 molecules of the invention are selectively precipitated from conditioned medium by OKT4A as shown in Example 3. Derivatives can be prepared chemically, after expression, or genetically, prior to expression, by manipulation of the coding sequence for the leader and/or extracellular domain.

The sT4 of the invention can be purified from the spent culture media using various protein purification techniques, for example, affinity chromatography; ion exchange chromatography; size exclusion chromatography; hydrophobic chromatography or reversed phase chromatography.

sT4 can be purified by affinity chromatography using general group-specific adsorbants, for example, carbohydrate binding or dye affinity ligands; or using ligands that specifically bind to sT4, for example, monoclonal antibody or HIV gp120 protein or portions thereof.

An exemplary purification scheme comprises: (1) growing cells in a serum-free selection growth media; (2) clarification of the conditioned media; and (3) separation of sT4 of the invention from other proteins present in the conditioned media.

In the preferred method, the sT4 is purified from the serum-free culture medium using a series of chromatography steps which are based on the physical properties of the sT4 molecule. The sT4 may also be purified from culture medium containing serum using similar chromatography methods.

In the preferred method of purification of sT4, the culture medium is first passed through an ion exchange column, preferably an S-Sepharose* (Sulpho-propyl Sepharose) column, which binds the sT4 while the majority of contaminating proteins flow through the column. The protein sample is then eluted using a linear salt gradient. A second ion exchange column is used. This column, preferably a Q-Separose* (quarternary amino ethyl Sepharose) column has properties such that the contaminating proteins present in the sample are bound to the column while the sT4 does not bind and is recovered in the column flow-through buffer. Finally, a gel filtration column is used which acts to remove remaining contaminating materials.

An alternative method of purification of sT4 involves the use of monoclonal antibodies directed against sT4. The sT4 protein can be purified in one step by passage of clarified culture media through an affinity gel support to which monoclonal antibody directed against sT4 is bound. The sT4 will bind to the column at the antibody binding site while all contaminating proteins wash through the column. The sT4 is then eluted from the column under conditions that prevent sT4 protein from being inactivated.

The present invention also provides a substance capable of forming a complex with an amino acid sequence which is capable of specifically forming a complex with a human immunodeficiency virus envelope glycoprotein and is soluble in an aqueous solution. In one embodiment of the invention, the substance is an antibody. In another embodiment of the invention, the antibody is a monoclonal antibody. In yet a further embodiment of the invention, the monoclonal antibody is a human monoclonal antibody.

Also provided is a vaccine useful for immunizing a human subject against a human immunodeficiency virus. This vaccine comprises a monoclonal antibody of the present invention and a pharmaceutically acceptable carrier. By administering to a human subject an effective immunizing amount of a vaccine of the present invention, the production of antibodies capable of neutralizing human immunodeficiency viruses may be invoked, thereby immunizing the subject against a human immunodeficiency virus.

Also provided is a substance capable of specifically forming a complex with a monoclonal antibody of the present invention. In one embodiment of the invention, the substance is capable of additionally forming a specific complex with a human immunodeficiency virus envelope glycoprotein. In a preferred embodiment of the invention, the substance comprises a T4 glycoprotein anti-idiotypic antibody which contains an "internal image" of the T4 binding domain capable of recognizing the receptor binding domain of a human immunodeficiency virus envelope glycoprotein.

A pharmaceutical composition is provided which comprises a T4 glycoprotein anti-idiotypic antibody of the present invention and a pharmaceutically acceptable carrier. Further provided is a method for treating a subject infected with a human immunodeficiency virus by administering to the subject an effective amount of the pharmaceutical composition of the present invention which comprises a T4 glycoprotein anti-idiotypic antibody and a pharmaceutically acceptable carrier so as to render human immunodeficiency viruses with which the subject is infected incapable of infecting T4$^+$ cells.

The sT4 can be used in diagnostic assays for the detection of T4 proteins or the molecules with which they interact. For example, quantitation of T4 and T4$^+$ cells and antibodies to T4 would be of diagnostic value for AIDS.

In addition, sT4 can be used to generate new diagnostic reagents, for example, Mabs or other types of molecules for use in the standard immunologic assays, i.e., ELISA, capture immunoassays, radioimaune assays. Because sT4 displays the OKT4, the OKT4A and most if not all of the other surface epitopes of the T4 receptor, sT4 is especially useful in immunodiagnostic assays as it can be used for absolute quantitation of T4 levels in a system. Currently there are no standards for quantitating the T4 receptor.

The T4 receptor resides in three diverse chemical environments: the oxidizing, hydrophilic cell surface; the hydrophobic membrane; and the reducing, hydrophilic cytoplasm. These diverse environments would most likely preclude the isolation of the receptor in its fully native state. sT4, which consists of only the extra-cellular domain, is secreted as a soluble protein into the cell supernatant and its conformation appears to mimic the surface of the receptor surface domain. Thus, sT4 is suitable for detailed structural analysis, in particular for x-ray crystallography. Determination of the three-dimensional structure of sT4 alone or in a complexed form with other interactive molecules could provide a basis for the rational design of selective antagonists and agonists for sT4.

The various prophylaxis and immunization methods for AIDS provided by the present invention are based upon the abilities of the novel peptides, antibodies, and DNA molecules disclosed herein to form complexes with, or hybridize to, specific molecules and to invoke an immunological response effective for neutralizing the AIDS virus. These molecules, methods for their preparation, and methods of AIDS treatment will be better understood by reference to the following experiments and examples which are provided for purposes of illustration and are not to be construed as in any way limiting the scope of the present invention, which is defined by the claims appended hereto.

Materials and Methods

Cells and Antibodies

Peripheral blood leukocytes isolated by Ficoll-Hypaque density gradient centrifugation were fractionated into sheep erythrocyte rosette-positive (E$^+$) cells. T4$^+$ and T8$^+$ subsets within the E$^{30}$ population were isolated by positive selection of T8-bearing cells with anti-T8 antibody and human erythrocytes conjugated with affinity-purified rabbit anti-mouse IgG (10). Cytofluorometric analysis of these subsets demonstrated that the T4$^+$ cells were >95% T4$^+$ and <2% T8$^+$, whereas the T8$^+$ cells were >95% T8$^+$ and <2% T4$^+$.

The Fro 2.2 T cell line (T3$^-$, T4$^+$, T8$^+$, T11$^+$) was derived from an adult patient with undifferentiated acute leukemia. Jurkatt is T3$^-$, T4$^+$, T8$^+$, T11$^-$, RPMI 8402 is T3$^-$, T4$^-$, T8$^-$, T11$^+$. OT-CLL is a chronic lymphocytic leukemia which is T3$^+$, T4$^+$, T8$^-$, and T11$^+$ (22). The T4$^+$ cell lines CEM and Molt 4 were obtained from the American Type Culture Collection. All leukemic T cell lines were continuously grown in RPMI 1640 medium containing 5% fetal calf serum. Transformed B cell lines CB, CP58 and CP94 were derived as previously described (23).

Affinity-purified rabbit anti-mouse IgG was conjugated to human erythrocytes by the chromium chloride method (24).

Cotransformation of L Cells and NIH 3T3 Cells

Murine L tk$^-$aprt$^-$ cells were maintained in Dulbecco's modified Eagle's medium (DME) supplemented with 10% calf serum (Gibco) and 50 micrograms/ml diaminopurine (DAP). L cells were plated out at a density of 5×10$^4$ cells per 10 cm dish, 1 day before transformation. Calcium phosphate precipitates were prepared by the method of Graham and van der Eb (25), as modified by Wigler et al. (26), using 100 ng of pTK and 20 micrograms of high molecular weight T cell or L cell DNA per dish. The L cells were placed under selection in DME with 10% calf serum, 15 micrograms/ml hypoxanthine, 1 microgram/ml aminopterin and 5 micrograms/ml thymidine (HAT medium (27)) on the following day. After 12–14 days of HAT selection, tk$^+$ transformants were screened using the rosetting assay.

Murine NIH 3T3 cells were maintained in DME supplemented with 10% newborn calf serum (Gibco). NIH 3T3 cells were plated out at a density of 5×10$^4$ cells per 10 cm dish, 2 days before transformation. A calcium phosphate precipitate was applied to the cells using 10 micrograms of carrier DNA and either 10 micrograms of T4-pMV6tk/neo or 10 micrograms of T4-pVcos7 and 500 ng of pSV2neo. After 2 days, the cells were placed under selection in DME with 10% calf serum and 500 micrograms/ml G418 (Geneticin$^\bullet$; Gibco). Rosetting assays were performed on surviving colonies one week after growth in selective medium.

Rosetting Assay

After one rinse with phosphate-buffered saline (PBS), the plates were incubated with 2.5 ml of the purified monoclonal antibody OKT$^\bullet$4A (1 mg/ml) diluted at 1/500 in PBS containing 5% fetal calf serum for 45 minutes at room temperature. Free antibody was removed from the plates with three gentle rinses in PBS. Six milliliters of human erythrocytes conjugated with purified rabbit anti-mouse IgG antibody (2% v/v stock suspension, diluted 1/10 in PBS/5% fetal calf serum) were added and the plates were left at room temperature. After 45 minutes, free erythrocytes were gently aspirated and PBS was added prior to inspection for rosette-positive colonies.

Cytofluorometric Analysis

Adherent cells were removed with 0.005 M EDTA in PBS and washed once with PBS containing 1% bovine serum albumin (BSA) and 0.01% sodium azide (cytowash). Cells (5×10$^6$) in 0.1 ml were added to tubes with appropriate dilutions of OKT$^\bullet$4, OKT$^\bullet$8 or control antibodies. The cell-antibody mixture was incubated for 45 minutes at 4° C. and then washed twice in cytowash. Fluorescein isothiocyanate (FITC)-conjugated goat anti-mouse IgG+A+M (Cappel) was added to the cells and incubated for 1 hour at 4° C. The cells were then washed three times in cytowash and resuspended in 0.5 ml of PBS with 0.01% sodium azide. The cells were analyzed on a Becton Dickinson FACS IV Cell Sorter and the data was stored and plotted using a VAX 11/780 computer (Digital Equipment Co.)

RNA and DNA Isolation

Total RNA was isolated from cells by homogenation in 4 M guanidinium thiocyanate, followed by ultracentrifugation through a 5.7 M CsCl cushion (28). Poly(A)$^+$ selection was achieved by oligo(dT)-cellulose chromatography (Type 3, Collaborative Research) (29). High molecular weight genomic DNA was prepared as described by Wigler et al. (26).

cDNA and Genomic Libraries

Double-stranded cDNA was synthesized from poly(A)$^+$ RNA derived from peripheral human T cells (20). After treatment with EcoRI methylase ard T4 DNA polymerase, the double-stranded cDNA was cloned into the EcoRI site of λgt10 (30) using EcoRI linkers. The Charon 4 human genomic library was generously provided by Dr. Tom Maniatis (Harvard University) (31).

Synthesis of a Subtracted cDNA Probe $^{32}$P-labeled cDNA was synthesized from poly(A)$^+$ RNA derived from the primary transformant, LTD-4, as described by Davis et al. (32). After annealing the cDNA to an excess of untransformed L cell poly(A)$^+$ RNA (Rot=3000), single-stranded sequences, which were enriched for human cDNAs, were isolated by hydroxyapatite chromatography (32). Prior to filter hybridization, the subtracted cDNA probe was concentrated with sec-butanol and desalted on a G-50 Sephadex column equilibrated in TE.

Screening of cDNA and Genomic Libraries

The peripheral human T cell library was plated on E. coli C600/HFL and the human genomic library was plated on E. coli LE392. Screening of duplicate filters was carried out according to the standard procedure (33), with the hybridization performed in 50% formamide and 5×SSC at 42° C. In the screen of the cDNA library, 6×10$^4$ cpm of subtracted probe was applied per 137 mm nitrocellulose filter. Filters from the genomic library were hybridized to a nick-translated (34) cDNA insert. The washes were performed at 68° C., with a final wash in 0.2×SSC. Autoradiography was performed at −70° C. in the presence of intensifying screens for 12 days.

DNA Sequencing

Restriction fragments of pT4B were subcloned into the M13 vectors mp18 and mp19 (35). Sequencing reactions were performed using the dideoxy chain termination technique (36). The sequencing strategy is depicted in FIG. 3B.

Southern and Northern Blot Hybridizations

High molecular weight cellular DNAs were digested with 5 units of restriction nuclease per microgram of DNA according to the manufacturer's recommendation (Boehringer Mannheim). Samples (10 micrograms) were subjected to electrophoresis on a 0.8% agarose gel. DNA fragments were transferred to GeneScreen (New England Nuclear; (37)) and hybridized as described by Church and Gilbert (38).

RNA was run on a 0.8% agarose-formaldehyde gel (39) and transferred to GeneScreen. Northern hybridization was performed according to the procedures supplied by the manufacturer. Both Southern and Northern blots were hybridized to nick-translated probes.

Synthesis and In Vitro Translation of SP6 RNA

The kb T4 cDNA was subcloned into the EcoRI site of pSP65 (Promega Biotec) and linearized with HindIII. Transcription of linearized plasmid DNA (1 microgram) with SP6 polymerase in the absence of radiolabeled nucleotides was performed as described (40), except that GpppG and unlabeled CTP were added to the transcription buffer. One-tenth of the reaction mixture was translated in a wheat germ system (Bethesda Research Laboratories) containing L-[$^{32}$S]-methionine (Amersham) and 1 micromolar S-adenosylmethionine. The in vitro translation products were subjected to SDS-polyacrylamide electrophoresis under reducing conditions as described below.

Cell Labeling, Lectin Chromatography and Immunoprecipitation

Cells were grown for 12 hours in methionine-free DME medium containing 10% dialyzed calf serum and 1 mCi of L-[$^{32}$S]-methionine (Amersham) as previously described (41). The cells were solubilized in 10 mM Tris (pH 7.4), 150 mM NaCl (TBS) containing 0.5% Nonidet P-40 (Shell) and 0.2 mM phenylmethylsulfonyl fluoride (Sigma). The lysates were centrifuged for 1 hour at 100,000×g, and the supernatants were subjected to lentil lectin chromatography (Pharmacia) according to the procedures of Hedo et al. (42). Eluates were pre-absorbed once with a mixture of control mouse ascites and protein A-Sepharose (Pharmacia) for 1 hour at 4° C. and twice with protein A-Sepharose alone for 1 hour at 4° C. Of each supernatant, 2.5×10$^4$ cpm were then mixed with 10 microliters monoclonal antibody (approximately 1 mg/ml) and protein A-Sepharose and incubated on a turntable overnight at 4° C. The beads were then washed four times with cold TBS containing 0.5% NP-40 and 0.2% SDS and were resuspended in electrophoresis sample buffer.

Gel Electrophoresis

SDS-polyacrylamide gel electrophoresis was performed according to the procedure of Laemmli (43). The immunoprecipitates and in vitro translation products were dissolved in sample buffer with or without 2-mercaptoethanol and then were applied to 10% poly-acrylamide gels. Autoradiography was performed on Kodak XAR-5 film in the presence of intensifying screens (DuPont Chemical Company).

Costransformation and Rosetting Assay

Mouse ψ-2 cells (44) were maintained in Dulbecco's modified Eagle's medium (DME) supplemented with 10% calf-serum (CS) (Gibco). ψ-2 cells were plated out at a density of 5×10$^5$ cells per 10 cm dish, 2 days before transformation. Calcium phosphate precipitates were prepared by the method of Graham and van der Eb (25), as modified by Wigler et al. (27). Precipitates were applied to the cells using 10 micrograms of carrier DNA and either 10 micrograms of T4-pMV7 or 10 micrograms of T8-pMV7. After 2 days, the cells were placed under selection in DME/10% CS and 500 micrograms/ml G418 (Geneticin; Gibco).

Rosetting assays to identify T4$^+$ or T8$^+$ colonies were performed on surviving colonies 1 week after growth in selective medium. After one rinse with phosphate-buffered saline (PBS), the plates were incubated with 2.5 ml of the purified monoclonal antibody OKT4A or OKT8 (1 mg/ml; Ortho) diluted at 1/500 in PBS containing 5% fetal calf serum (FCS) for 45 minutes at room temperature. Free antibody was removed from the plates with three gentle rinses in PBS. 6 ml of human erythrocytes conjugated with purified rabbit anti-mouse IgG antibody (2% v/v stock suspension, diluted 1/10 in PBS/5% FCS) were added and the plates were left at room temperature. After 45 minutes, free erythrocytes were gently aspirated and PBS was added prior to inspection. T4$^+$ and T8$^+$ ψ-2 clones were purified by colony isolation and characterized by flow cytometry and Northern blot analysis.

Recombinant Retrovirus Production and Infection

T4$^+$ and T8$^+$ ψ-2 clones were isolated which produce recombinant retrovirus stocks with titers of 10$^5$ cfu/ml. Viral stocks were prepared by adding 10 ml of fresh DME/10% CS to a near confluent monolayer of the T4$^+$ or T8$^+$ ψ-2 clones. After 24 hours, the medium was removed and filtered through a 0.45 micrometer filter (Millipore). For infection, 5×10$^5$ cells were incubated with 2 ml of viral supernatant (or a dilution) in the presence of 8 micrograms/ml polybrene (Aldrich). After 3 hours, 8 ml of fresh medium was added. 3 days after infection the cells were reseeded into DME/10% CS containing 500 micrograms/ml G418, grown for 2 weeks, scored for $G_{418}{}^r$ colonies, and screened for surface T4 or T8 expression using the in situ rosetting procedure or flow cytometry.

ψ-2 culture supernatants were used to infect mouse ψ-AM cells as described above. T4$^+$ or T8$^+$ adherent transformants were purified by the in situ rosetting assay followed by colony isolation; T4$^+$ or T8$^+$ non-adherent transformants were purified by fluorescence-activated cell sorting (FACS). Non-adherent human lymphoid cell lines (HSB2, RPMI-T cells; Raji—B cells) and adherent epithelial cells (HeLa) were infected by co-cultivation with T4$^+$ or T8$^+$ ψ-AM clones (pretreated with 10 micrograms/ml mitomycin-C for 2 hours; Sigma) and were purified.

Cell lines were selected for G418 resistance at a concentration of 1.5 mg/ml, except for HeLa cells which require 1 mg/ml, and fibroblasts which require 0.5 mg/ml. All cell cultures producing recombinant amphotrophic viruses (4-AM) were maintained under P3 containment conditions.

AIDS Virus

The prototype LAV strain of HTLV-III/LAV was obtained from J.-C. Cherman (Institut Pastuer, Paris; (45)). Virus inocula used in these studies were from the second to fifth passages of virus in our laboratory. Inocula are culture supernatants from HTLV-III/LAV-infected, phytohemagglutinin (PHA)-stimulated peripheral lymphocytes which were harvested by sequential centrifugation (300×g for 7 minutes followed by 1500×g for 20 minutes), and were stored in liquid nitrogen. For binding studies, virus was concentrated from culture supernatants, harvested as above, by ultracentrifugation at 90,000×g for 90 minutes over a 15% cushion of Renograffin (E. R. Squibb) in 0.01 M Tris, 0.15 M NaCl, 1 mM EDTA, pH 8.0.

Anti-HTLV-III/LAV Reagents

Serum with high levels of antibody to HTLV-III/LAV was obtained from a homosexual man with chronic lymphadenopathy, and its specificity by immunofluorescence (46), Western blot analysis (47), and radioimmunoprecipitation (48) has been described. Portions of the IgG fraction were coupled with fluorescein isothiocyanate (FITC; FITC:protein ratio of 10.7 micrograms/ml), horseradish peroxidase (HPO; type VI; Sigma) and agarose as described (47, 49, 50, 51). Conjugates of IgG from a nonimmune serum were prepared in parallel.

Reverse Transcriptase Assay

Magnesium-dependent, particulate reverse transcriptase (RT) activity was measured with a template primer of $(A)_n(dT)12-18$ (or $(dA)_n(dT)_{12-18}$ as the negative control) in the presence of 7.5 mM $Mg^{2+}$ (52).

Immunofluorescence Detection of Cytoplasmic AIDS Virus

Cultured cells ($1\times10^5$ in 0.1 ml) were centrifuged onto glass slides (Shandon Cytocentrifuge), fixed in 95% ethanol and 5% acetic acid at $-20°$ C. for 30 minutes, and rehydrated with three 10 minute changes of PBS (0.01 M $PO_4$, 0.15 M NaCl, pH 8.0). Slides were exposed to a 1/500 dilution of FITC-anti-HTLV-III/LAV (19 micrograms/ml) for 30 minutes at room temperature. The slides were then washed (three changes, 10 minutes each) and mounted under a coverslip with 50% glycerol in PBS. The slides were examined with an epi-illuminated Leitz Orthoplan microscope. at 630×power. Under these conditions, the FITC-anti-HTLV-III/LAV reagent is specific for HTLV-III/LAV. Uninfected PHA-stimulated cells, Epstein Barr (EB) virus-infected B cell lines, an adenovirus-infected cell line, several T cell lines, and HTLV-I and HTLV-II infected cell lines were not stained.

AIDS Virus Immunoassay (Antigen Capture Assay)

This is a sandwich immunoassay that has been described in detail (47). Briefly, culture supernatant is added to microtiter plate wells coated with anti-HTLV-III/LAV IgG. After the plates are washed, bound virus antigen is detected with HPO-anti-HTLV-III/LAV. This assay, which is at least as sensitive as the RT assay, is negative with culture supernatants from PHA-stimulated lymphocytes from numerous donors, EB virus-infected B cell lines, several T cell lines, polyclonal and cloned IL-2 dependent T cell lines, the myeloid line K562, as well as cell lines that harbor HTLV-I or HTLV-II. The cutoff $OD_{490}$ for discriminating a positive from a negative supernatant was determined in each run from the mean plus 2 SD of at least 10 replicative determinations on control (uninfected cell culture) supernatants harvested at the same time.

AIDS Virus Infectivity (ID-50) Assay

The microculture assay for the titration of infectious HTLV-III/LAV has been described in detail (47). Briefly, PHA-stimulated lymphocytes or cell lines ($2\times10^6$ cells/ml) are inoculated with serial 10-fold dilutions of virus inoculum and incubated for 18 hours at 37° C.

The cells were then washed and plated in microculture (10 to 20 cultures per dilution: $1\times10^5$ cells per culture in 0.25 ml medium). Every 4 days, 100 microliters of supernatant was removed and replaced with fresh medium. Supernatants were then assayed for viral antigen by the antigen capture assay as described above. Infectious virus titer (ID-50) is defined as the reciprocal of the dilution at which 50% of the cultures are positive for virus (47).

VSV Pseudotype Assay

Vesicular stomatitis virus (VSV, Indiana strain, wild type) was propagated in cells producing the retrovirus required for the envelope pseudotype as described (53). Hyperimmune neutralizing sheep anti-VSV serum was added to the harvested VSV to inactivate non-pseudotype virions. The pseudotype titers ranged between $10^4$ and $10^5$ PFU/ml. For the assay, $2\times10^5$ cells to be infected with VSV pseudotypes were plated in 30 mm diameter tissue culture wells. HeLa, NIH 3T3, and L cells were naturally adherent; all other cells types were attached by pretreatment of the substratum with 50 micrograms/ml poly-L-lysine. After virus adsorption for 1 hour, the cells were washed and $10^6$ mink CCL64 or bovine MDBK cells were added to each well. These cells provide excellent plaques for secondary VSV infection but are resistant to infection by pseudotype virions. After allowing the plaque indicator cells to settle and spread (approximately 90 minutes), the monolayers were overlaid with agar medium. VSV plaques were counted 2 days after infection. Anti-T4A monoclonal antibody (1:20), anti-HTLV-III serum (1:10), or anti-HTLV-I serum (1:10) were used to inhibit pseudotype plaque formation by pretreatment of cells 30 minutes before addition of pseudotypes as described by (54).

Syncytium Induction Assay $2\times10^5$ cells were co-cultivated with $2\times10^4$ H9 cells infected by and producing HTLV-III (55) in 10 mm diameter wells. The cultures were incubated at 37° C. and examined for syncytia formation after 18 hours as previously described (54, 56). Cells were five or more syncytia were scored as positive. Syncytium inhibition was assayed by adding anti-T4A monoclonal antibody (1:20) to the mixed cultures at the time of seeding.

Cytofluorometric Analysis and AIDS Virus Binding

The method has been described in detail (46). Briefly, cell surface T4 or T8 expression was detected by direct immunofluorescence with fluorescein-conjugated anti-T4A or anti-T8 monoclonal antibodies (OKT4A, OKT8). The diluent/wash buffer was 0.01 M $PO_4$, 0.15 M NaCl, pH 7.4, containing 0.1% bovine serum albumin, 2% v/v $AB^+$ human serum, and 0.01% $NaN_3$. All reagents were pretitered for optimal (saturating) binding. Cells ($5\times10^5$) were incubated in a 25 microliter dilution of monoclonal antibody for 30 minutes at 4° C. The cells were washed by centrifugation (300×g for 7 minutes), resuspended in 0.5 ml of 1% paraformaldehyde in saline, and analyzed with a fluorescence-activated cell sorter (FACS IV, Becton Dickinson). For HTLV-III/LAV binding, $5\times10^5$ cells were incubated with HTLV-III/LAV (500 ng in 10 microliters) for 30 minutes at 37° C. Washed cells were resuspended in 25 microliters of fluorescein-conjugated anti-HTLV-III/LAV for 30 minutes at 4° C. The cells were washed, resuspended in 1% paraformaldehyde, and analyzed by FACS as above. For inhibition of HTLV-III/LAV binding, cells were preincubated with anti-T4A or anti-T8 (20 ng in 20 microliters) for 30 minutes at 4° C. followed by addition of HTLV-III/LAV (500 ng in 10 microliters) for 30 minutes at 37° C. The cells were washed incubated with fluorescein-conjugated anti-HTLV-III/LAV, washed, resuspended in paraformaldehyde, and analyzed by FACS as above.

Cell Surface Radioiodination, Immunoprecipitation, and Gel Electrophoresis $T4^+$ NIH 3T3 transformants were surface radioiodinated by the lactoperoxidase technique (18) as follows: $4\times10^7$ cells were suspended in 1 ml of PBS containing 0.5 mM EDTA, 2 mCi $Na^{125}I$, and 20 micrograms lactoperoxidase. At times 0, 1, 5, 10, and 15 minutes, 10 microliters of 0.03% $H_2O_2$ were added. The reaction was carried out at 23° C. and was stopped at 20 minutes by 2 centrifugations in 50 volumes of cold PBS containing 10 mM NaI. Labeled cells were split into 4 tubes and incubated, as indicated, with HTLV-III/LAV (2 micrograms in 20 microliters) for 30 minutes at 37° C. Subsequent washes and manipulations were performed at 0° to 4° C. Washed cells were lysed by adding 1 ml of detergent lysing buffer (LB; 0.02 M Tris, 0.12 M NaCl, pH 8.0, containing 0.2 mM phenylethylsulfonylfluoride, 5 micrograms/ml aprotinin, 0.2 mM EGTA, 0.2 mM NaF, 0.2% sodium deoxycholate, and 0.5% (v/v) Nonidet P-40). Tubes were held on ice for 15 minutes, and nuclei were removed by centifugation at 3000×g for 20 minutes.

For absorptions, Sepharose conjugates of human anti-HTLV-III/LAV IgG, human nonimmune IgG, anti-T4A, and anti-T8 antibodies were prepared as described (48). Lysates were preabsorbed with 200 microliters of Sepharose-nonimmune human IgG for 1.5 hours with rotation, and then immunoprecipitated with 20 microliters of Sepharose conjugates (as indicated) for 3 hours with rotation. Sepharose absorbents were washed 3 times: once with LB; once with LB containing 0.5 M NaCl; and once with LB containing 0.1% sodium dodecyl sulfate (SDS). Absorbed material was eluted at 65° C. for 30 minutes with 20 microliters of sample buffer (0.01 M Tris, pH 8.0, containing 2% SDS, 5% 2-mercapto-ethanol (v/v), 25 micrograms bromphenol blue, and 10% glycerol (v/v). Electrophoresis was performed in a 3.3–20% gradient polyacrylamide gel with a 3% stacking gel (57), and autoradiographs were developed with Kodak XAR-5 film.

Virus Inhibition Assay $2 \times 10^5$ T4$^+$ JM T cells were exposed to AIDS virus at 0 minutes. The inhibitors ammonium chloride (20 mM) or amantadine (20 mM) were added at various times during the course of virus infection (0 minutes, 30 minutes, and 60 minutes). After 6hours, cells were washed and replated in fresh medium (RPMI/10% FCS). The effect of these agents on AIDS virus infection was determined 5 days post infection. The fraction of infected cells in the cultures expressing viral antigens was determined by immunofluorescence microscopy as described above (58).

RNA Isolation and Northern Blot Hybridizations

Total RNA was isolated from cells by homogenation in 4M guanidinium thiocyanate, followed by ultracentrifugation through a 5.7 M CsCl cushion (28). Poly(A)$^+$ selection was achieved by oligo(dT)-cellulose chromatography (Type 3, Collaborative Research) (29).

RNA was electrophoresed through a 1% agarose-formaldhyde gel (39) and transferred onto Hybond (Amersham). Northern blot hybridization was performed according to the procedures supplied by the manufacturer. Probes were nick-translated to a specific activity of 0.5–1× $10^9$ cpm/microgram with $\alpha^{32}$P-labeled deoxynucleotide triphosphates (59).

RESULTS

Isolation of a T4 cDNA

The strategy used to isolate a T4 cDNA initially involved constructing L cell transformants that express T4 on their surface. cDNA synthesized from the mRNA of a T4$^+$ transformed fibroblast was enriched by substractive hybridization and used as a probe to isolate a cDNA encoding T4 from a cDNA library made from the mRNA of peripheral T lymphocytes. The identity of T4$^+$ cDNA clones was determined by Northern and Southern blot analyses, and ultimately by the ability of these clones to transfer the T4$^+$ phenotype to recipient cells. Similar techniques have previously been employed to isolate the gene encoding the T8 protein (20).

Figure 1:
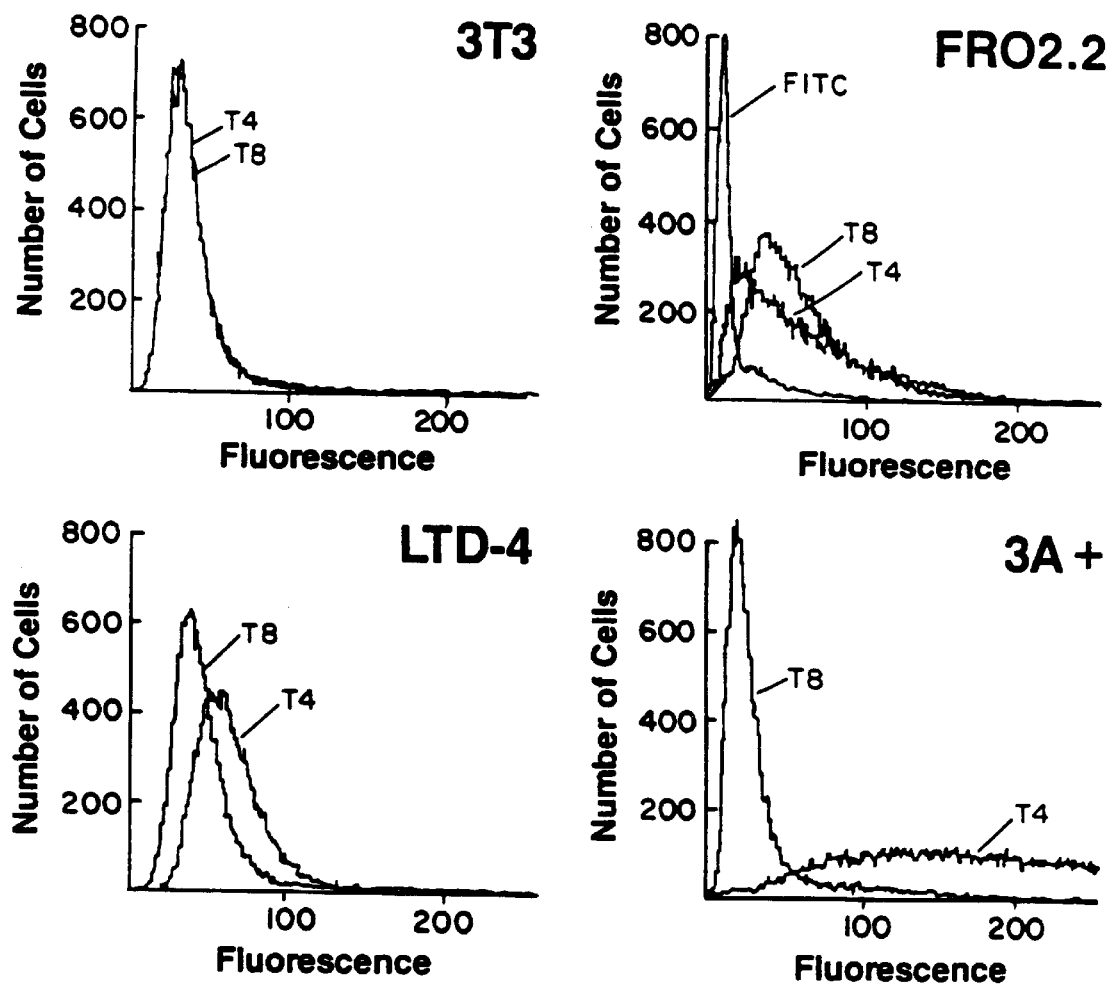
FIG. 1. Cytofluorographic Patterns of Indirect Immunofluorescent Staining with OKT̄4 and OKT̄8

Mouse L cells deficient in thymidine kinase (tk) were cotransformed with genomic DNA from the T cell leukemic cell line HUT-102 along with the tk-containing plasmid, pTK (25, 26). tk$^+$ L cell transformants expressing T cell surface proteins were identified by an in situ resetting assay. tk$^+$ colonies were exposed to mouse monoclonal antibodies directed against T4 and were then incubated with red blood cells coupled with rabbit anti-mouse immunoglobulin. T4$^+$ transformants are visibly red by virtue of their specific association with red blood cells. In this manner, one primary T4$^+$ transformant, LTD-4, was obtained. The expression of the T4 molecule by this clone was independently verified by cytofluorometric analysis (FIG. 1).

The mRNA population of the T4$^+$ transformant, LTD-4, should differ from that of an untransformed L cell only in the expression of newly transformed genes. These sequences were enriched for by annealing highly radioactive cDNA prepared from poly(A)$^+$ RNA of the T4 transformant with a vast excess of RNA from an untransformed L cell (32, 60). cDNA incapable of hybridizing, even at high Rot values, was isolated by hydroxyapatite chromatography and used to screen a human peripheral T cell cDNA library constructed in the lambda cloning vector gt10. Four weakly hybridizing plaques were identified, plaque-purified and analyzed for the presence of T4 sequences.

To determine whether any of these clones encoded T4, Northern blot analyses were initially performed with RNA from T4$^+$ and T4$^-$ peripheral T cells, leukemias, thymocytes, L cell transformants and nonlymphoid cells (FIG. 2). One of the four clones hybridized to an RNA present only in T4$^+$ cells. This clone detects a 3 kb RNA present in the T4$^+$ transformant, LTD-4, which is also present in a population of T4$^+$ peripheral lymphocytes, a variety of T4$^+$ leukemic cell lines, and thymocytes. No hybridization was observed with RNA from untransformed fibroblasts, T4$^-$ peripheral lymphocytes, HeLa cells, or human neuroblastoma cells.

The pattern of expression of RNA detected by this clone is consistent with the possibility that it encodes T4. However, this cDNA is only 0.6 kb in length but hybridizes to a 3 kb mRNA. Therefore, the human peripheral T cell cDNA library was rescreened and one clone (pT4B) was obtained which contained a 3 kb insert, close in size to that of the mature messenger RNA. Restriction maps of this clone are shown in FIGS. 3A and 3B.

Genomic Blot Analysis

Southern blot experiments (37) were next performed to demonstrate that the isolated cDNA clone hybridized with DNA from the T4$^+$ transformant as well as human DNA, but not with untransformed mouse L cell DNA (FIG. 4). Genomic DNA from a variety of human cells reveals a set of five hybridizing fragments after cleavage with the enzyme BamHI. As expected, T4 sequences can be detected in the transformant LTD-4, but not in untransformed L cell DNA. The BamHI fragment closest to the 3' end of the gene (6.6 kb) is not present in LTD-4, presumably as a consequence of the integration event. Moreover, no gross rearrangements are apparent at this coarse level of analysis when comparing DNA from lymphoid and nonlymphoid cells. The sum of the molecular weights of the hybridizing fragments is 33 kb, suggesting that the T4 gene is quite large. A complete set of genomic clones spanning this region was obtained (see below) and the BamHI fragments were ordered by restriction analysis of these clones (FIG. 3A), confirming that the gene is large and must contain introns of significant lengths.

Expression of the T4 cDNA in Transformed Mouse Fibroblasts

Further evidence that the isolated cDNA encodes T4 would be provided if this clone could convert fibroblasts to the T4+ phenotype after transformation. The T4 gene in chromosomal DNA is large and spans several genomic clones. Therefore, the cDNA clone was introduced into two retroviral expression vectors, pVcos7 and pMV6kt/neo, which contain the Moloney murine leukemia virus long terminal repeats (LTRs) flanking a single EcoRI cloning site (FIGS. 3C-1 and 3C-2). The 5'-LTR promotes transcription through the cloning site and the 3'-LTR contains sequences necessary for cleavage and polyadenylation. The vector pMV6tk/neo also contains the tk promoter fused to the coding region of the neomycin phosphotransferase gene. The construct employing pVcos7 requires transformation with an unlinked selectable marker, whereas pMV6tk/neo carries the neomycin resistance marker, which permits linked cotransformation. Neo colonies of NIH 3T3 cells obtained after transformation were selected by their ability to grow in media containing the neomycin analogue G418, and were screened using the rosetting procedure to detect the expression of T4 on the cell surface. Approximately 50% of the G418 colonies obtained with pVcos7 and 75% of the colonies obtained with pMV6tk/neo were positive for T4 in this assay. Rosette-positive colonies were further analyzed by cytofluorometry to confirm that T4 is expressed on the transformed cell surface (FIG. 1).

Metabolic protein labeling experiments were performed which demonstrate that the T4+ transformed fibroblast and the T lymphocyte express a T4 protein of identical molecular weight. Untransformed NIH 3T3 cells, T4+ transformants and T lymphocytes were labeled for 12 hours in the presence of L-[$^{35}$S]-methionine (41). The cells were detergent solubilized and the lysate was passed over lentil lectin columns to enrich for glycoproteins (42). The bound glycoprotein fraction was eluted and immunoprecipitated with monoclonal antibodies directed against T4 (FIG. 5). Under reducing conditions, a glycoprotein migrating at a relative molecular mass of 55 kd is detected in extracts from T lymphocytes and two independent T4+ transformants.

This protein is not detected in control 3T3 fibroblasts. Under nonreducing conditions, a 51 kd glycoprotein is immunoprecipitated with anti-T4 in T cells and in the transformed fibroblasts.

These experiments demonstrate that the transformants express a 55 kd glycoprotein immunoprecipitated with anti-T4 which is identical in size to that expressed on the surface of T lymphocytes. Thus, Northern and Southern analyses using the isolated cDNA, taken together with the ability of this cDNA to confer the T4+ phenotype to mouse fibroblasts, indicate that the entire coding sequence of the T cell surface protein T4 had been cloned.

Nucleotide Sequence of the T4 cDNA and the Deduced Protein Sequence

The complete nucleotide sequence of the T4 coding region was determined by sequencing both strands of the 3 kb cDNA insert using the dideoxy termination method (35, 36). The complete nucleoticle sequence and the predicted protein sequence are shown in FIG. 6. The longest open reading frame begins at position 76 with a methionine codon surrounded by the initiation consensus sequence PurNNAT-GPur (61). This reading frame extends 1374 nucleotides, encoding a polypeptide containing 458 amino acids. The contiguity of this reading frame was confirmed by inserting this cDNA into the RNA expression vector pSP6 (40). RNA synthesized from this vector, when translated in vitro, directs the synthesis of an unmodified 51 kd protein, the precise molecular weight predicted from the nucleotide sequence (FIG. 7).

T4 is comprised of a leader sequence, four tandem variable-joining (VJ)-like regions, and a membrane-spanning domain each sharing homology with corresponding regions of different members of the immunoglobulin gene family (62, 63) (FIGS. 6 and 8). A stretch of hydrophobic residues, corresponding to a leader peptide predicted by a Kyte-Dolittle (64) hydropathicity plot, immediately follows the initiation codon. Although the exact position at which the native T4 protein is processed cannot be determined, it is contemplated that cleavage occurs just after the threonine at positions 1based on known cleavage patterns (65). Therefore, the signal peptide contains 23 amino acids and the processed T4 protein consists of 435 residues.

Residues 1–94 of the mature protein share both amino acid and structural homology with, the immunoglobulin light chain variable domain (FIG. 9A). The overall homology of this domain with immunoglobulin variable regions is 32%. Sequence comparison between the V regions of light chain immunoglobulins and the N-terminal V-like region (V1) of T4 demonstrates that eight out of 14 invariant residues are conserved (66). This domain contains two cysteine residues, separated by 67 amino acids, whose positions and spacing are analogous to that found in light chain immunoglobulins and related molecules (67). These cysteines may be capable of forming the conserved intrastrand disulphide bond characteristic of V domains. This suggestion is supported by our observation that T4 migrates more rapidly under nonreducing conditions than under reducing conditions, consistent with the formation of at least one intrastrand linkage (FIG. 5, lanes e and f).

Aside from homologies at the level of individual amino acids, the V1 domain of T4 shares structural features with immunoglobulin variable regions. Immunoglobulin variable and constant domains fold in a characteristic pattern in which a series of antiparallel β-strands fold to form two β-sheets (67, 68). These β-sheets are held together both by a disulphide bridge and by characteristic hydrophobic interactions. To determine how the predicted secondary structure of the V-like domain of T4 compares with the structure of the V domains of light chain immunoglobulins, two-dimensional structural alignments were performed. Also, a plot of probable β-strands and β-turns in these sequences using the empirically derived algorithm of Chou and Fasman (69) was obtained. These analyses suggest the presence of seven β-strands within the V-like domain of T4 which closely match those found in the immunoglobulin V domain (FIG. 9A). The two conserved cysteines of T4 are found within β-strands B and F, matching exactly the positions of the cysteines in the V region known to form the conserved disulphide bond in immunoglobulin. A tryptophan residue lies 12 amino acids downstream of the first cysteine and a tyrosine residue is situated two amino acids before the second cysteine. These residues are highly characteristic of β-strands C and F, respectively in light chain V regions. In addition, an aspartate residue is found six amino acids before the second cysteine, and an arginine residue lies at the base of β-strand D. These charged residues are highly characteristic of V domains (67). Finally, patches of alternating hydrophobic residues are present throughout the β-strands, which strengthen the interaction of the two β-sheets.

The V1 domain of T4 is followed by a stretch of amino acid residues bearing significant homology to the joining (J)regions of immunoglobulins and T cell antigen receptors. In FIG. 9B, this J-like region of T4 is aligned with the consensus joining sequences of immunoglobulin light chains and the two chains of the T cell antigen receptor. This J-like region is followed by a 265 amino acid stretch which may be structurally divided into three additional VJ-like domains with statistically significant sequence and structural homology to prototype immunoglobulin VJ regions (FIGS. 6 and 8). Additionally, this sequence contains two potential N-linked glycosylation sites (Asn-Leu-Thr; FIG. 6).

The extracellular domain is followed by a putative transmembrane sequence, predicted by a hydropathicity plot (64), which contains only hydrophobic and neutral amino acid residues. This segment bears striking homology to the transmembrane exon of the β-chains of class II major histocompatibility proteins (FIG. 9C). Alignment of the transmembrane regions of T4 and MHC class II β-chains reveals 48% homology without gaps. Following the membrane-spanning segment, a highly charged sequence of 40 amino acids comprise the cytoplasmic domain (FIGS. 6 and 8).

The T4 Gene: Chromosomal Location and Intron-Exon Positions

The T4 cDNA was used to determine the chromosomal location of the T4 gene by analyzing its segregation pattern in a panel of mouse-human somatic cell hybrids and by in situ hybridization to human metaphase chromosomes (101). Genomic blot experiments and in situ hybridization indicate that the T4 gene resides on the short arm of human chromosome 12, between regions 12p12 and 12pter.

A set of overlapping genomic clones spanning the T4 gene was obtained by screening human genomic libraries constructed in the lambda cloning vectors Charon 4 and EMLB-3 (31) with a radiolabeled pT4B cDNA insert (70). Characterization of these clones by both restriction and Southern blot analyses indicated that they contained the entire T4 coding sequence. The complete intron-exon organization of the T4 gene was then determined by sequencing specific fragments of the genomic clones using the dideoxy termination procedure (35, 36).

The T4 gene is comprised of 9 exons split by 8 introns as shown in FIGS. 8 and 10. The first exon contains the 5'-untranslated region and the leader segment. The first variable-like domain, $V_1$, is split by a large intron located at nucleotide position 289 (FIG. 6). Therefore, the $V_1J_1$ domain is encoded by the second and third exons and the $V_2J_2$, $V_3J_3$, $V_4J_4$, and transmembrane (TM) domains are each encoded by separate exons (exons 4–7). The cytoplasmic domain (CYT) is split by an intron and the last portion of the cytoplasmic domain and the 3'-untranslated region are encoded by the ninth exon.

The Construction of T4+ and T8+ Transformed Cells

The experimental approach used to study the role of T4 in AIDS virus infection initially involved the introduction of the T4 gene into T4⁻ cell lines incapable of supporting viral infection. The transformed cells were then tested for susceptibility to AIDS virus, followed by studies on the mechanism by which T4 mediates viral infection.

A full length cDNA clone encoding the surface protein T4 was subcloned into the retroviral expression vector, pMV7. The expression vector, pMV7 (FIGS. 11A-1 and 11A-2), contains two directly repeated Moloney murine sarcoma virus long terminal repeats (LTRS) which flank a single EcoRI cloning site. The 5'-LTR constitutively promotes transcription through the cloning site, whereas the 3'-LTR provides sequences necessary for cleavage and polyadenylation of the RNA. In addition, pMV7 contains the herpesvirus thymidine kinase promoter (tk) fused to the coding region of the bacterial neomycin phosphotransferase gene (neo), a dominant selectable marker, permitting linked cotransformation and infection.

T4-pMV7 was introduced into ψ-2 and ψ-AM cells, NIH 3T3 cell lines containing defective ecotropic and amphotropic proviruses, respectively (FIG. 11B) (44,59). Both cell lines are incapable of encapsidating endogenous viral RNA but can provide all obligate trans viral functions. Stable transfection of these cell lines with T4-pMV7 results in the production of recombinant retroviral stocks encoding T4 which are free of helper virus. These pure viral stocks can then be used to efficiently introduce T4 sequences into both mouse and human cells without the production of retrovirus by the target cell.

Briefly, T4-pMV7 DNA was introduced into ψ-2 cells using the procedure of DNA-mediated gene transfer (FIG. 11B) (25, 27). Neo⁺ positive colonies were selected by their ability to grow in media containing the neomycin analog G418 (Geneticin*) and screened for the expression of T4 on the cell surface using an in situ rosetting assay (20, 70). Colonies of transfected ψ-2 cells expressing T4 were then identified which produce recombinant retrovirus in titers of $10^5$ cfu/ml. T4⁺ ψ-2 clones were then used to generate retroviruses capable of infecting mouse ψ-AM cells. T4 expressing ψ-AM clones were isolated which yield recombinant retroviral titers of $10^4$ cfu/ml. T4⁺ human transformants were generated by co-cultivation of cells with mitomycin-C treated or ψ-AM clones (FIG. 11B). T4⁺ transformants were subsequently analyzed by Northern blot analysis and flow cytometry to confirm that T4 is expressed and is present on the cell surface. Control cell lines expressing the surface protein T8 were constructed in an analogous manner.

T4 is Essential for AIDS Virus Infection

To initially determine whether the presence of the T4 protein on the surface of a human lymphocyte is sufficient to render the cell susceptible to AIDS virus infection, transformants of the primitive T cell leukemic line, HSB2 (71), which expresses only the early T lymphocyte proteins T1 and T11 on its surface, were constructed. HSB2 expresses neither T4 nor T8, nor does it express the T cell antigen receptor or the associated complex of T3 proteins. Transformants of HSB2 which express either the T4 or T8 proteins on the cell surface were selected and used to determine the susceptibility of these cell lines to AIDS virus infection. Several different experimental approaches were employed to assess AIDS virus infection, including expression of reverse transcriptase (52), expression of virus in the cytoplasm of the cell by immunofluorescence microscopy (46), detection of viral antigens in the culture supernatant using an immunoassay (47), as well as production of infectious virions by supernate subculture with phytohemagglutinin (PHA)-stimulated peripheral lymphocytes (46). Using these assays, evidence of AIDS virus infection of the HSB2 cell line was not observed (Table I).

TABLE I

Susceptibility of T4+ and T8+ Human Transformants to AIDS Virus Infection

| HUMAN CELL | Maximum Reverse Transcriptase | Cytoplasmic Virus | Supernate Viral Ag | Supernate Subculture | Syncytium Induction | VSV (AIDS) Pseudotype Infection | Virus Binding |
|---|---|---|---|---|---|---|---|
| CEM(T4+) | 675023 | + | + | + | + | + | + |
| HSB2 | 4245 | – | – | – | – | – | – |
| HSB2-T8+ | 4460 | – | – | – | – | – | – |
| HSB2-T4+ | 190915 | + | + | + | + | + | + |
| Raji | ND | ND | ND | ND | – | – | ND |
| Raji-T8+ | 5595 | – | – | – | – | – | – |
| Raji-T4+ | 103500 | + | + | + | + | + | + |
| HeLa | 6438 | – | – | – | – | – | – |
| HeLa-T8+ | 4875 | – | – | – | – | ND | – |
| HeLa-T4 | 48125 | + | + | + | + | + | + |

$5 \times 10^6$ cells were inoculated with AIDS virus, incubated at 37° C. for 24 hours, washed, and replated in fresh media. Cells and supernatants were removed at days 3, 6, 9, 12, 16, 20, 24, and 28 and used in four virus detection assays: reverse transcriptase, cytoplasmic virus, supernate viral antigen, and supernate subculture.
The results of the pseudotype infection experiments are expressed as follows: + ($\geq 10^3$ PFU/ml); – (10 PFU/ml); ND, not determined.

In addition, it has been previously demonstrated that extensive cell fusion occurs when uninfected human cells bearing receptors for AIDS virus are co-cultivated with cells producing AIDS virus (54). In this assay, there is no induction of syncytia when HSB2 cells are mixed with AIDS virus-producing H9 cells (Table I), although abundant syncytia are formed with HTLV-I and HTLV-II producing cells (data not shown).

Finally, viral entry was tested for using pseudotypes of vesicular stomatitis virus (VSV) bearing the envelope glycoproteins of the AIDS virus (Table I) (53, 54). When cells infected with AIDS virus are superinfected with VSV, a proportion of the progeny vsv assemble sufficient AIDS virus envelope glycoprotein to resist neutralization by hyperimmune anti-VSV serum. The host range of these VSV (AIDS) pseudotype virions is restricted to cells expressing receptors specific to the AIDS virus. Following penetration of the cell and uncoating of the virion, the transcapsidated VSV genome replicates to produce non-pseudotype particles. During the secondary infection, progeny VSV released from infected cells penetrate and destroy neighboring indicator cells resistant to VSV (AIDS) pseudotype infection (mink CCL64 or bovine MDBK cells), resulting in the formation of VSV plaques which are then scored. Thus, infection with VSV (AIDS) pseudotypes provides a quantitiative cytopathic plaque assay for viral entry (54). In this assay, no plaques over background were observed when HSB2 cells were exposed to VSV (AIDS) pseudotypes (Table I). In control experiments with pseudotypes of VSV RNA encapsidated in an HTLV-I envelope (VSV (HTLV-I)), numerous plaques were observed demonstrating that the HSB2 cell, which bears HTLV receptors, is capable of replicating VSV efficiently. These observations demonstrate that the VSV genome encapsidated in an AIDS virus envelope is incapable of entering HSB2 cells.

Whether the introduction of a functional T4 cDNA into HSB2 would render this cell susceptible to AIDS virus infection was next studied (Table I). Exposure of HSB2 -T4+ transformants to AIDS virus results in a productive viral infection as determined by expression of reverse transcriptase activity (52), expression of virus in the cytoplasm of the cell by immunofluorescence microscopy (46), detection of viral antigen in the culture supernatant using an immunoassay (47), as well as the production of infectious virus by supernate subculture with PHA-stimulated lymphocytes (Table I) (46). Control HSB2 -T8+ cells were consistently negative in each of the assays.

In addition, the efficiency with which different T4+ T cells are infected with AIDS virus was also examined. HSB2 -T4+ and HSB2 -T8+ transformants, the naturally-isolated T4+ T cell line CEM, as well as PHA-stimulated peripheral lymphocytes were exposed to serial 10-fold dilutions of AIDS virus, washed, and plated in microculture. The frequency of infected cultures was then determined using an immunoassay 12 days after exposure to virus (FIG. 12) (47). In this manner, the titer of AIDS virus required to infect 50% of the exposed cultures (ID-50) was defined. The ID-50 of PHA-stimulated peripheral lymphocytes is 2–3 orders of magnitude greater than that observed for either naturally-isolated or transformed T4+ cell lines. The efficiency of infection of HSB2 -T4+ cells is about 10 fold higher than that observed for the naturally-isolated T4+ T cell line CEM (FIG. 12). Control HSB2 -T8+ cells are net susceptible to infection even at the highest virus titers examined.

The ability of HSB2 -T4+ cells to support both syncytia formation and the replication of VSV (AIDS) pseudotypes was also studied. When HSB2 -T4+ cells are co-cultivated with AIDS virus producing H9 cells, syncytia formation is readily observed within 18 hours (Tables I and II). Moreover, syncytium induction is abolished by pretreating cultures with anti-T4A monoclonal antibody (Table II). Finally, when HSB2 -T4+ cells are exposed to VSV (AIDS) pseudotypes, infectious VSV particles are produced which destroy neighboring indicator cells (Tables I and III). Furthermore, plaque formation is inhibited by pretreatment with either anti-AIDS virus antibody or anti-T4A monoclonal antibody (Table III). Control HSB2 -T8+ cells are consistently negative in each of the seven assays employed to detect AIDS virus infection (Tables I, II, and III). These observations provide genetic evidence that in an immature human T lymphocyte, the mere presence of the T4 protein provides an essential function required for AIDS virus infection.

TABLE II

Induction of Syncytia in T4+ Human Transformants

| HUMAN CELLS | SYNCYTIUM INDUCTION | |
|---|---|---|
| | H9/AIDS | H9/AIDS + αT4A |
| JM (T4+) | +++++ | — |
| 8166 (T4+) | +++++ | — |
| HSB2 | — | ND |
| HSB2-T8+ | — | ND |
| HSB2-T4+ | ++ | — |
| Raji | — | ND |
| Raji-T8+ | — | ND |
| Raji-T4+ | +++ | — |
| HeLa | — | ND |
| HeLa-T8+ | — | ND |
| HeLa-T4+ | +++++ | — |

$2 \times 10^5$ cells were co-cultivated with $2 \times 10^4$ AIDS virus-producing H9 cells (H9/AIDS) and incubated at 37° C. The cultures were examined for syncytia formation after 18 hours. The results are expressed as the approximate percentage of nuclei contained within syncytia: — (no syncytia); ++ (25%); +++ (50%) +++++ (90%); ND (not determined). Syncytium inhibition was assayed by addinganti-T4A monoclonal antibody (αT4A; 1:20) to the mixed cultures at the time of seeding. The naturally-isolated T4+ T cell lines JM and 8166 served as positive controls in these studies.

TABLE III

VSV Pseudotype Cytopathic Plaque Assay on T4+ and T8+ Human Transformants

| | VSV PSEUDOTYPE TITER (PFU/ml) | | | | |
|---|---|---|---|---|---|
| | VSV (HTLV-I) | | VSV (AIDS) | | |
| HUMAN CELLS | | + αHTLV-I | | + αAIDS | + αT4A |
| CEM (T4+) | 20,000 | 50 | 42,000 | 50 | 200 |
| HSB2-T8+ | 10,000 | 50 | 0 | ND | ND |
| HSB2-T4+ | 12,000 | 50 | 1,000 | 100 | 300 |
| Raji-T8+ | 5,000 | ND | 0 | ND | ND |
| Raji-T4+ | 5,000 | 50 | 1,500 | 25 | 150 |
| HeLa | 10,000 | ND | 0 | ND | ND |
| HeLa-T4+ | 10,000 | 50 | 17,000 | 50 | 200 |

$2 \times 10^5$ cells were incubated with VSV (AIDS) pseudotypes (53, 54) for 1 hour at 37° C. The cells were then washed and $1 \times 10^6$ mink CCL64 or bovine MDBK plaque indicator cells, permissive to VSV infection but resistant to VSV (AIDS), were added to each well. The cultures were then overlaid with agar medium and scored for VSV plaques two days post infection. Anti-T4A monoclonal antibody (αT4A; 1:20) or anti-AIDS virus serum (αAIDS; 1:10) were used to inhibit VSV (AIDS) pseudotype plaque formation be pretreatment of cells 30 minutes before exposure to pseudotypes (54). VSV (HTLV-I) pseudotypes, which plate on a wide variety of human cell types (54), were used as controls in these experiments. Anti-HTLV-I serum (1:10) was used to block VSV (HTLV-I) pseudotype plaque formation. The results are expressed as PFU/ml; ND (not determined).

AIDS Virus Infection Is Not Restricted to T Lymphocytes

A functional T4 cDNA was introduced into two human non-T cell lines: HeLa, an epithelial cell line derived from a cervical carcinoma (72), and Raji, a B lymphoblastoid cell line derived from a patient with Burkitt's lymphoma (73) (FIG. 11B). Prior to retrovirus-mediated gene transfer, these cell lines do not express surface T4 protein or T4 mRNA, nor are they susceptible to AIDS virus infection (Table I). In addition, the parental cell lines do not support the induction of syncytium nor the plating of VSV (AIDS) pseudotypes (Tables I, II and III).

In contrast, T4+ Raji and HeLa transformants support AIDS virus infection by all of the criteria previously described (Table I). The efficiency with which Raji-T4+ cells can be infected with AI I)S virus approximates that of HSB2 -T4+ cells and is about 10 fold higher than the efficiency of infection of the naturally-isolated T4+ T cell line CEM (FIG. 12). Moreover, upon co-cultivation with AIDS virus-producing H9 cells, Raji-T4+ and HeLa-T4+ cells support the induction of syncytia which is abolished by pretreating cultures with anti-T4A monoclonal antibody (Tables I and II; FIG. 13). In addition, exposure of these cells to VSV (AIDS) pseudotypes results in the production of infectious VSV and the formation of plaques which are inhibited by pretreatment with anti-AIDS virus antibody or anti-T4A monoclonal antibody (Tables I and III). Control Raji-T8+ and HeLa-T8+ transformants are consistently negative in each of these assays (Tables I, II, and III).

Therefore, the introduction of a functional T4 gene into either human T lymphocytes, B lymphocytes, or epithelial cells is sufficient to render such cells susceptible-to AIDS virus infection. Taken together, these observations indicate that the T4+ T cell tropism observed in vivo is a consequence of the restricted expression of the T4 molecule and not the nature of the cell type in which it is expressed.

AIDS Virus Binds to Surface T4 Protein

The previous experiments provide genetic evidence that T4 expression is required for AIDS virus infection but do not provide information on the role of this molecule in the viral life cycle. The observation that surface expression of T4 is necessary for AIDS virus infection suggests that T4 is the AIDS virus receptor. Cytofluorometry was therefore used to examine the binding of AIDS virus to the surfaces of T4+ and T8+ transformed human cells (Table I; FIG. 14). HSB2, Raji, and HeLa cells, and the T4+ or T8+ transformants, were incubated with AIDS virus. Following viral absorption, the cells were washed, exposed to fluorescein-conjugated anti-AIDS virus antibody, and analyzed by flow cytometry. This assay indicated that the AIDS virus binds efficiently and specifically to the human transformants expressing surface T4, but not to the T4− parental cells nor to the T8+ transformants (FIGS. 14B-1–14B-3; Table I). The binding of AIDS virus to the T4+ cells is abolished by preincubation with anti-T4A monoclonal antibody but not by preincubation with anti-T8 monoclonal antibody (FIGS. 14C-1–14C-3). Moreover, when T4+ transformed cells are exposed to AIDS virus, the T4 glycoprotein coprecipitates with the viral envelope glycoprotein, suggesting a direct physical association between these molecules (data not shown). These results indicate that the AIDS virus binds to the T4 molecule on the cell surface and that this binding is independent of other T cell-specific proteins since binding occurs to all T4+ cell types examined.

Previous studies have described two distinct pathways of entry for enveloped viruses (74, 75, 76, 77). Some viruses fuse directly with the plasma membrane, releasing their nucleocapsids into the cytoplasm, whereas others are internalized by receptor-mediated endocytosis. The acidic environment of the endosome then facilitates fusion of the viral envelope with the limiting membrane of the vacuole. Infection by viruses which enter cells via the endocytic pathway can be inhibited by treating cells with agents such as weak bases which deacidify the endosome (58, 78, 79, 80). In the presence of ammonium chloride, fusion is blocked in the endosome but lysosomal degradation still proceeds at a reduced rate (80).

The effect of ammonium chloride on AIDS virus infection of the T4+ T cell line JM was therefore examined. In the absence of ammonium chloride, over 50% of JM cells exposed to AIDS virus express viral antigens five days after infection as determined by immunofluorescence microscopy. If JM cells are exposed to ammonium chloride (for 6 hours) either at the time of addition of virus or within 30 minutes after the addition of virus, greater than 95% inhibition of viral infection was observed. However, if cells were treated with ammonium chloride one hour after the addition of virus, no inhibition of infection was observed, a finding consistent with the kinetics of viral entry described for other viruses which enter cells via receptor-mediated endocytosis. Finally, the ammonium chloride effect was completely reversible. Cells exposed to ammonium chloride for one hour, and then washed free of the compound and exposed to AIDS virus, supported control levels of viral infection. These results are consistent with previous observations that upon removal of ammonium chloride, the pH of the endosome returns to the original low values within 1–2 minutes (78, 80). Similar results with amantadine, a compound which deacidifies the endosome, were obtained.

These results are consistent with a mechanism of viral entry which involves endocytosis of the T4-AIDS virus complex and low pH-induced fusion of the viral envelope with the limiting membrane of the endosome, releasing the viral nucleocapsid into the cytoplasm of the cell.

T4 mRNA is Expressed in the Brain

In addition to the disruption of the cellular immune system, AIDS is frequently accompanied by central nervous system (CNS) disorders which are thought to be the consequence of the direct infection of brain cells by the AIDS virus (81). It was therefore of interest to determine whether T4 is expressed in cells within the CNS, thereby providing an explanation for the neurotropic properties of the virus. Northern blot analyses of RNA prepared from both human and mouse brains were performed to determine whether T4 mRNA sequences are expressed in the CNS (FIG. 15). Poly(A)+ RNA derived from human cerebral cortex contains two distinct T4 mRNAs with molecular weights of approximately 3 and 1.8 kb (FIG. 15A). The weaker 3 kb RNA is identical in size to the mRNA expressed by two T4+ leukemic cell lines, U937 (monocytic cell line) and Jurkat (T cell line), as well as by peripheral T lymphocytes. The smaller, more abundant 1.8 kb mRNA absent from T lymphocytes could result from alternative splicing or alternative 5' or 3' termini.

A more careful analysis of the localization of T4 mRNA was performed by isolating poly(A)+ RNA from specific regions of the mouse brain (FIG. 15B). Hybridization with radiolabeled cDNA encoding the murine homologue of T4, L3T4, reveals an intense 2.2 kb mRNA in mouse forebrain which is absent from hindbrain samples. The 2.2 kb L3T4 mRNA is detectable in the cortex, hypothalamus, and is most abundant in the stratum, but is absent from the cerebellum, brain stem, or spinal cord (data not shown). This 2.2 kb mRNA detected in the CNS is approximately 1 kb smaller than the 3.2 kb mRNA encoding L3T4 in thymocytes (FIG. 15B). These results indicate that the neurotropism displayed by the AIDs virus is likely to be the result of surface expression of the T4 molecule on brain cells. The level of mRNA detected in forebrain is about 1/30th the level in thymocytes. This may reflect low level expression by a large number of cells or higher levels of expression by a small subpopulation of cells. It is not known at present whether T4 is expressed by neurons or supporting cells. The presence of a variant transcript in the CNS, however, makes it unlikely that the T4 mRNA in brain is expressed by the rare invading T lymphocyte.

Discussion

The segregation of T4 and T8 with functionally distinct subsets of T cells suggests that these molecules may be important in the interaction of T lymphocytes with appropriate target cells. As a first step in understanding the specific role of these proteins, cDNA clones were obtained of both the T4 and T8 molecules and their nucleotide sequences were determined (20, 70). Comparison of the deduced protein sequences of T4 and T8 indicates that these molecules share significant sequence and structural homology with immunoglobulin variable (V) domains and as members of the immunoglobulin supergene family. However, the N-terminal V-like domains of T4 and T8 are quite different: they share only 28% homology and are therefore less homologous to each other than each is to immunoglobulin light chains (FIG. 9A). Moreover, the regions of maximum conservation between T4 and T8 are also the regions of strongest homology to immunoglobulin and T cell receptor V regions. Thus, the immunoglobulin-like domains of these two molecules, although structurally similar, show significant sequence divergence consistent with the hypothesis that they recognize different molecules on different subsets of target cells.

The V-like region structural homology shared by the N-terminal domains of T4 and T8 may be of particular relevance to the functions of these proteins. Virtually all members of the immunoglobulin supergene family participate in the immune response (62). Moreover, the individual members of this family show a strong tendency to associate with each other to form dimers. This association is apparent in the interaction of the heavy and light chains of immunoglobulin, the alpha and beta chains of the T cell antigen receptor, $\beta_2$-microglobulin and class I MHC proteins and the alpha and beta chains of class II MHC molecules. The T8 glycoprotein forms a disulphide bond with T6, a presumed MHC-like molecule, on the surface of thymocytes (82), and exists as multimers of the 32 kd subunit on peripheral T lymphocytes (83). The presence of four V-like domains in T4 indicates that these regions associate with one another as well as with specific ligands on the surface of other cells or viruses. These specific affinities of immunoglobulin-like molecules may be essential for the recognition functions of T4 and T8.

Evolution of T4

In the immunoglobulin and T cell antigen receptor genes, the V and J exons are widely separated and become juxtaposed only after a somatic recombination event (62, 63). The T4 mRNA encodes four contiguous Vand J-like elements without the requirement for DNA recombination events. It is therefore possible that T4 reflects a more primitive gene that evolved before the emergence of rearrangement mechanisms. Further support for this derives from recent observations that the first V-like region of T4 (V1) is split by an intron not present in the V genes encoding either the immunoglobulins or T cell antigen receptors. Accumulating evidence suggests that it is far more likely for introns to be precisely removed during evolution that for introns to be inserted in a previously intron-free environment. Thus, T4 may represent an ancestral immunoglobulin gene which underwent duplications, divergence, and rearrangement to generate the current immunoglobulin gene family. Although functional in a far more complex immune system at present, T4 may reflect receptors operative in more primitive cellular immune responses. Primitive immune responses, such as those of invertebrates, do not appear to involve a diverse repertoire of receptor molecules, but in the simplest cases are restricted to a distinction between self and nonself (85, 86) and are likely to be accommodated by a "static" set of genes that do not undergo rearrangement.

Whatever the order of appearance of T4 in evolutionary time, the organization of this genes reveals an interesting example of exon shuffling. T4 consists of four V-J-like domains, a J-like region and a transmembrane segment, each sharing homology with different members of the immunoglobulin supergene family. The V- and J-like domains are homologous to the equivalent regions of both immunoglobulins and the T cell antigen receptor chains; the transmembrane domain shows considerable homology to this region in the β-chains of class II MHC molecules (FIG. 9C). T4, therefore, consists of a collection of exons conserved in several members of the immunoglobulin supergene family which are shuffled in different ways to generate a large number of different molecules which participate in the immune response.

T4 is the AIDS Virus Receptor

The data provided herein suggest a mechanism of AIDS virus infection which initially involves the specific association of the AIDS virus with T4 molecules on the cell surface. This association may be demonstrated on T lymphocytes, B lymphocytes, and epithelial cells, and therefore does not require the participation of additional T cell-specific proteins. Additionally, the data provided herein indicates that the T4-AIDS virus complex is internalized via receptor-mediated endocytosis and the viral envelope then fuses with the limiting membrane of the endosome, releasing the nucleocapsid into the cytoplasm. Viral replication and transcription can then occur in both lymphoid and non-lymphoid cell lines. Moreover, the T4 gene is expressed in the brain as well as in lymphocytes, providing an explanation for the dual neurotropic and lymphotropic character of the AIDS virus. In this manner, a T lymphocyte surface protein important in mediating effector cell-target cell interations has been exploited by a human retrovirus to specifically target the AIDS virus to populations of $T4^+$ cells.

Cell surface receptors have been identified for a number of enveloped viruses and the pattern of expression of these receptors is often responsible for the host range and tropic properties of specific viruses (74, 76). Some viruses will infect only a narrow range of cell types, reflecting the expression of the viral receptor on specific populations of target cells. Rabies virus, for example, interacts with the nicotinic acetylcholine receptor (87) and infects largely skeletal muscle and neurons, whereas the Epstein-Barr virus interacts with the C3d complement receptor type 2 (88) and infects B lymphocytes. Other viruses, such as the myxoviruses, interact with ubiquitously distributed sialic acid residues on the cell surface and infect a much broader range of cell types.

The restricted expression of cell surface receptors provides only one explanation for viral tropism. Some viruses will replicate only in a restricted set of differentiated cell types whereas others will only be efficiently transcribed in specific cell types. Hence, the Moloney murine leukemia virus (Mo-MuLV) induces T cell lymphomas in newborn mice, yet the closely-related Friend helper murine leukemia virus (Fr-MuLV) induces primarily erythroleukemias (89, 90, 91). This tropism is thought to result from differences in the LTRs which facilitate the efficient transcription of the Mo-MULV genome in T lymphocytes and the Fr-MuLV genome in erythroid precursors (92, 93, 94).

As indicated herein, the primary tropic determinant of the AIDS virus is the expression of the T4 protein on the surface of the target cell. In vivo infection is restricted to lymphoid cells and myeloid cells as well as brain cells: three populations which express T4. In vitro demonstrations indicate that the introduction of T4 into $T4^-$ human B lymphocytes and epithelial cells, cells which are not natural targets for AIDS virus, renders these cells susceptible to productive infection by AIDS virus.

EXAMPLE 1

Soluble T4 Fragments

Soluble T4 glycoprotein fragments are prepared using limited protease digestion from cell preparations. Alternatively, DNA expression vectors encoding T4 fragments which lack the transmembrane domain, a region containing neutral and hydrophobic residues, may be constructed and used to produce such T4 fragments. These fragments are soluble in aqueous solutions and contain leader (signal) sequences. When expressed in mammalian cells, these fragments are transported to the rough endoplasmic reticulum/golgi complex and eventually secreted from the cells.

EXAMPLE 2

Treatment of AIDS Patients

Soluble T4 glycoprotein fragments as described in Example 1, tyically in a pharmaceutically acceptable carrier, are administered to patients infected with a human immunodeficiency virus so as to bind to virus present in the the subject's blood and other body fluids and block infection of $T4^+$ cells in vivo. Alternatively or additionally, a patient's blood is cycled through a column containing either immobilized T4 glycoproteins or soluble T4 fragments so that the virus may be separated from the blood. Such measures permit the immune system to mount a more effective immunologic response against the virus, i.e., allow uninfected $T4^+$ T cells to proliferate.

Soluble T4 fragments are used as a therapeutic, i.e., an inhibitor of extracellular and cell-cell spread of HIV infection. Applicants have shown that soluble T4 fragments inhibit in vitro HIV binding to, and infection of, $T4^+$ target cells (see Example 4). Administration of soluble T4 fragments to persons infected with HIV inhibits extracellular spread of the virus infection. Additionally, fusion of HIV-infected $T4^+$ cells and noninfected $T4^+$ cells, which is also a route by which the virus spreads, are inhibited by administration of soluble T4 fragments.

Therefore, administration of soluble T4 fragments slows the course of disease, alleviates several symptoms associated with AIDS, and prevents occurrence of new pathologic changes.

Soluble T4 fragments, biochemically pure, aqueous soluble reagents, are used in combination with other reagents to assay for competitors of the T4-HIV interaction. Thus, soluble T4 fragments, in combination with HIV envelope proteins or biochemical mixtures containing HIV envelope proteins, are used to screen for inhibitors of viral binding.

EXAMPLE 3

Production of Soluble T4 Fragments

A cDNA encoding the membrane-bound T4 protein (pT4B) has been isolated, characterized, and expressed in a variety of mammalian cell types (70). Soluble T4 fragments are produced in bacterial, yeast, insect, and mammalian systems. Because the T4 protein likely folds in a complex manner and is glycosylated, expression in mammalian systems is preferred. Soluble T4 fragments are produced by truncating pT4B after the $V_4J_4$ domain. Such DNA fragments terminate before the transmembrane segment, which begins at approximately nucleotide position 1264 (FIG. 6). This recombinant DNA molecule lacks both the transmembrane and the cytoplasmic domains. The EcoRI-HpaII fragment, which encompasses nucleotides 1 through 1252, is isolated by assemblying it from smaller fragments of pT4B. Alternatively, the membrane-spanning segment alone is deleted, leaving the $V_4J_4$ domain fused to the cytoplasmic domain. One approach is to delete the fragment spanning the HpaII sites from nucleotides 1252–1342 from pT4B. Such constructs maintain the T4 signal sequence necessary for entry into the rough endoplasmic reticulum/golgi complex and eventual secretion from the cell. In addition, these constructs maintain the extracellular portion of the T4 protein in which the binding domain for the human immunodeficiency virus envelope glycoprotein exists.

In order to express soluble T4 fragments in mammalian systems, the modified T4 cDNA fragment is subcloned into vectors containing strong eukaryotic promoters/enchancers as well as polyadenylation sites required for cleavage and polyadenylation of the RNA. For example, the simian virus (SV40) early promoter and enchancer is positioned upstream from the soluble T4 cDNA fragment. Transcription termination and RNA polyadenylation are achieved by placing the polyadenylation site of either SV40 or the human growth hormone gene downstream from the soluble T4 cDNA fragment. Introduction of a construct containing these elements together with a selectable marker into eukaryotic cells by any of several methods known in the art leads to the stable integration of exogenous DNA. Transformants selected by virtue of their ability to grow in selective media secrete soluble T4 fragments into the culture supernatant. Soluble T4 fragments are detected in the supernatant by one of several assays, e.g. radioimmunoprecipitation, and then purified.

Purification and characterization of soluble T4 fragments is greatly enhanced by constructing a cell line which overexpresses the secreted protein fragment. Strategies which allow the overexpression of proteins have been employed in bacteria, yeast, insect, and mammalian systems. Inducible expression systems have also been employed in bacteria and yeast to overproduce proteins which may be toxic if constitutively expressed. Overexpression of soluble T4 fragments is accomplished by amplifying a soluble T4 expression vector, resulting in constitutive overexpression. The amplification of dihydrofolate reductase (dhfr) genes by growth in progressively increased concentrations of the drug methotrexate, an antagonist of dhfr, has been widely employed. Since the amplified unit is not limited to dhfr coding sequences, this approach results in the coamplification of sequences adjacent to them. Therefore, dhfr is used as a selectable marker and as a means of coamplifying newly introduced sequences. This strategy has been successfully employed to increase the expression of several different genes cotransformed with dhfr plasmids. An alternative amplification scheme involves cotransfection of the soluble T4 cDNA expression vector with the plasmid pdLAT-3 followed by a selection scheme as previously described (102).

Therefore, the soluble T4 cDNA expression construct is cotransfected with a dhfr expression plasmid. Alternatively, the dhfr gene resides on the same plasmid as the soluble T4 cDNA fragment, allowing linked cotransformation. Transfection of these Constructs into dhfrdeficient (dhfr$^-$) Chinese hamster ovary (CHO) cells and subsequent selection in methotrexate permits the isolation of stable transformants that express newly introduced sequences. Several clones are purified and culture supernatants collected and assayed for the presence of soluble T4 fragments. Clones which produce the greatest levels of soluble T4 fragments are further characterized by Northern and Southern blot analyses. These cell lines are then cultivated in selective media containing stepwise increased concentrations of methotrexate. This selective pressure results in the amplification of the newly introduced dhfr gene and adjacent T4 sequences. After reaching the highest methotrexate concentration, surviving cells are subjected to Northern and Southern blot analyses to determine the extent of amplification and culture supernatants are examined for the presence of soluble T4 fragments.

In order to characterize the soluble T4 fragments in the culture supernatant, several transformants are metabolically labeled with ($^{35}$S)-methionine. Cell lysates and supernatants are then analyzed by radioimmunoprecipitation and Western blot analysis using commercially available anti-T4 antibodies. SDS-polyacrylamide gel electrophoresis is performed on the precipitates and a band of the predicted relative molecular mass ($M_r$) of the secreted, truncated form of T4 is observed. Because it is synthesized in a mammalian system, this protein is properly glycosylated and folded, i.e. disulphide bridges are formed. In order to purify the soluble T4 fragments from culture supernatant, immunoaffinity column chromatography is performed using anti-T4 antibodies. Protein bound to the column is eluted at high salt concentrations and low pH. SDS-polyacrylamide gel electrophoresis of the eluted material is performed in order to determine the $M_r$ and purity of the eluted protein fraction. In addition, radioimmunoprecipitation and Western blot analysis is also performed in order to further characterize the affinity-purified material.

Similar approaches may be undertaken in bacteria, yeast and insects to produce soluble T4 fragments. In addition, fragments smaller in size than the one described herein, e.g. containing only the $V_1J_1$ domain may be produced.

Construction of Vectors

Using recombinant DNA manipulations, base pairs (bp) 1-1257 of the human T4 cDNA sequence were placed between an SV-40 early promoter and a TAA termination codon followed by the polyadenylation region of the bovine growth hormone gene. This sequence of the T4 cDNA encodes the leader and predicted extracellular domain of the T4 receptor. This sT4 minigene was joined with a human H-ras, or a mouse dihydrofolate reductase minigene, to create the vectors pST4CHras and pST4DHFR respectively. The construction of these vectors was as follows:

Construction of PST4sal: Plasmid pST4sal was constructed from two other plasmids, JRT4 and pUCsT4. The construction of these plasmids is detailed below.

Construction of plasmid JRT4: To create plasmid JRT4, plasmid DSP1 (103) was cut with XhoI, the SV40 polyA early region was deleted and the Xho I sites were filled in using Klenow fragment of DNA polymerase. The bovine growth hormone polyadenylation region (113) was cut with PvuII and KpnI, and the KpnI site was blunted by treatment with T4 DNA polymerase. This 230 bp fragment was ligated to DSP1 to create DSP1BGH. DSP1BGH was cut with SmaI and SalI and the galK cassette (consisting of the SV40 early promoter, galK coding region and BGH polyA region) was ligated into pUC19 (107) at the SalI site by using a synthetic linker consisting of a SalI end, a BglII site, and a SmaI end. This three part ligation resulted in plasmid DSP1BZBGH.JT.

DSP1BZBGH.JT, which was cut with StuI and BclI to delete the galK coding region, was ligated to a 1.7 kb EcoRl (filled in)-BamHI fragment, containing the T4 cDNA from plasmid pT4B (70) to create plasmid JRT4.

Construction of plasmid pUCsT4: To create plasmid pUCsT4, a HaeII and HpaII fragment: (1125 bp) of the T4 cDNA from plasmid pT4B was ligated through the use of synthetic linkers to vector pUC18 which had been cut with KpnI and XbaI. The HaeII end of the T4 cDNA was ligated to the KpnI site of pUC18 using a synthetic linker with a Kpn I end and a HaeII end. The HpaII end of the T4 cDNA was ligated to the XbaI site of pUC18 using a synthetic linker with a HpaII end and an XbaI end. This linker also inserted a TAA stop codon after nucleotide 1257 of the T4 coding region. The resulting plasmid was pUCsT4.

To create plasmid pST4sal, plasmied JRT4 was cut with BglII and SacI and 959 bp fragment (consisting of the SV40 early promoter and the first 602 nucleotides of the T4 cDNA) was isolated. Plasmid pUCsT4 was cut with SacI and XbaI and a 660 bp fragment (consisting of the T4 cDNA from nucleotides 603–1257 followed by the TAA codon from the synthetic linker) was isolated. These two fragments were ligated into DSP1BZBGH.JT which had been cut with BglII and XbaI to delete the SV40 early promoter and full length T4 coding region. The resulting plasmid was pST4sal.

Construction of PST4DHFR: To create plasmid PST4DHFR, a BglII-BamHI fragment containing a β-globin DHFR expression cassette was ligated into the BamHI site of pST4sal. The β-globin DHFR expression cassette consists of: the mouse β-globin promoter (550 bp HincII fragment from plasmid pPK288 (108) modified at its 5' end with a synthetic linker to contain a BglII site; the mouse DHFR coding region (735 bp HindIII (fill-in) fragment from plasmid pSV2-DHFR (109); NheI (fill-in)-BamHI (fill-in) SV40 polyA early region from DSP1 (103); and the mouse DHFR terminator region (907 bp HindIII (fill-in fragment from plasmid mDH9 (110), modified at its 3' end with a synthetic linker to create a BamHI site. The plasmid map of pST4DHFR is shown.

Construction of pST4 cHras: Plasmid pMERcHras was created by cutting plasmid pSVK (111) with EcoRV and HindIII (fill-in), to remove the galK region, and ligating in an 870 bp NdeI (fill-in)-SalI (blunted by mung bean nuclease) fragment, containing the coding region for cHras, from plasmid pSKcHras (112).

The soluble T4 transcription cassette was removed from pST4sal via a BglII-BamHI fragment and ligated into the BamHI site (3' to the SV40 polyA early) of pMERcHras to create pST4 cHras.

Expression of Soluble T4 (sT4) Minigenes in Mammalian Cells

Expression of psT4cHras in NIH-3T3 cells: Plasmid pST4cHras (10 μg) was co-precipitated by the calcium phosphate precipitation method with 10 μg of plasmid pTKneo, a vector conferring G418 resistance, in the presence of 10 μg carrier DNA (NIH-3T3 genomic DNA) onto NIH-3T3 cells (seeded at $5 \times 10^5$ cells per 60 mm culture dish on the preceding day). The cells were incubated with the precipitated DNA for 6 hours at 37° C. The DNA precipitate was removed and fresh media (DMEM, 5% Nu-Serum˙ (Collaborative Research, Inc., Lexington, Mass.)) was added to the dishes. The cells were trypsinized 16 hours later and seeded into three 100 mm dishes and maintained in the above media. Foci (approximately 50 per dish) appeared in 12–14 days. Eleven of the transformed foci were selected, expanded and then seeded at $5 \times 10^5$ cells per 100 mm dish for selection in the above media plus 500 μg/ml GENETI-CIN˙ G418 (Gibco Laboratories, Grand Island, N.Y.). All 11 clones survived G418 selection (500 μg/ml) and were screened for H-ras (p21) levels by standard protein immunoblot analysis.

The clones which expressed the highest levels of p21 (approximately 2 ng p21/μg Triton-soluble protein) were assayed for expression of sT4. Confluent cultures were incubated for 18 hours with $^{35}$S-labelled methionine and cysteine. Culture supernatants and cell lysates were immunoprecipitated with monoclonal antibodies specific for the T4 (OKT4, OKT4A) and the T8 (OKT8) receptors, polyclonal antibody specific for ras proteins, or nonspecific mouse IgG. A protein of about 45 kd, the predicted size of sT4, was specifically precipitated from the culture medium by both of the monoclonal antibodies directed against the T4 receptor. The sT4 band was not observed in cell lysates. As expected, p21 was precipitated from the cell but not from the culture supernatants. Subsequent quantitation shows, compared to purified sT4, these cells produce relatively low levels of sT4, i.e., approximately 100 fold lower than with CHO cells as described in Example 2B.

Expression of pST4DHFR in Chinese Hamster Ovary (CHO) cells: DXB-11 cells, a DHFR deficient CHO cell line (104) were transfected by calcium phosphate preciptiation with 10 to 30 μg of pST4DHFR in the presence of 10 μg carrier DNA (NIH-3T3 genomic DNA), one day after seeding 60 mm dishes with $5 \times 10^5$ cells. Cells were incubated with the DNA precipitate for 6 hours at 37° C., the media was removed, and fresh media (F12, 10% FBS, 100 units/ml penicillin and streptomycin) was added to the dishes. The media was changed again after 16 hours and the cells were incubated for another 24 hours. The cells were then trypsinized, seeded into three 100 mm dishes and selected in nucleoside-free media (F-12 without hypoxanthine and thymidine, 10% dialyzed FBS, and 100 units/ml penicillin and streptomycin). Colonies (approximately 100 per dish). appeared in 7–10 days. Colonies from each dish were pooled, expanded and then seeded at $5 \times 10^3$ and at $5 \times 10^4$ cells per well in 24 well culture plates, or at $5 \times 10^5$ cells per 100 mm dish. The cells were allowed to recover for 3 days before beginning selection in nucleoside free media containing 20 nM methotrexate (mtx). Individual wells or clones were assayed at confluence for sT4 expression, and those selected for further amplification were seeded into 24 well culture plates at the densities described above. Selection at 800 nM mtx in nucleoside-free media was started 3 days after seeding. This selection procedure was repeated for selections at 8 μMmtx and 80 μM mtx. Several cell lines were derived using this method which express soluble T4 at a minimum of 3 μg/cell/24 hrs.

Purification of sT4: Conditioned medium (CM) was prepared serum-free from adherent cell cultures expanded into 850 cm² roller bottles under mtx selective conditions. At confluence, the cells were washed twice with phosphate buffered saline (PBS) without $Mg^{2+}$ and $Ca^{2+}$ and the growth medium (Ham's F12 without hypoxanthine and thymidine, 10% fetal bovine serum, 100 units/ml penicillin and streptomycin and mtx at the selective concentration) was replaced with the same medium minus serum and mtx and plus 1×ITS (insulin, transferrin and selenium (Collaborative Research Inc.). After 24–48 hrs., the medium was removed and replaced with selective growth medium. Serum-free medium was then reapplied within 3–5 days and this cycle repeated indefinitely, i.e., for more than two months. CM was clarified by centrifugation at 8,000×g. A protease inhibitor PMSF (phenylmethylsulfonylfluoride) was added to 0.5 mM and the CM was concentrated about 10-fold by pressure membrane filtration. This concentrated CM was clarified by centrifugation at 2000×g and Aprotinin, protease inhibitor (Sigma Chemical, St. Louis, Mo.) was added to a final concentration of 5 µg/ml. The sample was processed directly or after storage at −70° C.

The concentrated CM sample was diluted 2-fold with 50 mM MES [2-(N-morpholino)-ethanesulfonic acid], pH 6.0 and filtered through a 0.45 micron filter. The sample was then treated with 100 µm pAPMSF (p-amidinophenylmethylsulfonylfluoride) (CalBiochem-Behring, San Diego, Calif.) and applied to a S-Sepharose® (Sulpho-propyl) (Pharmacia P-L Biochemicals, Piscataway, N.J.) column equilibrated in 50 mM MES, pH 6.0 at a protein concentration of 1.5–2.0 mg/ml gel. The sample was eluted using a linear gradient: of 0–0.5 M NaCl in 50 mM MES, pH 6.0. Peak fractions which eluted at approximately 0.2 M NaCl were pooled and treated with pAPMSF to 100 µM. Fractions containing sT4 were confirmed by SDS-PAGE and immunoblot assays. After sitting at 4° C. for 1 hour the sample was dialyzed against 50 mM Bis-Tris propane [1,3-bis[tris-(hydroxymethyl)-methyl amino] propane], pH 6.0.

The sample was treated with 100 µM pAPMSF and 0.1% thiodiglycol, pH 9.0 was then applied to a Q-Sepharose® (quarternary amino ethyl) column (Pharmacia) (5 ml sample/ml gel) equilibrated in 50 mM Bis-Tris propane (BTP), pH 9.0. The sT4 sample does not bind to the Q-Sepharose® and was recovered in the unbound fraction and column wash. The unbound sample was immediately adjusted to pH 6.0.

The final step was chromatography on a 30 micron Superose® 12 column (2.5×46 cm) (Pharmacia) equilibrated in 50 mM phosphate, 0.15 M NaCl pH 7.0. The column was run at a flow rate of 3.0 ml/min. Ten ml injections were made and the 42 minute peak was collected batchwise. The process yielded approximately 1.0 mg of product per 20.0 mg of total protein for a cell line producing approximately 3 µg/cell/day.

Characterization of the sT4

Physical Properties: Total protein concentration was determined using the colormetric BCA protein assay (Bicinchoninic Acid, Pierce Chemical Co., Rockford, Ill.). Absolute concentrations were determined by quantitative amino acid analysis. The measured amino acid composition of the purified sT4 was performed using standard amino acid analysis techniques and was found to agree with the predicted sequence for the molecule to within experimental error (+/− 15%). Through the first 20 residues the sequence was as predicted except that it begins lys-lys-val-val- - - -. Thus, the mature amino terminus begins at position +3 with respect to the predicted leader clip site and differs from the predicted sequence at that position by an asn to lys change. The position of the mature amino terminus agrees well with the determined termini of the mouse and sheep CD4 proteins. The asn to lys change may represent a sequencing error (single base change) or a mutation which arose during recombinant procedures.

Immuno-epitopes: The monoclonal antibodies OKT4 and OKT4A recognize non-interfering surface epitopes of the T4 receptor (114). These antibodies are specific for the native conformation in that they will not bind to reduced, SDS denatured protein in immuno-blot assays. It was shown that both antibodies specifically precipitate sT4 from $^{35}$S-labeled culture supernatants using the following immunoprecipitation procedure:

Cultures of sT4-producing cells containing 1×10⁶ cells per 60 mm culture dish were labeled for 16 hours at 37° C. in 1.5 ml methionine and cysteine free F12 medium containing ITS, and 170 µCL/ml [$^{35}$S]methionine and 30 µCi/ml [$^{35}$S]cysteine (ICN Biomedicals, Inc., Costa Mesa, Calif.). Clarified medium (100 µl) was diluted with an equal volume of precipitation buffer (10 mM sodium phosphate pH 7.5, 100 mM NaCl, 0.1% NP-40®, 0.5% non-fat dry milk) and incubated with 3 µg rabbit IgG for 15 min. at 4° C. followed by 30 µg (packed volume) of protein A sepharose beads (Pharmacia P-L Biochemicals) for 30 min. at 4° C. The precleared supernatant was incubated with 5 µg of OKT4, OKT4A and OKT8 (gift of P. Rao, Ortho Pharmaceuticals Corp., Raritan, N.J.), mouse IgG (Cooper Biomedical, Malvern, Pa.), or rabbit α-mouse IgG (Cooper Biomedical) for 30 min at 4° C. OKT4, OKT4A, OKT8, mouse IgG, and rabbit α-mouse IgG were precipitated by incubation with 20 µl (packed volume) of protein A sepharose beads for 30 min. at 4° C. Following precipitation, the beads were washed twice with 200 µl precipitation buffer and once with 200 µl precipitation buffer minus NP-40® and non-fat dry milk. The washed beads were boiled for 5 min. in 20 µl sample buffer (125 mM Tris-HCl pH 6.8, 20% glycerol, 1.4 M β-mercaptoethanol), and the supernatants were analyzed by electrophoresis on a 12.5% SDS-polyacrylamide gel. Similar results were obtained with OKT4B, OKT4C, OKT4D, OKT4E, OKT4F and other Mabs specific for T4. These results suggest that the conformation of sT4 accurately mimics the surface domain of the T4 receptor.

To determine whether sT4 can associate with HIV gp120 and whether this association can inhibit the binding of HIV to T4 cells, approximately 5 micrograms of purified sT4 were absorbed to Sepharose beads coated with OKT4 or control antibody. The beads were then mixed with a lysate of $^{35}$S-methionine labeled HIV. The complex of sT4 with OKT4 coprecipitates only the 120 kd envelope glycoprotein. No viral proteins are precipitated by OKT4 beads in the absence of sT4 or in the presence of control supernatants from the untransfected CHO cells. Furthermore, viral protein is not precipitated if Sepharose beads coated with control mouse immunoglobulin (isotype matched to OKT4) are incubated with sT4. These studies indicate that the sT4 obtained, which is free of other cell surface components present on the surface of T lymphocytes, is capable of specifically associating with the envelope glycoprotein of the AIDS virus.

Cytofluorometry was performed to demonstrate that the interaction of T4 with gp120 of intact HIV abolishes the binding of AIDS virus to the surface of T4⁺ cells. T4⁺ CEM cells were exposed to HIV in the presence or absence of sT4. Following viral absorption, the cells were washed, exposed to fluorescein conjugated anti-HIV antibody, and analyzed by flow cytometry (FIG. 17) (48). In the absence of sT4, HIV binds efficiently to T4⁺ CEM cells. If HIV is preincubated with sT4, the binding of virus to T4⁺ cells is abolished (FIG. 17). Ten nanograms of purified sT4 is sufficient to inhibit the binding of 100 nanograms of viral protein. If the envelope glycoprotein comprises 5% of the total viral protein, an estimated a 5:1 molar ratio of T4 to gp120 is capable of complete inhibition of HIV binding to T4⁺ cells.

The ability of sT4 to inhibit the infection of T4⁺ cells by HIV was also studied. Phytohemagglutinin-stimulated human lymphocytes were exposed to serial ten-fold dilutions of an HIV inoculum in the presence or absence of sT4, washed, and plated in microculture. The frequency of infected cultures was determined usinc an immunoassay 4.8 and 12 days after exposure to virus (47). In this manner the infectious virus titer, ID-50 is defined as the reciprocal of the dilution required to infect 50% of the exposed cell cultures at day 12. In the absence of sT4, the ID-50 observed with the viral inoculum is approximately $10^5$. However, in the presence of 8 micrograms/ml of purified soluble T4, the infectively is diminished by almost 4 logs to an ID-50 of $10^{1.5}$ (FIG. 18). This dramatic reduction in infectivity by HIV is observed throughout the entire course of infection. As a control for nonspecific inhibition or toxic effects of sT4, sT4 was added to cultures 18 hours after the initial exposure to virus. Cultures exposed to sT4 18 hours after infection show only a 1 log inhibition in the ID-50 which presumably results from inhibition of virus spread following the initial inoculation. Thus, the 4 log reduction in virus infectivity observed when virus is preincubated with sT4 is likely to result from the specific association of sT4 with gp120 on the surface of virus. These particles are therefore no longer capable of interacting with the T4 receptor on the cell surface. Four logs of inhibition were observed when $10^5$ infectious particles/ml are preincubated with 8 micrograms/ml of sT4. The viral preparations of $10^5$ infectious particles/ml were estimated to contain $10^9$ particles/ml. If each particle contains 1,000 envelope glycoproteins, then the inhibition is obtained at a ratio of 100 T4 molecules/molecule of envelope protein.

The availability of relatively large quantities of structurally intact sT4 facilitates the study of the mechanism of interactions of T4 with the surface of both antigen-presenting cells as well as with HIV virus. The specificity of interaction of T4+ helper cells with antigen-presenting cells (B cells and macrophages) may result, at least in part, from the association of T4 with class II MHC molecules (105, 106). The availability of significant amounts of purified sT4 permits a direct demonstration of a physical association between T4 and class II MHC molecules.

The ability of sT4 to bind gp120 and inhibit viral infection in vitro indicates that sT4 is an effective anti-viral agent for treating AIDS patients.

EXAMPLE 5

Preparation of Anti-Soluble T4 Fragment Antibodies

Eight week old Balb/c mice are injected intraperitoneally with 50 micrograms of a purified soluble T4 fragment of the present invention (prepared as described above) in complete Freund's adjuvant, 1:1 by volume. Mice are then boosted, at monthly intervals, with the soluble T4 fragment mixed with incomplete Freund's adjuvant, and bled through the tail vein. Immunoglobulin cuts of sera are generated by ammonium sulfate precipitation and specific anti-soluble T4 fragment antibodies are purified by affinity chromatography using an immobilized T4 fragment.

EXAMPLE 6

Preparation of Soluble T4 Fragment Anti-Idiotypic Antibodies

Syngenic and congenic mice are injected intraperitoneally with 50 micrograms of a purified anti-soluble T4 fragment antibody, of the present invention (prepared as described above) in complete Freund's adjuvant and boosted with the anti-soluble T4 fragment antibody in incomplete Freund's adjuvant monthly. On days 4, 3, and 2 prior to fusion, mice are boosted intravenously with 50 micrograms of immunoglobulin in saline. Splenocytes are then fused with P3X63 AG8.653 non-secreting myeloma cells according to procedures which have been described and are known in the art to which this invention pertains. Two weeks later, hybridoma supernatants are screened for binding activity against anti-soluble T4 fragment antibodies by radioimmunoassay. Positive clones are then assayed for the ability to bind a human immunodeficiency virus envelope glycoprotein and AIDS virus. Alternatively, using the "one-step" procedure, mice are injected intraperitoneally with a soluble T4 fragment: in complete Freund's adjuvant, boosted intravenously with the soluble T4 fragment in saline, and mice spleen cells fused with myelomas as above. Hybridoma supernatants are then assayed directly for soluble T4 fragment anti-idiotypic antibodies.

REFERENCES

1. E. L. Reinherz et al., "Discrete Stages of Human Intrathymic Differentiation: Analysis of Normal Thymocyte and Leukemic Lymphoblasts of T Cell Lineage", Proc. Natl. Acad. Sci. USA 77: 1588–1592 (1980).
2. E. L. Reinherz and S. F. Schlossman, "The Differentiation and Functioin of Human T Lymphocytes", Cell 19: 821–827 (1980).
3. M. L. Blue et al., "Coexpression of T4 and T8 on Peripheral Blood T Cells Demonstrated by Two-color Fluoroescence Flow Cytometry", J. Immunol. 134: 2281–2286 (1985)
4. E. G. Engleman et al., "Activation of Human T Lymphocyte subsets: Helper and Suppressor/Cytotoxic T Cells Recognize and Respond to Distinct Histocompatibility Antigens", J. Immunol. 127: 2124–2129 (1981)
5. A. M. Krensky et al., "Long-term Human Cytolytic T-cell Lines Allospecific for HLA-DR6 Antigen Are OKT4+", Proc. Natl. Acad. Sci. USA 79: 2365–2369 (1982).
6. S. C. Meuer, S. F. Schlossman and E. Reinherz, "Clonal Analysis of Human Cytotoxic T Lymphocytes T4+ and T8+ Effector T Cells Recognize Products of Different Major Histocompatibility Complex Regions", Proc. Natl. Acad. Sci. USA 79: 4395–4399 (1982).
7. W. E. Biddison et al., "Possible Involvement of the OKT4 Molecule in T Cell Recognition of Class II HLA Antigens", J. Exp. Med. 156: 1065–1076 (1982).
8. D. R. Wilde et al., "Evidence Implicating L3T4 in Class II MHC Antigen Reactivity Monoclonal Antibody GK 15 (Anti-L3T4) Blocks Class II MHC Antigen-Specific Proliferation, Release of Lymphokines and Binding by Cloned Murine Helper T Lymphocyte Line,", J. Immunol. 131: 2178–2183 (1983).
9. S. L. Swain, "T Cell Subsets and the Recognition of MHC Class", Immunol. Rev. 74: 129–142 (1983).
10. Y. Thomas et al., "Functional Analysis of Human T Cell Subsets Defined by Monoclonal Antibodies. IV. Induction of Suppressor Cells Within the OKT4+ Population", J. Exp. Med. 154: 459–467 (1981).
11. E. G. Engleman et al., "Antibodies to Membrane Structures that Distinguish Suppressor/Cytotoxic and Helper T Lymphocyte Subpopulations Block the Mixed Leukocyte Reaction in Man", J. Exp. Med. 154: 193–198 (1981).
12. P. Marrack et al., "The Major Histocompatibility Complex-restricted Antigen Receptor on T Cells. II. Role of the L3T4 Product", J. Exp. Med. 158: 1077–1091 (1983).
13. L. Rogozinski et al., "The T4 Surface Antigen is Involved in the Induction of Helper Function", J. Immunol. 132: 735–739 (1984).
14. S. L. Swain, "Significance of Lyt Phenotypes: Lyt2 Antibodies Block Activities of T Cells that Recognize Class I Major Histocompatibility Complex Antigens Regardless of Their Function", Proc. Natl. Acad. Sci. USA 78: 7101–7105 (1981).

15. U. Landegren et al., "Selective Inhibition of Human T Cell Cytotoxicity at Levels of Target Recognition of Initiation of Lysis by Monoclonal OKT3 and Leu-2a Antibodies", J. Exp. Med. 155: 1579–1584 (1982).
16. R. M. Zinkernagel and P. C. Doherty, "MHC-restricted Cytotoxic T Cells: Studies on the Biological Role of Polymorphic Major Transplantation Antigens Determining T Cell Restriction, Specificity, Function, and Responsiveness", Adv. Immunol. 27: 52–177 (1979).
17. J. Kappler et al., "The Major Histocompatibility Complex-Restricted Antigen Receptor on T Cells in Mouse and Mar: Identification of Constant and Variable Peptides", Cell 35: 295–302 (1983).
18. O. Acuto et al., "The Human T Cell Receptor: Appearance in Ontogeny and Biochemical Relationship of Alpha and Beta Subunits on IL-2 Dependent Clones and T Cell Tumors", Cell 34: 717–726 (1983).
19. P. Kavathas et al., "Isolation of the Gene Coding for the Human T Lymphocyte Antigen Leu-2 (T8) by Gene Transfer and cDNA Subtraction", Proc. Natl. Acad. Sci. USA 81: 7688–7692 (1984).
20. D. R. Littman et al., "The Isolation and Sequence of the Gene Encoding T8: A Molecule Defining Functional Classes of T Lymphocytes", Cell 40: 237–246 (1985).
21. V. P. Sukhatma et al., "The T Cell Differentiation Antigen Leu-2/T8 is Homologous to Immunoglobulin and T Cell Receptor Variable Regions", Cell 40: 591–597 (1985).
22. S. M. Friedman et al., "OT-CLL: A Human T Cell Chronic Lymphocytic Leukemia That Produces IL-2 in High Titer", J. Immunol. 128: 935–940 (1982).
23. D. A. Thurley-Lawon, L. Chess and J. L. Strominger, "Suppression of In Vitro Epstein-Barr Infection: A New Role for Adult Human T Cells", J. Exp. Med. 146: 495–508 (1977).
24. J. W. Goding, "The Chromic Chloride Method of Coupling Antigens to Erythrocytes: Definition of Some Important Parameters", J. Immunol. Methods 10: 61–66 (1976).
25. F. L. Graham and A. J. van der Eb, "A New Technique for the Assay of Infectivity of Human Adenovirus DNA", Virology 52: 456–467 (1973).
26. M. Wigler et al., "Biochemical Transfer of Single-Copy Eucaryotic Genes Using Total Cellular DNA as Donor", Cell 14: 725–731 (1978).
27. M. Wigler et al., "Transfer of Purified Herpes Virus Thymidine Kinase Gene to Cul-tured Mouse Cells", Cell 11: 22:3–232 (1977).
28. J. M. Chirgwin et al., "Isolation of Biologically Active Ribonucleic Acid from Sources Enriched in Ribonuclease", Biochemistry 18: 5294–5299 (1979).
29. H. Aviv and P. Leder, "Purification of Biologically Active Globin Messenger RNA by Chromatography on Oligothymidylic Acid-Cellulose", Proc. Natl. Acad. Sci. USA 69: 1408–1412 (1972).
30. T. Huynh, R. A. Young and R. W. Davis, "Construction and Screening cDNA Libraries in gt10 and gt11", *DNA Cloning Techniques—A Practical Approach*, D. M. Glover, ed. (Oxford: IRL Press), in press.
31. T. Maniatis et al., "The Isolation of Structural Genes from Libraries of Eucaryotic DNA", Cell 15: 687–701 (1978).
32. M. M. Davis et al., "Cell-Type-Specific cDNA Probes and the Murine I Region: the Localization and Orientation of $A^d$ Alpha", Proc. Natl. Acad. Sci. USA 81: 2194–2198 (1984).
33. T. Maniatis, E. F. Fritch and J. Sambrook, *Molecular Cloning* (Cold Spring Harbor, N.Y.; Cold Spring Harbor Laboratory) (1982).
34. P. W. J. Rigby et al., "Labeling Deoxyribonucleic Acid to High Specific Activity In Vitro by Nick Translation with DNA Polymerase I", J. Mol. Biol. 113: 237–251 (1977).
35. J. Vieira and J. Messing, "The pUC Plasmids, an M13mp7-Derived System for Insertion Mutagenesis and Sequencing with Synthetic Universal Primers", Gene 19: 259–268 (1982).
36. F. Sanger, S. Nicklen and A. Coulson, "DNA Sequencing with Chain-Terminating Inhibitors", Proc. Natl. Acad. Sci. USA 74: 5463–5467 (1977).
37. E. Southern, "Detection of Specific Sequences Among DNA Fragments Separated by Gel Electrophoroesis", J. Mol. Biol. 98: 503–517 (1975).
38. G. M. Church and W. Gilbert, "Genomic Sequencing", Proc. Natl. Acad. Sci. USA 81: 1991–1995 (1984).
39. R. H. Scheller et al., "A Family of Genes that Codes for ELH, a Neuropeptide Eliciting a Stereotyped Pattern of Behavior in Aplysia", Cell 28: 707–719 (1982).
40. K. Zinn, D. DiMaio and T. Maniatis, "Identification of Two Distinct Regulatory Regions Adjacent to the Human Beta-Interferon Gene", Cell 34: 865–879 (1983).
41. C. Terhorst et al., "Further Structural Studies of the Heavy Chain of HLA Antigens and Its Similarity to Immunoglobulins", Proc. Natl. Acad. Sci. USA 74: 4002–4006 (1977).
42. J. A. Hedo, L. C. Harrison and J. Roth, "Binding of Insulin Receptors to Lectins: Evidence for Common Carbohydrate Determinants on Several Membrane Receptors", Biochemistry 20: 3385–3393 (1981).
43. U. K. Laemmli, "Cleavage of Structural Proteins During the Assembly of the Head of Bacteriophage T4", Nature 227: 680–685 (1970).
44. R. Mann, R. C. Mulligan, and D. Baltimore, Construction of a retrovirus packaging mutant and its use to produce helper-free defective retrovirus, Cell 33, 153–159 (1983).
45. F. Barre-Sinoussi, et al., Isolation of a T lymphotropic retrovirus from a patient at risk for acquired immune deficiecny syndrome (AIDS), Science 220, 868–871 (1983).
46. J. S. McDougal, et al., Cellular tropism of the human retrovirus HTLV-III/LAV. I. Role of T cell activation and expression of the T4 antigen, J. Immol. 135, 3151–3162 (1985).
47. J. S. McDougal, et al., Immunoassay for the detection and quantitation of infectious human retrovirus, lymphadenopathy-assoicated virus (LAV), J. Immunol. Meth. 76, 171–183 (1985).
48. J. S. McDougal, et al., Binding of HTLV-III/LAV to T4[+] T cells by a complex of the 110K viral protein and the T4 molecule, Science 231, 382–385 (1986).
49. C. B. Reimer, et al., Standardization of ligand binding assays for alpha-fetoprotein. In Immunofluorescence and Related Staining Techniques. W., Knapp, K. Holubar, and G. Wick, eds. (Amsterdam:Elsevier/North Holland Press) p. 189 (1978).
50. M. B. Wilson and P. K. Nakane, Recent developments in the periodate method of conjugating horseradish peroxidase (HRPO) to antibodies. In Immunofluorescence and Relating Staining Techniques, W. Knapp, K. Holubar, and G. Wick, eds. (Amsterdam:Elsevier/North Holland Press), p. 215 (1978).
51. J. Porath, R. Axen, and S. Ermback, Chemical coupling of proteins to agar, Nature 215, 1491–1493 (1967).
52. B. J. Poiesz, et al., Detection and isolation of type C retrovirus particles from fresh and cultured lymphocytes 52. of a patient with cutaneous T cell lymphoma. Proc; Natl. Acd. Aci. USA 77, 7415–7419 (1980).
53. P. Clapham, K. Nagy, and R. A. Weiss, Pseudotypes of human T-cell virus types 1 and 2: Neutralization by pateints' sera, Proc. Natl. Acad. Sci. USA 81, 2886–2889 (1984).
54. A. G. Dalgleish, et al., The CD4 (T4) antigen is an essential component of the receptor for the AIDS retrovirus, Nature 312, 763–766 (1984).
55. M. Popovic, et al., Detection, isolation, and continuous production of cytopathic retorviruses (HTLV-III) from patients with AIDS and Pre-AIDS, Science 224, 497–500 (1984).
56. K. Nagy, et al., Human T-cell leukemia virus type 1: induction of sycytia and inhibition by patients' sera, Int. J. Cancer 32, 321–328 (1983).
57. D. M. Neville and H. Glossman, Molecular weight determination of membrane protein and glycoprotein subunits by discontinuous gel electrophoresis in dodeyl sulfate, Methods Enzymol. 32, 92–102 (1974).
58. A. Helenius, et al., On the entry of Semliki Forest virus into BHK-21 cells, J. Cell. Biol. 84, 404–420 (1980).
59. R. D. Cone and R. C. Mulligan, High-efficiency gene transfer into mammalian cells: Generation of helper-free recombinant retroviruses with broad mammalian host range, Proc. Natl. Acad. Sci. USA 81, 6349–6353 (1984).
60. F. W. Alt et al., "Probes for Specific mRNAs by Subtractive Hybridization: Anomalous Expression of Immunoglobulin Genes", in *Eucaryotic Gene Regulation*, R. Axel, T. Maniatis and C. F. Fox, eds. (New York: Academic Press), pp. 407–419 (1979).
61. M. Kozak, "Comparison of Initiation of Protein Synthesis in Procaryotes, Eucaryotes and Organelles", Microbiol. Rev. 47: 1–45 (1983).
62. L. Hood, M. Kronenberg and T. Hunkapiller, "T Cell Antigen Receptors and the Immunoglobulin Supergene Family", Cell 40: 225–229 (1985).
63. S. Tonegawa, "Somatic Generation of Antibody Diversity", Nature 302: 575–581 (1983).
64. J. Kyte and R. F. Doolittle, "A Simple Method for Displaying the Hydropathic Character of a Protein", J. Mol. Biol. 157: 105–132 (1982).
65. G. von Heijne, "Patterns of Amino Acids Near Signal-Sequence Cleavage Sites", Eur. J. Biochem. 133: 17–21 (1983).
66. E. A. Kabat et al., "Sequences of Proteins of Immunological Interest" (Washington, D.C.; U.S. Department of Health and Human Ser-vices), p. 281 (1983).
67. A. F. Williams et al., "Cell Surface Glyco-proteins and the Origins of Immunity", In the Proceedings of the Sicrid Juselius Sym-posium, L. C. Andersson, C. G. Gahmberg and P. Ekblom, eds. (New York: Academic Press), in press (1984).
68. L. M. Amzel and R. J. Poljak, "Three-Dimensional Structure of Immunoglobulins", Ann. Rev. Biochem. 48: 961–997 (1979).
69. P. Y. Chou and G. D. Fasman, "Empirical Predictions of Protein Conformation", Ann. Rev. Biochem. 47: 251–276 (1978).
70. P. J. Maddon, et al., The isolation and nucleotide sequence of a cDNA encoding the T cell surface protein T4: A new member of the immunoglobulin gene family, Cell 42, 93–104 (1985).
71. R. A. Adams, A. Flowers and B. J. Davis, Direct implantation and serial transplatation of human acute lymphoblastic leukemia in hamsters, SB-2, Can. Res. 28, 1121–1125 (1968).
72. G. O. Gey, W. D. Coffman and M. T. Kubicek, Tissue culture studies of the proliferative capacity of cervical carcinoma and normal epithelium, Cancer Res. 12, 264–265 (1952).
73. R. J. V. Pulvertaft, Cytology of Burkitt's tumor (African lymphoma), Lancet I, 238–240 (1964).
74. N. J. Dimmock, Initial stages of infectior with animal viruses, J. Gen. Virol. 59, 1–22 (1982).
75. J. White, M. Kielian and A. Helenius, Membrane fusion proteins c)f enveloped animal viruses, Quart. Rev. Biophys. 16, 151–195 (1983).
76. M. Marsh, The entry of enveloped viruses into cells by endocytosis, Biochem. J. 218, 1–10 (1984).
77. M. Kielian and A. Helenius, Entry of alphaviruses. In the Togaviridae and Flaviviridae, S. Schlesinger and M. J. Schlesinger, eds., (Plenum Publishing Corp.), pp. 91–119 (1986).
78. S. Ohkuma, and B. Poole, Fluorescence probe measurements of the intralysosomal pH in living cells and the pertubation of pH by various agents, Proc. Natl. Acad. Sci. USA 75, 3327–3331 (1978).
79. F. R. Maxfield, Weak bases and ionophore rapidly and reversibly raise the pH of endocytic vesicles in cultured mouse fibroblasts, J. Cell. Biol. 95, 676–681 (1982).
80. A. Helenius, M. Marsh, and J. White, Inhibition of Semliki Forest virus penetration b lysosomotropic weak bases, J. Gen. Virol. 58, 47–61 (1982).
81. R. T. Johnson and J. C. McArthur, AIDS and the brain, TINS 9, 91–94 (1986).
82. P. M. Snow, M. Van de Rijn and C. Terhorst, "Association Between the human Thymic Differentiation Antigens T6 and T8", Eur. J. Immunol., in press (1985).
83. P. M. Snow and C. Terhorst, "The T8 Antigen is a Multimeric Complex of Two Distinct Subunits on Human Thymocytes but Consists of Homomultimeric Forms on Peripheral Blood T Lymphocytes", J. Biol. Chem. 258: 14675–14681 (1983).
84. C. Terhorst et al., "Biochemical Analysis of Human T Lymphocyte Differentiation Antigens T4 and T5", Science 209: 520–521 (1980).
85. W. H. Hildemann, "Immunocompetance and Allogeneic Polymorphism Among Invertebrates", Transplantation 27: 1–3 (1979).
86. V. L. Scofield et al., "Protochordate Allorecognition is Controlled by a MHC-like Gene System", Nature 295: 499–502 (1982).
87. T. L. Lentz, et al., Is the acetylcholine receptor a rabies virus receptor?, Science 215, 182–184 (1982).
88. J. D. Fingeroth, et al., Epstein-Barr virus receptor of human B lymphocytes is the C3d receptor CR2, Proc. Nat l. Acad, Sci. USA 81, 4510–4514 (1984).
89. P. E. Tambourin, et al., The physiopathology of Friend leukemia, Leukemia Res. 3, 117–129 (1979).
90. A. Oliff, et al., Isolation of transplantable erythroleukemia cells from mice infected with helper-independent Friend murine leukemia virus, Blood 58, 244–254 (1981).
91. J. E. Silver and J. M. Fredrickson, Susceptibility to Friend helper virus leukemias in CXB recombinant inbred mice, J. Exp. Med. 158, 1693–1702 (1983).
92. P. A. Chatis, et al., Role for the 3' end of the genome in determining disease specificity of Friend and Moloney murine leukemia viruses, Proc. Natl. Acad. Sci, USA. 80, 4408–4411 (1983).
93. P. A. Chatis, et al., A 3' end fragment encompassing the transcriptional enhancers of nondefective Friend virus confers erthyroleukemogenicity on Moloney leukemia virus, J. Virol. 52, 248–254 (1984).

94. A. Bosze, H. J. Thiesen and P. Charnay, A transcriptional enhancer with specificity for erythroid cells is located in the long terminal repeat of the Friend murine leukemia virus, EMBO J. 5, 1615–1623 (1986).
95. A. N. Barclay, et al., Immunoglobulin-relatec structures associated with vertebrate cell surfaces, in press.
96. M. O. Dayhoff, W. C. Barker and L. T. Hunt, Establishing homologies in protein sequences. In Methods in Enzymology. Enzyme Sturcture Part I, C. H. W. Hirs and S. N. Timasheff, eds. (New York: Academic Press), pp. 524–545 (1983).
97. Y. Yanagi, et al., A human T cell-specific cDNA clone encodes a protein having extensive homology to immunoglobulin chains, Nature 308, 145–149 (1984).
98. G. K. Sim, et al., Primary structure of human T-cell receptor-chain, Nature 312, 771–775 (1984).
99. H. Saito, et al., A third rearranged and expressed gene in a clone of cytotoxic T lymphocytes, Nature 312, 36–40 (1984).
100. H. Saito, et al., Complete primary structure of the E chain and gene of the mouse major histocompatibility complex, Proc. Natl. Acad. USA 80, 5520–5524 (1983).
101. M. Isobe, et al., The gene encoding the T-cell surface protein T4 is located on humar chromsome 12, Proc. Natl. Acad. Sci. USA, 83, 4399–4402 (1986).
102. J. M. Roberts and R. Axel, Gene Amplification and Gene Correction in Somatic Cells, Cell 29, 109–119 (1982).
103. D. S. Pfarr, G. Sathe and M. E. Reff, A Highly Modular Cloning Vector for the Analysis of Eucaryotic Genes and Gene Regluatory Elements, DNA, 4, 461–467 (1985).
104. G. Urlaub and L. A. Chasin, Isolation of Chinese Hamster Cell Mutants Deficient In Dihydrofolate Reductase Activity, Proc. Natl. Acad. Sci. USA, 77, 4216–4220 (1980).
105. Gay, D. et al., Nature 328: 626–629 (1987).
106. Sleckman, B. D. et al., Nature 328: 351–353 (1987).
107. Yanisch-Perron, et al., Gene 33: 103 (1985).
108. Berg, P., et al. Mol. Cell. Biol. 3: 246 (1983).
109. Subramani, et al., Mol. Cell Biol. 1: 854 (1981).
110. Frayne, et al., Mol. Cell Biol. 4: 2921 (1984).
111. Schumperli, et al., Proc. Natl. Acad. Sci. USA 79: 257 (1982).
112. Gross, et al., Mol. Cell Biol. 5: 1015 (1985).
113. Pfarr, et al., DNA 5: 115 (1986).
114. Rao, et al., Cell Immunol. 80: 310 (1983).
115. McClure, et al., Cold Spring Harbor Conference on Cell Proliferation 9: 345 (1982).
116. Urlaub, et al., Cell 33: 405 (1983).
117. Kim, et al., Cell 42: 129 (1987).
118. Wigler, et al., PNAS USA 76: 1373 (1979).
119. Copeland, et al., Cell 17: 993 (1979).
120. Sattentau, et al., Science 234: 1120 (1986).
121. Greenstein, et al., Ann. Inst. Pastuer 138: 134 (1987).
122. Gay, et al., Ann. I9nst. Pasteur 138: 127 (1987).

What is claimed is:

1. An isolated single-stranded nucleic acid which encodes an aqueous-soluble polypeptide comprising at least a portion of a human T4 glycoprotein, which portion specifically forms a complex with a human immunodeficiency virus envelope glycoprotein.

2. A nucleic acid complementary to the nucleic acid of claim 1.

3. A nucleic acid of claim 1, wherein the nucleic acid is DNA.

4. The nucleic acid of claim 1, wherein the nucleic acid is RNA.

5. The nucleic acid of claim 1, which encodes a full-length T4 glycoprotein.

6. A vector comprising the nucleic acid of claim 1.

7. A nucleic acid of claim 1 labeled with a detectable marker.

8. A nucleic acid of claim 2 labeled with a detectable marker.

9. The nucleic acid of claim 2, wherein the nucleic acid is RNA.

10. The vector of claim 6, wherein the vector is a plasmid.

11. The vector of claim 6, wherein the vector is a virus.

12. A host vector system comprising a suitable host cell and the vector of claim 6.

13. A host vector system of claim 12, wherein the suitable host cell is a bacterial cell.

14. A host vector system of claim 12, wherein the suitable host cell is a eukaryotic cell.

15. A host vector system of claim 12, wherein the suitable host cell is an insect cell.

16. A method for producing an aqueous-soluble polypeptide which comprises a portion of a T4 glycoprotein, which portion specifically forms a complex with a human immunodeficiency virus envelope glycoprotein, said method comprising the steps of growing the host vector system of claim 12 under conditions permitting production of the aqueous-soluble polypeptide and recovering the aqueous-soluble polypeptide so produced.

17. A host vector system of claim 13, wherein the bacterial cell is an *Escherichia coli* cell.

18. A host vector system of claim 14, wherein the eucaryotic cell is a mammalian cell.

19. A host vector system of claim 14, wherein the eucaryotic cell is a yeast cell.

20. A nucleic acid which comprises at least a portion of the genomic DNA represented by the restriction enzyme map shown in FIG. 10, wherein the nucleic acid is DNA and encodes an aqueous-soluble polypeptide comprising at least a portion of human T4 glycoprotein, which portion specifically forms a complex with human immunodeficiency virus envelope glycoprotein.

21. A nucleic acid which comprises nucleotides corresponding to at least a portion of the continuous nucleic acid sequence shown on FIG. 6 which is set forth in SEQ ID NO:3 and encodes an aqeous-soluble polypeptide comprising at least a portion of human T4 glycoprotein, which portion specifically forms a complex with human immnodeficiency virus envelope glycoprotein.

22. A method for detecting a single stranded nucleic acid encoding an amino acid sequence which is at least a portion of a T4 glycoprotein, which comprises contacting single-stranded nucleic acid of claim 7 under conditions permitting hybridization of complementary single-stranded nucleic acid and separating hybridized nucleic acid so formed from single-stranded nucleic acid to thereby detect a single-stranded nucleic acid which encodes an amino acid sequence which is at least a portion of a T4 glycoprotein.

23. A method according to claim 22, wherein the single-stranded nucleic acid encoding an amino acid sequence which is at least a portion of a T4 glycoprotein is a DNA derived from chromosomal DNA.

24. The method according to claim 23 wherein the chromosomal DNA is derived from a cell selected from the group consisting of lymphoid, myeloid, and brain cells.

25. A method according to claim 24, wherein the lymphoid cell is a T cell.

26. A method according to claim 24, wherein the lymphoid cell is a B cell.

27. A method according to claim 24, wherein the myeloid cell is a granulocyte.

28. A method according to claim 24, wherein the myeloid cell is a macrophage.

* * * * *

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
        (A) LENGTH: 1273 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: YES (ix) FEATURE:
        (A) NAME/KEY: CDS
        (B) LOCATION: 76..1257

(xi) SEQUENCE DESCRIPTION: SEQ ID NO:1:

```
CAAGCCCAGA GCCCTGCCAT TTCTGTGGGC TCAGGTCCCT ACTGCTCAGC CCCTTCCTCC        60

CTCGGCAAGG CCACA ATG AAC CGG GGA GTC CCT TTT AGG CAC TTG CTT CTG       111
                Met Asn Arg Gly Val Pro Phe Arg His Leu Leu Leu
                 1               5                  10

GTG CTG CAA CTG GCG CTC CTC CCA GCA GCC ACT CAG GGA AAG AAA GTG        159
Val Leu Gln Leu Ala Leu Leu Pro Ala Ala Thr Gln Gly Lys Lys Val
         15                  20                  25

GTG CTG GGC AAA AAA GGG GAT ACA GTG GAA CTG ACC TGT ACA GCT TCC        207
Val Leu Gly Lys Lys Gly Asp Thr Val Glu Leu Thr Cys Thr Ala Ser
     30                  35                  40

CAG AAG AAG AGC ATA CAA TTC CAC TGG AAA AAC TCC AAC CAG ATA AAG        255
```

```
                                                                              -continued Gln Lys Lys Ser Ile Gln Phe His Trp Lys Asn Ser Asn Gln Ile Lys
 45                  50                  55                  60

ATT CTG GGA AAT CAG GGC TCC TCC TTA ACT AAA GGT CCA TCC AAG CTG        303
Ile Leu Gly Asn Gln Gly Ser Ser Leu Thr Lys Gly Pro Ser Lys Leu
                 65                  70                  75

AAT GAT CGC GCT GAC TCA AGA AGA AGC CTT TGG GAC CAA GGA AAC TTC        351
Asn Asp Arg Ala Asp Ser Arg Arg Ser Leu Trp Asp Gln Gly Asn Phe
             80                  85                  90

CCC CTG ATC ATC AGG AAT CTT AAG ATA GAA GAC TCA GAT ACT TAC ATC        399
Pro Leu Ile Ile Arg Asn Leu Lys Ile Glu Asp Ser Asp Thr Tyr Ile
             95                 100                 105

TGT GAA GTG GAG GAC CAG AAG GAG GAG GTG CAA TTG CTA GTG TTC GGA        447
Cys Glu Val Glu Asp Gln Lys Glu Glu Val Gln Leu Leu Val Phe Gly
110                 115                 120

TTG ACT GCC AAC TCT GAC ACC CAC CTG CTT CAG GGG CAG AGC CTG ACC        495
Leu Thr Ala Asn Ser Asp Thr His Leu Leu Gln Gly Gln Ser Leu Thr
125                 130                 135                 140

CTG ACC TTG GAG AGC CCC CCT GGT AGT AGC CCC TCA GTG CAA TGT AGG        543
Leu Thr Leu Glu Ser Pro Pro Gly Ser Ser Pro Ser Val Gln Cys Arg
                145                 150                 155

AGT CCA AGG GGT AAA AAC ATA CAG GGG GGG AAG ACC CTC TCC GTG TCT        591
Ser Pro Arg Gly Lys Asn Ile Gln Gly Gly Lys Thr Leu Ser Val Ser
                160                 165                 170

CAG CTG GAG CTC CAG GAT AGT GGC ACC TGG ACA TGC ACT GTC TTG CAG        639
Gln Leu Glu Leu Gln Asp Ser Gly Thr Trp Thr Cys Thr Val Leu Gln
            175                 180                 185

AAC CAG AAG AAG GTG GAG TTC AAA ATA GAC ATC GTG GTG CTA GCT TTC        687
Asn Gln Lys Lys Val Glu Phe Lys Ile Asp Ile Val Val Leu Ala Phe
            190                 195                 200

CAG AAG GCC TCC AGC ATA GTC TAT AAG AAA GAG GGG GAA CAG GTG GAC        735
Gln Lys Ala Ser Ser Ile Val Tyr Lys Lys Glu Gly Glu Gln Val Asp
205                 210                 215                 220

TTC TCC TTC CCA CTC GCC TTT ACA GTT GAA AAG CTG ACG GGC AGT GGC        783
Phe Ser Phe Pro Leu Ala Phe Thr Val Glu Lys Leu Thr Gly Ser Gly
                225                 230                 235

GAG CTG TGG TGG CAG GCG GAG AGG GCT TCC TCC TCC AAG TCT TGG ATC        831
Glu Leu Trp Trp Gln Ala Glu Arg Ala Ser Ser Ser Lys Ser Trp Ile
            240                 245                 250

ACC TTT GAC CTG AAG AAC AAG GAA GTG TCT GTA AAA CGG GTT ACC CAG        879
Thr Phe Asp Leu Lys Asn Lys Glu Val Ser Val Lys Arg Val Thr Gln
            255                 260                 265

GAC CCT AAG CTC CAG ATG GGC AAG AAG CTC CCG CTC CAC CTC ACC CTG        927
Asp Pro Lys Leu Gln Met Gly Lys Lys Leu Pro Leu His Leu Thr Leu
270                 275                 280

CCC CAG GCC TTG CCT CAG TAT GCT GGC TCT GGA AAC CTC ACC CTG GCC        975
Pro Gln Ala Leu Pro Gln Tyr Ala Gly Ser Gly Asn Leu Thr Leu Ala
285                 290                 295                 300

CTT GAA GCG AAA ACA GGA AAG TTG CAT CAG GAA GTG AAC CTG GTG GTG       1023
Leu Glu Ala Lys Thr Gly Lys Leu His Gln Glu Val Asn Leu Val Val
                305                 310                 315

ATG AGA GCC ACT CAG CTC CAG AAA AAT TTG ACC TGT GAG GTG TGG GGA       1071
Met Arg Ala Thr Gln Leu Gln Lys Asn Leu Thr Cys Glu Val Trp Gly
                320                 325                 330

CCC ACC TCC CCT AAG CTG ATG CTG AGC TTG AAA CTG GAG AAC AAG GAG       1119
Pro Thr Ser Pro Lys Leu Met Leu Ser Leu Lys Leu Glu Asn Lys Glu
            335                 340                 345

GCA AAG GTC TCG AAG CGG GAG AAG GCG GTG TGG GTG CTG AAC CCT GAG       1167
Ala Lys Val Ser Lys Arg Glu Lys Ala Val Trp Val Leu Asn Pro Glu
350                 355                 360
```

```
GCG GGG ATG TGG CAG TGT CTG CTG AGT GAC TCG GGA CAG GTC CTG CTG         1215
Ala Gly Met Trp Gln Cys Leu Leu Ser Asp Ser Gly Gln Val Leu Leu
365                 370                 375                 380

GAA TCC AAC ATC AAG GTT CTG CCC ACA TGG TCC ACC CCG GTG                 1257
Glu Ser Asn Ile Lys Val Leu Pro Thr Trp Ser Thr Pro Val
                385                 390

TAATGGCGCC TCTAGA                                                       1273
```

(2) INFORMATION FOR SEQ ID NO:2:

(i) SEQUENCE CHARACTERISTICS:
        (A) LENGTH: 394 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
                20                  25                  30

Lys Gly Asp Thr Val Glu Leu Thr Cys Thr Ala Ser Gln Lys Lys Ser
            35                  40                  45

Ile Gln Phe His Trp Lys Asn Ser Asn Gln Ile Lys Ile Leu Gly Asn
        50                  55                  60

Gln Gly Ser Ser Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Arg Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
            115                 120                 125

Ser Asp Thr His Leu Leu Gln Gly Gln Ser Leu Thr Leu Thr Leu Glu
        130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Asp Phe Ser Phe Pro
210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300
```

```
Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365

Gln Cys Leu Leu Ser Asp Ser Gly Gln Val Leu Leu Glu Ser Asn Ile
370                 375                 380

Lys Val Leu Pro Thr Trp Ser Thr Pro Val
385                 390
```

(2) INFORMATION FOR SEQ ID NO:3:

(i) SEQUENCE CHARACTERISTICS:
        (A) LENGTH: 1742 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 76..1449

(xi) SEQUENCE DESCRIPTION: SEQ ID NO:3:

```
CAAGCCCAGA GCCCTGCCAT TTCTGTGGGC TCAGGTCCCT ACTGCTCAGC CCCTTCCTCC        60

CTCGGCAAGG CCACA ATG AAC CGG GGA GTC CCT TTT AGG CAC TTG CTT CTG       111
                Met Asn Arg Gly Val Pro Phe Arg His Leu Leu Leu
                395                 400                 405

GTG CTG CAA CTG GCG CTC CTC CCA GCA GCC ACT CAG GGA AAC AAA GTG        159
Val Leu Gln Leu Ala Leu Leu Pro Ala Ala Thr Gln Gly Asn Lys Val
            410                 415                 420

GTG CTG GGC AAA AAA GGG GAT ACA GTG GAA CTG ACC TGT ACA GCT TCC        207
Val Leu Gly Lys Lys Gly Asp Thr Val Glu Leu Thr Cys Thr Ala Ser
        425                 430                 435

CAG AAG AAG AGC ATA CAA TTC CAC TGG AAA AAC TCC AAC CAG ATA AAG        255
Gln Lys Lys Ser Ile Gln Phe His Trp Lys Asn Ser Asn Gln Ile Lys
440                 445                 450

ATT CTG GGA AAT CAG GGC TCC TTC TTA ACT AAA GGT CCA TCC AAG CTG        303
Ile Leu Gly Asn Gln Gly Ser Phe Leu Thr Lys Gly Pro Ser Lys Leu
455                 460                 465                 470

AAT GAT CGC GCT GAC TCA AGA AGA AGC CTT TGG GAC CAA GGA AAC TTC        351
Asn Asp Arg Ala Asp Ser Arg Arg Ser Leu Trp Asp Gln Gly Asn Phe
            475                 480                 485

CCC CTG ATC ATC AAG AAT CTT AAG ATA GAA GAC TCA GAT ACT TAC ATC        399
Pro Leu Ile Ile Lys Asn Leu Lys Ile Glu Asp Ser Asp Thr Tyr Ile
        490                 495                 500

TGT GAA GTG GAG GAC CAG AAG GAG GAG GTG CAA TTG CTA GTG TTC GGA        447
Cys Glu Val Glu Asp Gln Lys Glu Glu Val Gln Leu Leu Val Phe Gly
    505                 510                 515

TTG ACT GCC AAC TCT GAC ACC CAC CTG CTT CAG GGG CAG AGC CTG ACC        495
Leu Thr Ala Asn Ser Asp Thr His Leu Leu Gln Gly Gln Ser Leu Thr
520                 525                 530

CTG ACC TTG GAG AGC CCC CCT GGT AGT AGC CCC TCA GTG CAA TGT AGG        543
Leu Thr Leu Glu Ser Pro Pro Gly Ser Ser Pro Ser Val Gln Cys Arg
535                 540                 545                 550

AGT CCA AGG GGT AAA AAC ATA CAG GGG GGG AAG ACC CTC TCC GTG TCT        591
Ser Pro Arg Gly Lys Asn Ile Gln Gly Gly Lys Thr Leu Ser Val Ser
```

-continued

```
             555                 560                 565
CAG CTG GAG CTC CAG GAT AGT GGC ACC TGG ACA TGC ACT GTC TTG CAG      639
Gln Leu Glu Leu Gln Asp Ser Gly Thr Trp Thr Cys Thr Val Leu Gln
            570                 575                 580

AAC CAG AAG AAG GTG GAG TTC AAA ATA GAC ATC GTG GTG CTA GCT TTC      687
Asn Gln Lys Lys Val Glu Phe Lys Ile Asp Ile Val Val Leu Ala Phe
            585                 590                 595

CAG AAG GCC TCC AGC ATA GTC TAT AAG AAA GAG GGG GAA CAG GTG GAG      735
Gln Lys Ala Ser Ser Ile Val Tyr Lys Lys Glu Gly Glu Gln Val Glu
            600                 605                 610

TTC TCC TTC CCA CTC GCC TTT ACA GTT GAA AAG CTG ACG GGC AGT GGC      783
Phe Ser Phe Pro Leu Ala Phe Thr Val Glu Lys Leu Thr Gly Ser Gly
615                 620                 625                 630

GAG CTG TGG TGG CAG GCG GAG AGG GCT TCC TCC TCC AAG TCT TGG ATC      831
Glu Leu Trp Trp Gln Ala Glu Arg Ala Ser Ser Ser Lys Ser Trp Ile
            635                 640                 645

ACC TTT GAC CTG AAG AAC AAG GAA GTG TCT GTA AAA CGG GTT ACC CAG      879
Thr Phe Asp Leu Lys Asn Lys Glu Val Ser Val Lys Arg Val Thr Gln
            650                 655                 660

GAC CCT AAG CTC CAG ATG GGC AAG AAG CTC CCG CTC CAC CTC ACC CTG      927
Asp Pro Lys Leu Gln Met Gly Lys Lys Leu Pro Leu His Leu Thr Leu
            665                 670                 675

CCC CAG GCC TTG CCT CAG TAT GCT GGC TCT GGA AAC CTC ACC CTG GCC      975
Pro Gln Ala Leu Pro Gln Tyr Ala Gly Ser Gly Asn Leu Thr Leu Ala
            680                 685                 690

CTT GAA GCG AAA ACA GGA AAG TTG CAT CAG GAA GTG AAC CTG GTG GTG     1023
Leu Glu Ala Lys Thr Gly Lys Leu His Gln Glu Val Asn Leu Val Val
695                 700                 705                 710

ATG AGA GCC ACT CAG CTC CAG AAA AAT TTG ACC TGT GAG GTG TGG GGA     1071
Met Arg Ala Thr Gln Leu Gln Lys Asn Leu Thr Cys Glu Val Trp Gly
            715                 720                 725

CCC ACC TCC CCT AAG CTG ATG CTG AGC TTG AAA CTG GAG AAC AAG GAG     1119
Pro Thr Ser Pro Lys Leu Met Leu Ser Leu Lys Leu Glu Asn Lys Glu
            730                 735                 740

GCA AAG GTC TCG AAG CGG GAG AAG CCG GTG TGG GTG CTG AAC CCT GAG     1167
Ala Lys Val Ser Lys Arg Glu Lys Pro Val Trp Val Leu Asn Pro Glu
            745                 750                 755

GCG GGG ATG TGG CAG TGT CTG CTG AGT GAC TCG GGA CAG GTC CTG CTG     1215
Ala Gly Met Trp Gln Cys Leu Leu Ser Asp Ser Gly Gln Val Leu Leu
            760                 765                 770

GAA TCC AAC ATC AAG GTT CTG CCC ACA TGG TCC ACC CCG GTG CAG CCA     1263
Glu Ser Asn Ile Lys Val Leu Pro Thr Trp Ser Thr Pro Val Gln Pro
775                 780                 785                 790

ATG GCC CTG ATT GTG CTG GGG GGC GTC GCC GGC CTC CTG CTT TTC ATT     1311
Met Ala Leu Ile Val Leu Gly Gly Val Ala Gly Leu Leu Leu Phe Ile
            795                 800                 805

GGG CTA GGC ATC TTC TTC TGT GTC AGG TGC CGG CAC CGA AGG CGC CAA     1359
Gly Leu Gly Ile Phe Phe Cys Val Arg Cys Arg His Arg Arg Arg Gln
            810                 815                 820

GCA GAG CGG ATG TCT CAG ATC AAG AGA CTC CTC AGT GAG AAG AAG ACC     1407
Ala Glu Arg Met Ser Gln Ile Lys Arg Leu Leu Ser Glu Lys Lys Thr
            825                 830                 835

TGC CAG TGC CCT CAC CGG TTT CAG AAG ACA TGT AGC CCC ATT             1449
Cys Gln Cys Pro His Arg Phe Gln Lys Thr Cys Ser Pro Ile
            840                 845                 850

TGAGGCACGA GGCCAGGCAG ATCCCACTTG CAGCCTCCCC AGGTGTCTGC CCCGCGTTTC   1509

CTGCCTGCGG ACCAGATGAA TGTAGCAGAT CCCACGCTCT GGCCTCCTGT TCGTCCTCCC   1569

TACAATTTGC CATTGTTTCT CCTGGGTTAG GCCCCGGCTT CACTGGTTGA GTGTTGCTCT   1629
```

```
CTAGTTTCCA GAGGCTTAAT CACACCGTCC TCCACGCCAT TTCCTTTTCC TTCAAGCCTA    1689

GCCCTTCTCT CATTATTTCT CTCTGACCCT CTCCCCACTG CTCATTTGGA TCC           1742
```

(2) INFORMATION FOR SEQ ID NO:4:

(i) SEQUENCE CHARACTERISTICS:
        (A) LENGTH: 458 amino acids
        (B) TYPE: amino acid
        (D) TOPOLOGY: linear (ii) MOLECULE TYPE: protein (xi) SEQUENCE DESCRIPTION: SEQ ID NO:4:

```
Met Asn Arg Gly Val Pro Phe Arg His Leu Leu Leu Val Leu Gln Leu
  1               5                  10                  15

Ala Leu Leu Pro Ala Ala Thr Gln Gly Asn Lys Val Val Leu Gly Lys
             20                  25                  30

Lys Gly Asp Thr Val Glu Leu Thr Cys Thr Ala Ser Gln Lys Lys Ser
         35                  40                  45

Ile Gln Phe His Trp Lys Asn Ser Asn Gln Ile Lys Ile Leu Gly Asn
 50                  55                  60

Gln Gly Ser Phe Leu Thr Lys Gly Pro Ser Lys Leu Asn Asp Arg Ala
 65                  70                  75                  80

Asp Ser Arg Arg Ser Leu Trp Asp Gln Gly Asn Phe Pro Leu Ile Ile
                 85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335
```

```
Lys Leu Met Leu Ser Leu Lys Leu Glu Asn Lys Glu Ala Lys Val Ser
            340                 345                 350

Lys Arg Glu Lys Pro Val Trp Val Leu Asn Pro Glu Ala Gly Met Trp
            355                 360                 365

Gln Cys Leu Leu Ser Asp Ser Gly Gln Val Leu Leu Glu Ser Asn Ile
            370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
                405                 410                 415

Phe Phe Cys Val Arg Cys Arg His Arg Arg Arg Gln Ala Glu Arg Met
            420                 425                 430

Ser Gln Ile Lys Arg Leu Leu Ser Glu Lys Lys Thr Cys Gln Cys Pro
            435                 440                 445

His Arg Phe Gln Lys Thr Cys Ser Pro Ile
            450                 455
```

(2) INFORMATION FOR SEQ ID NO:5:

(i) SEQUENCE CHARACTERISTICS:
        (A) LENGTH: 94 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: YES (ix) FEATURE:
        (A) NAME/KEY: Active-site
        (B) LOCATION: 1..94

(xi) SEQUENCE DESCRIPTION: SEQ ID NO:5:

```
Gln Gly Asn Lys Val Val Leu Gly Lys Lys Gly Asp Thr Val Glu Leu
1               5                   10                  15

Thr Cys Thr Ala Ser Gln Lys Lys Ser Ile Gln Phe His Trp Lys Asn
            20                  25                  30

Ser Asn Gln Ile Lys Ile Leu Gly Asn Gln Gly Ser Phe Leu Thr Lys
            35                  40                  45

Gly Pro Ser Lys Leu Asn Asp Arg Ala Asp Ser Arg Arg Ser Leu Trp
            50                  55                  60

Asp Gln Gly Asn Phe Pro Leu Ile Ile Lys Asn Leu Lys Ile Glu Asp
65                  70                  75                  80

Ser Asp Thr Tyr Ile Cys Glu Val Glu Asp Gln Lys Glu Glu
            85                  90
```

(2) INFORMATION FOR SEQ ID NO:6:

(i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: YES (ix) FEATURE:
              (A) NAME/KEY: Active-site
              (B) LOCATION: 1..96

(xi) SEQUENCE DESCRIPTION: SEQ ID NO:6:

Asp Val Gln Met Ile Gln Ser Pro Ser Ser Leu Ser Ala Ser Leu Gly
1               5                  10                  15

Asp Ile Val Thr Met Thr Cys Gln Ala Ser Gln Gly Thr Ser Ile Asn
            20                  25                  30

Leu Asn Trp Phe Gln Gln Lys Pro Gly Lys Ala Pro Lys Leu Leu Ile
        35                  40                  45

Tyr Gly Ala Ser Ile Leu Glu Asp Gly Val Pro Ser Arg Phe Ser Gly
    50                  55                  60

Ser Arg Tyr Gly Thr Asp Phe Thr Leu Thr Ile Ser Ser Leu Glu Asp
65                  70                  75                  80

Glu Asp Met Ala Thr Tyr Phe Cys Leu Gln His Ser Tyr Leu Pro Tyr
                85                  90                  95

(2) INFORMATION FOR SEQ ID NO:7:

(i) SEQUENCE CHARACTERISTICS:
              (A) LENGTH: 14 amino acids
              (B) TYPE: amino acid
              (C) STRANDEDNESS: single
              (D) TOPOLOGY: linear (ii) MOLECULE TYPE: protein (iii) HYPOTHETICAL: YES (iv) ANTI-SENSE: YES (ix) FEATURE:
              (A) NAME/KEY: Active-site
              (B) LOCATION: 1..14

(xi) SEQUENCE DESCRIPTION: SEQ ID NO:7:

Thr Gly Cys Trp Ile Gly Arg Phe Gly Ser Leu Ile Tyr Cys
1               5                  10

(2) INFORMATION FOR SEQ ID NO:8:

(i) SEQUENCE CHARACTERISTICS:
              (A) LENGTH: 102 amino acids
              (B) TYPE: amino acid
              (C) STRANDEDNESS: single
              (D) TOPOLOGY: linear (ii) MOLECULE TYPE: protein (iii) HYPOTHETICAL: YES (iv) ANTI-SENSE: YES (ix) FEATURE:
              (A) NAME/KEY: Active-site
              (B) LOCATION: 1..102

(xi) SEQUENCE DESCRIPTION: SEQ ID NO:8:

Ser Gln Phe Arg Val Ser Pro Leu Asp Arg Thr Trp Asn Leu Gly Glu
1               5                  10                  15

Thr Val Glu Leu Lys Cys Gln Val Leu Leu Ser Asn Pro Thr Ser Gly
            20                  25                  30

Cys Ser Trp Leu Phe Gln Pro Arg Gly Ala Ala Ala Ser Pro Thr Phe
        35                  40                  45

Leu Leu Tyr Leu Ser Gln Asn Lys Pro Lys Ala Ala Glu Gly Leu Asp

```
            50                  55                  60
Thr Gln Arg Phe Ser Gly Lys Arg Leu Gly Asp Thr Phe Val Leu Thr
65                  70                  75                  80

Leu Ser Asp Phe Arg Arg Glu Asn Glu Gly Tyr Tyr Phe Cys Ser Ala
                85                  90                  95

Leu Ser Asn Ser Ile Met
            100
```

(2) INFORMATION FOR SEQ ID NO:9:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: YES (ix) FEATURE:
        (A) NAME/KEY: Active-site
        (B) LOCATION: 1..102

(xi) SEQUENCE DESCRIPTION: SEQ ID NO:9:

```
Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asn Ser Leu
                20                  25                  30

Phe Trp Tyr Arg Gln Thr Met Met Arg Gly Leu Glu Leu Leu Ile Tyr
            35                  40                  45

Phe Asn Asn Asn Val Pro Ile Asp Asp Ser Gly Met Pro Glu Asp Arg
        50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys Ala Ser Ser Phe
                85                  90                  95

Ser Thr Cys Ser Ala Asn
            100
```

(2) INFORMATION FOR SEQ ID NO:10:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: YES (ix) FEATURE:
        (A) NAME/KEY: Active-site
        (B) LOCATION: 1..99

(xi) SEQUENCE DESCRIPTION: SEQ ID NO:10:

```
Gln Lys Val Thr Gln Ala Gln Thr Glu Ile Ser Val Val Glu Lys Glu
1               5                   10                  15

Asp Val Thr Leu Asp Cys Val Tyr Glu Thr Arg Asp Thr Thr Tyr Tyr
                20                  25                  30
```

```
Leu Phe Trp Tyr Lys Gln Pro Pro Ser Gly Glu Leu Val Phe Leu Ile
        35                  40                  45

Arg Arg Asn Ser Phe Asp Glu Gln Asn Glu Ile Ser Gly Arg Tyr Ser
 50                  55                  60

Trp Asn Phe Gln Lys Ser Thr Ser Ser Phe Asn Phe Thr Ile Thr Ala
 65                  70                  75                  80

Ser Gln Val Val Asp Ser Ala Val Tyr Phe Cys Ala Leu Asp Ser Ser
                 85                  90                  95

Ala Ser Lys (2) INFORMATION FOR SEQ ID NO:11:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: YES (ix) FEATURE:
        (A) NAME/KEY: Active-site
        (B) LOCATION: 1..12

(xi) SEQUENCE DESCRIPTION: SEQ ID NO:11:

Leu Val Phe Gly Leu Thr Ala Asn Ser Asp Thr His
 1               5                  10

(2) INFORMATION FOR SEQ ID NO:12:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: YES (ix) FEATURE:
        (A) NAME/KEY: Active-site
        (B) LOCATION: 1..12

(xi) SEQUENCE DESCRIPTION: SEQ ID NO:12:

Leu Tyr Phe Gly Glu Gly Thr Arg Leu Thr Val Leu
 1               5                  10

(2) INFORMATION FOR SEQ ID NO:13:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: YES (ix) FEATURE:
```

(A) NAME/KEY: Active-site
         (B) LOCATION: 1..13

(xi) SEQUENCE DESCRIPTION: SEQ ID NO:13:

Trp Val Phe Gly Gly Gly Thr Lys Val Thr Val Leu Gly
1               5                   10

(2) INFORMATION FOR SEQ ID NO:14:

(i) SEQUENCE CHARACTERISTICS:
         (A) LENGTH: 12 amino acids
         (B) TYPE: amino acid
         (C) STRANDEDNESS: single
         (D) TOPOLOGY: linear (ii) MOLECULE TYPE: protein (iii) HYPOTHETICAL: YES (iv) ANTI-SENSE: YES (ix) FEATURE:
         (A) NAME/KEY: Active-site
         (B) LOCATION: 1..12

(xi) SEQUENCE DESCRIPTION: SEQ ID NO:14:

Thr Phe Gly Gly Gly Thr Lys Leu Glu Ile Lys Arg
1               5                   10

(2) INFORMATION FOR SEQ ID NO:15:

(i) SEQUENCE CHARACTERISTICS:
         (A) LENGTH: 12 amino acids
         (B) TYPE: amino acid
         (C) STRANDEDNESS: single
         (D) TOPOLOGY: linear (ii) MOLECULE TYPE: protein (iii) HYPOTHETICAL: YES (iv) ANTI-SENSE: YES (ix) FEATURE:
         (A) NAME/KEY: Active-site
         (B) LOCATION: 1..12

(xi) SEQUENCE DESCRIPTION: SEQ ID NO:15:

Ile Ile Phe Gly Ser Gly Thr Arg Leu Ser Ile Arg
1               5                   10

(2) INFORMATION FOR SEQ ID NO:16:

(i) SEQUENCE CHARACTERISTICS:
         (A) LENGTH: 31 amino acids
         (B) TYPE: amino acid
         (C) STRANDEDNESS: single
         (D) TOPOLOGY: linear (ii) MOLECULE TYPE: protein (iii) HYPOTHETICAL: YES (iv) ANTI-SENSE: YES (xi) SEQUENCE DESCRIPTION: SEQ ID NO:16:

Ser Thr Pro Val Gln Pro Met Ala Leu Ile Val Leu Gly Gly Val Ala
1               5                   10                  15

Gly Leu Leu Leu Phe Ile Gly Leu Gly Ile Phe Phe Cys Val Arg
            20                  25                  30

```
(2) INFORMATION FOR SEQ ID NO:17:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: YES (ix) FEATURE:
        (A) NAME/KEY: Active-site
        (B) LOCATION: 1..31

(xi) SEQUENCE DESCRIPTION: SEQ ID NO:17:

Ser Thr Ser Ala Gln Asn Lys Met Leu Ser Gly Val Gly Gly Phe Val
1               5                   10                  15

Leu Gly Leu Leu Phe Leu Gly Leu Gly Leu Phe Ile Tyr Phe Arg
            20                  25                  30

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: YES (ix) FEATURE:
        (A) NAME/KEY: CDS
        (B) LOCATION: 1..24

(xi) SEQUENCE DESCRIPTION: SEQ ID NO:18:

ACC CCG GTC CAG CCA ATG GCC CTG                                        24
Thr Pro Val Gln Pro Met Ala Leu
    460                 465

(2) INFORMATION FOR SEQ ID NO:19:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:19:

Thr Pro Val Gln Pro Met Ala Leu
1               5

(2) INFORMATION FOR SEQ ID NO:20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES
```

```
        (iv) ANTI-SENSE: YES (ix) FEATURE:
             (A) NAME/KEY: CDS
             (B) LOCATION: 1..12

(xi) SEQUENCE DESCRIPTION: SEQ ID NO:20:

ACC CCG GTG TAA TGGCGCCTCT AGA                                      25
Thr Pro Val  *
 10

(2) INFORMATION FOR SEQ ID NO:21:

(i) SEQUENCE CHARACTERISTICS:
            (A) LENGTH:  3 amino acids
            (B) TYPE: amino acid
            (D) TOPOLOGY: linear (ii) MOLECULE TYPE: protein (xi) SEQUENCE DESCRIPTION: SEQ ID NO:21:

Thr Pro Val
```